United States Patent
Shen-Gunther

(10) Patent No.: US 11,408,039 B2
(45) Date of Patent: *Aug. 9, 2022

(54) METHODS FOR MOLECULARLY CHARACTERIZING CERVICAL CELL SAMPLES

(71) Applicant: The Government of The United States, as represented by The Secretary of The Army, Fort Detrick, MD (US)

(72) Inventor: Jane Shen-Gunther, San Antonio, TX (US)

(73) Assignee: The Government of The United States, as represented by The Secretary of The Army, Fort Detrick, MD (US)

( * ) Notice: Subject to any disclaimer, the term of this patent is extended or adjusted under 35 U.S.C. 154(b) by 26 days.

This patent is subject to a terminal disclaimer.

(21) Appl. No.: 17/038,290

(22) Filed: Sep. 30, 2020

(65) Prior Publication Data

US 2021/0071265 A1 Mar. 11, 2021

Related U.S. Application Data

(62) Division of application No. 15/741,891, filed as application No. PCT/US2016/049426 on Aug. 30, 2016, now Pat. No. 10,829,820.

(60) Provisional application No. 62/212,555, filed on Aug. 31, 2015.

(51) Int. Cl.
| | |
|---|---|
| *C12Q 1/6886* | (2018.01) |
| *C12Q 1/70* | (2006.01) |
| *C12Q 1/6883* | (2018.01) |
| *C12Q 1/6851* | (2018.01) |
| *C12Q 1/686* | (2018.01) |

(52) U.S. Cl.
CPC .......... *C12Q 1/6886* (2013.01); *C12Q 1/686* (2013.01); *C12Q 1/6851* (2013.01); *C12Q 1/6883* (2013.01); *C12Q 1/708* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS

| | | |
|---|---|---|
| 2004/0010136 A1 | 1/2004 | Au-Young et al. |
| 2005/0227301 A1 | 10/2005 | Glover et al. |
| 2007/0083334 A1 | 4/2007 | Mintz et al. |
| 2008/0311570 A1* | 12/2008 | Lai ...................... C12Q 1/6886 435/6.14 |
| 2009/0181391 A1 | 7/2009 | Karberg et al. |
| 2010/0075334 A1 | 3/2010 | Kim et al. |
| 2010/0143899 A1 | 6/2010 | Bosenberg |
| 2011/0045465 A1 | 2/2011 | Lai |
| 2011/0223180 A1 | 9/2011 | Aldape |
| 2015/0133317 A1 | 5/2015 | Robinson et al. |

FOREIGN PATENT DOCUMENTS

| | | |
|---|---|---|
| EP | 2280077 A1 | 2/2011 |
| EP | 2420578 A1 | 2/2012 |
| EP | 2891719 A1 | 7/2015 |
| TW | 201038739 A | 11/2010 |
| WO | 2009128714 A1 | 10/2009 |
| WO | 2012034170 A1 | 3/2012 |
| WO | 2014029851 A1 | 2/2014 |

OTHER PUBLICATIONS

Office Communication received in EP 16842801.9, dated Feb. 19, 2021.
GenBank Accession No. AC092124, retrieved on Oct. 26, 2016, Aug. 7, 2002.
International Search Report received in PCT/US2016/049426 dated Dec. 29, 2016.
LL573346, GenBank Accession No. LL573346, retrieved on Dec. 12, 2016, Oct. 7, 2014.
GenBank Accession No. LL920055, retrieved on Dec. 12, 2016, Oct. 7, 2014.
Written Opinion received in PCT/US2016/049426 dated Dec. 29, 2016.
Extended European Search report received in EP16842801 dated Jun. 14, 2019.
Shen-Gunther, et al. Molecular Pap smear: HPV genotype and DNA methylation of ADCY8, CDH8, and ZNF582 as an integrated biomarker for high-grade cervical cytology, Clinical Epigenetics, BioMed Central Ltd, GB, vol. 8, Nr: 1, Dec. 1, 2016.
Chang, et al. Triage of Atypical Glandular Cell by SOX1 and POU4F3 Methylation: A Taiwanese Gynecologic Oncology Group (TGOG) Study, PLOS ONE, vol. 10, Nr: 6, p. e0128705.
Farkas, et al. Genome-wide DNA methylation assay reveals novel candidate biomarker genes in cervical cancer, Epigenetics, vol. 8, Nr: 11, pp. 1213-1225, Nov. 1, 2013.
Chen, et al. Methylomics analysis identifies epigenetically silenced genes and implies an activation of β-catenin signaling in cervical cancer: Novel Methylation Biomarkers and CIMP in Cervical Cancer, International Journal of Cancer, John Wiley & Sons, Inc, US, vol. 135, Nr: 1, pp. 117-127, Jul. 1, 2014.

(Continued)

*Primary Examiner* — Amanda Haney
(74) *Attorney, Agent, or Firm* — Leigh Callander; U.S. Army Medical Research and Materiel Command

(57) ABSTRACT

Disclosed herein are methods for molecularly characterizing cervical cell samples as being negative for intraepithelial lesion or malignancy (NILM), low-grade squamous intraepithelial lesion (LSIL), or high-grade squamous intraepithelial lesion (HSIL).

13 Claims, 34 Drawing Sheets

Specification includes a Sequence Listing.

(56) References Cited

OTHER PUBLICATIONS

Lechner, et al. Identification and functional validation of HPV-mediated hypermethylation in head and neck squamous cell carcinoma, Genome Medicine, vol. 5, Nr: 2, p. 15, Feb. 5, 2013.

"NC_000016.10" *Homo sapiens* chromosome 16, GRCh38.p12 Primary Assembly—Nucleotide—NCBI, Genome Reference Consortium, Dec. 21, 2017.

Liou, et al. Comparison of HPV genotyping and methylated ZNF582 as triage for women with equivocal liquid-based cytology results, Clinical Epigenetics, BioMed Central Ltd, London, UK, vol. 7, Nr: 1, p. 50, Apr. 28, 2015.

Chiarle, et al. The anaplastic lymphoma kinase in the pathogenesis of cancer, Nature Reviews. Cancer, vol. 8, Nr: 1, pp. 11-23, Jan. 1, 2008.

Brentnall, et al. A DNA methylation classifier of cervical precancer based on human papillomavirus and human genes, International Journal of Cancer, Union Internationale Centre Ie Cancer, vol. 135, Nr: 6, pp. 1425-1432, Sep. 15, 2014.

Lai, et al. Identification of novel DNA methylation markers in cervical cancer, Int. J. Cancer, 123:161-167, Apr. 8, 2008.

Yue, Yaofei et al. "Genetic variability in L1 and L2 genes of HPV-16 and HPV-58 in Southwest China." PloS one vol. 8,1 (2013): e55204.

Liu ZJ, Maekawa M. Polymerase chain reaction-based methods of DNA methylation analysis. Anal Biochem. Jun. 15, 2003;317(2):259-65.

Xie H, Tubbs R, Yang B. Detection of MGMT promoter methylation in glioblastoma using pyrosequencing. Int J Clin Exp Pathol. 2015;8(1):636-642. Published Jan. 1, 2015.

\* cited by examiner

| Clinical and cytological characteristics of the study population | |
|---|---|
| Characteristics | N (%)[g] |
| *Clinical* | |
| Age[a] | |
| Median (IQR) | 28 (24-35) |
| Range (year) | 19-67 |
| | |
| Race/Ethnicity[a] | |
| Asian [NILM, LSIL, HSIL] | 9 [5, 3, 1] (3) |
| Black [NILM, LSIL, HSIL] | 40 [14, 15, 11] (14) |
| White [NILM, LSIL, HSIL] | 124 [48, 40, 36] (45) |
| Other [NILM, LSIL, HSIL] | 65 [21, 28, 16] (24) |
| Unknown [NILM, LSIL, HSIL] | 39 [12, 14, 13] (14) |
| | |
| *Cytological* [b] | |
| Total LBC samples collected | 400 (100) |
| LBC samples excluded[c] | 123 (31) |
| NILM | 33 |
| LSIL | 85 |
| HSIL | 5 |
| LBC samples included | 277 (69) |
| NILM | 100 |
| LSIL | 100 |
| HSIL | 77 |
| Source[d] | |
| Cervical | 276 (99.6) |
| Vaginal | 1 (0.4) |
| Diagnostic category[d] | |
| Normal | 100 (36) |
| Abnormal | 177 (64) |
| Cellular DNA concentration[d,e,f] | |
| NILM | 100 |
| Median (ng/uL) (IQR) | 48.1 (37.1-74.3) |
| Range (ng/uL) | 20.8-181.5 |
| LSIL | 100 |
| Median (ng/uL) (IQR) | 46.3 (35.6-63.1) |
| Range (ng/uL) | 20.5-182.8 |
| HSIL | 77 |
| Median (ng/uL) (IQR) | 51.8 (34.9-71.3) |
| Range (ng/uL) | 11.5-154.0 |

[a] Age and Race/Ethnicity of subjects (N=277) are based on the demographic data of included samples. The number of samples by race/ethnicity and cytological diagnosis are placed in square brackets. The distribution of the 5 categories of race/ethnicity (inclusive of Other and Unknown) among the 3 cytological grades were not statistically different ($\chi^2$, $P=0.777$).

[b] Cytopathology results are ascribed to the specimens collected on day of study enrollment.

[c] Exclusion criteria included: low cell pellet volume (<200 uL); low cellular DNA concentration (<20 ng/uL); low nucleic acid purity (spectrophotometry absorbance ratio 260/230 nm < 0.7); excess samples (>100) (see text for details).

[d] Data based on included samples (N=277).

[e] Concentration of total cellular DNA per sample after manual or semi-automated DNA extraction.

[f] Comparison of DNA concentrations between NILM, LSIL, and HSIL samples were not statistically different ($P=0.519$) by Kruskal-Wallis test.

[g] Values are N (%) unless otherwise denoted.

Figure 1

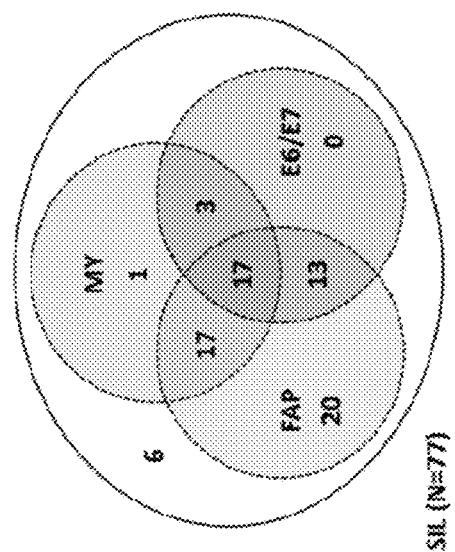
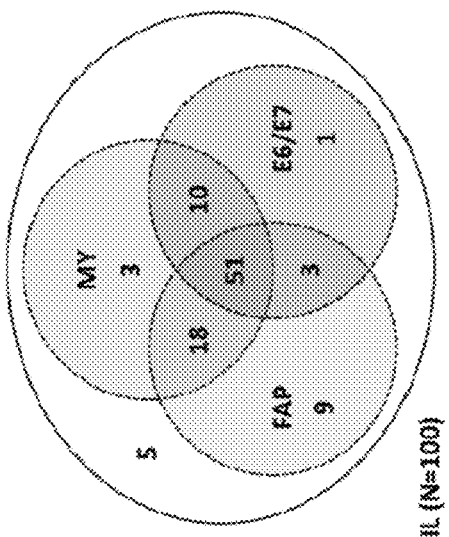
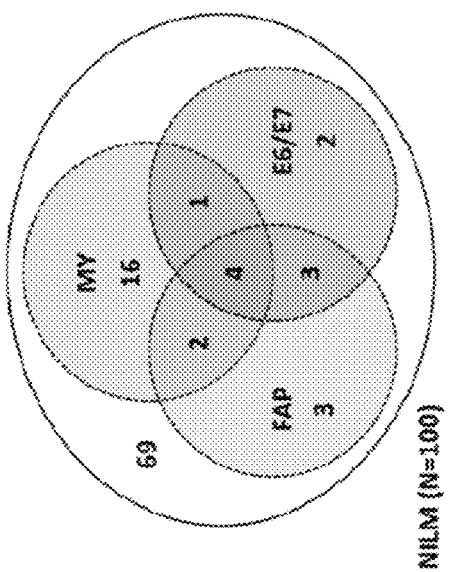
Figure 3

Logistic regression analysis of HPV and HPV + *ZNF582* for predicting abnormal (LSIL/HSIL) cytology

| Variable | Coefficient (β) | SE | z | P>z | OR | 95% CI | | |
|---|---|---|---|---|---|---|---|---|
| Univariable model | | | | | | | | |
| HPV[a] | 1.77 | 0.27 | 6.50 | 0.00 | 5.86 | 3.44 | to | 9.99 |
| constant | -1.66 | 0.47 | -3.52 | 0.00 | 0.19 | 0.08 | to | 0.48 |
| Multivariable model | | | | | | | | |
| HPV[a] | 1.80 | 0.31 | 5.84 | 0.00 | 6.04 | 3.30 | to | 11.04 |
| *ZNF582*[b] | 2.69 | 0.88 | 3.05 | 0.00 | 14.72 | 2.61 | to | 83.06 |
| constant | -2.51 | 0.66 | -3.80 | 0.00 | 0.08 | 0.02 | to | 0.30 |

HPV, human papillomavirus; HSIL, high-grade squamous intraepithelial lesion; LSIL, low-grade squamous intraepithelial lesion; ZNF, *ZNF582* gene; SE, standard error; z, z-score.

[a]The HPV genotype identified in each sample was coded accordingly: HPV undetected (0), not classifiable (1), possibly carcinogenic (2), and carcinogenic (3).

[b]The quantified promoter methylation level (%) of *ZNF582* gene at CpG-position 3 of each sample was binarized accordingly: <1.1 (0), ≥1.1 (1).

Figure 13

Logistic regression analysis of HPV and HPV + *ADCY8*, *CDH8*, and *ZNF582* for predicting for HSIL cytology

| Variable | Coefficient (β) | SE | z | P>z | OR | 95% CI | | |
|---|---|---|---|---|---|---|---|---|
| Univariable model | | | | | | | | |
| HPV[a] | 1.41 | 0.32 | 4.42 | 0.00 | 4.09 | 2.19 | to | 7.65 |
| constant | -3.95 | 0.90 | -4.37 | 0.00 | 0.02 | 0.00 | to | 0.11 |
| Multivariable model | | | | | | | | |
| HPV[a] | 1.55 | 0.37 | 4.19 | 0.00 | 4.72 | 2.28 | to | 9.74 |
| *ADCY8*[b] | 1.16 | 0.48 | 2.40 | 0.02 | 3.17 | 1.24 | to | 8.15 |
| *CDH8*[c] | 1.04 | 0.46 | 2.26 | 0.02 | 2.82 | 1.15 | to | 6.95 |
| *ZNF58*[d] | 1.36 | 0.46 | 2.98 | 0.00 | 3.91 | 1.59 | to | 9.59 |
| constant | -5.78 | 1.13 | -5.12 | 0.00 | 0.00 | 0.00 | to | 0.03 |

HPV, human papillomavirus; HSIL, high-grade squamous intraepithelial lesion; LSIL, low-grade squamous intraepithelial lesion; ZNF, *ZNF582* gene; SE, standard error; z, z-score.

[a]The HPV genotype identified in each sample was coded accordingly: HPV undetected (0), not classifiable (1), possibly carcinogenic (2), and carcinogenic (3).

[b]The quantified promoter methylation level (%) of *ADCY8* gene at CpG-position 7 of each sample was binarized accordingly: <5.8 (0), ≥5.8 (1).

[c]The quantified promoter methylation level (%) of *CDH8* gene at CpG-position 3 of each sample was binarized accordingly: <3.0 (0), ≥3.0 (1).

[d]The quantified promoter methylation level (%) of *ZNF582* gene at CpG-position 3 of each sample was binarized accordingly: <1.1 (0), ≥1.1 (1).

Figure 14

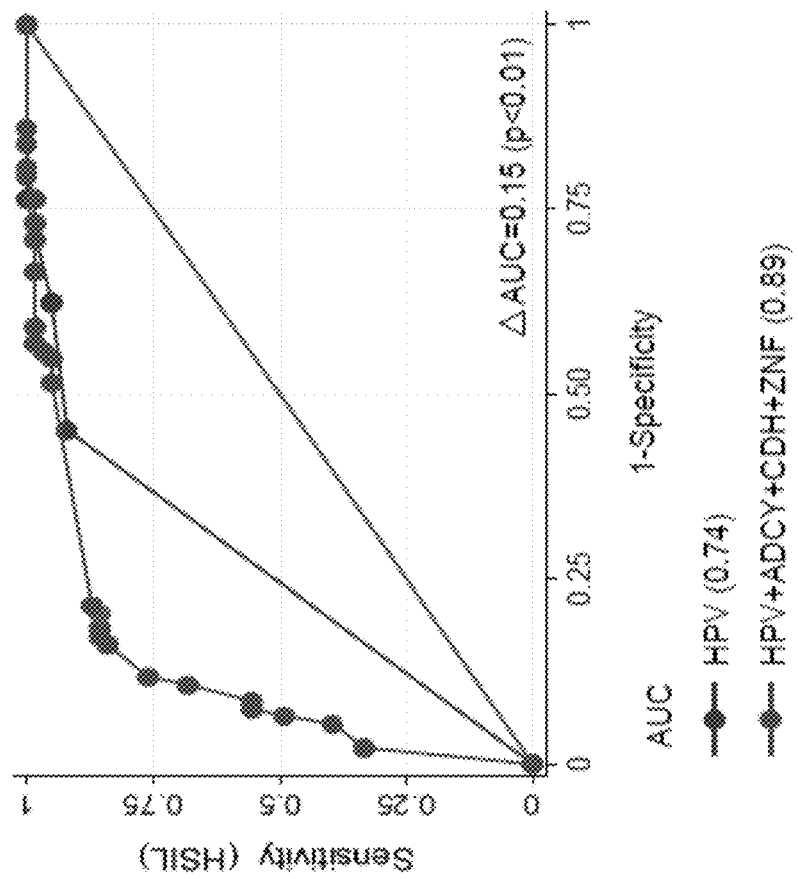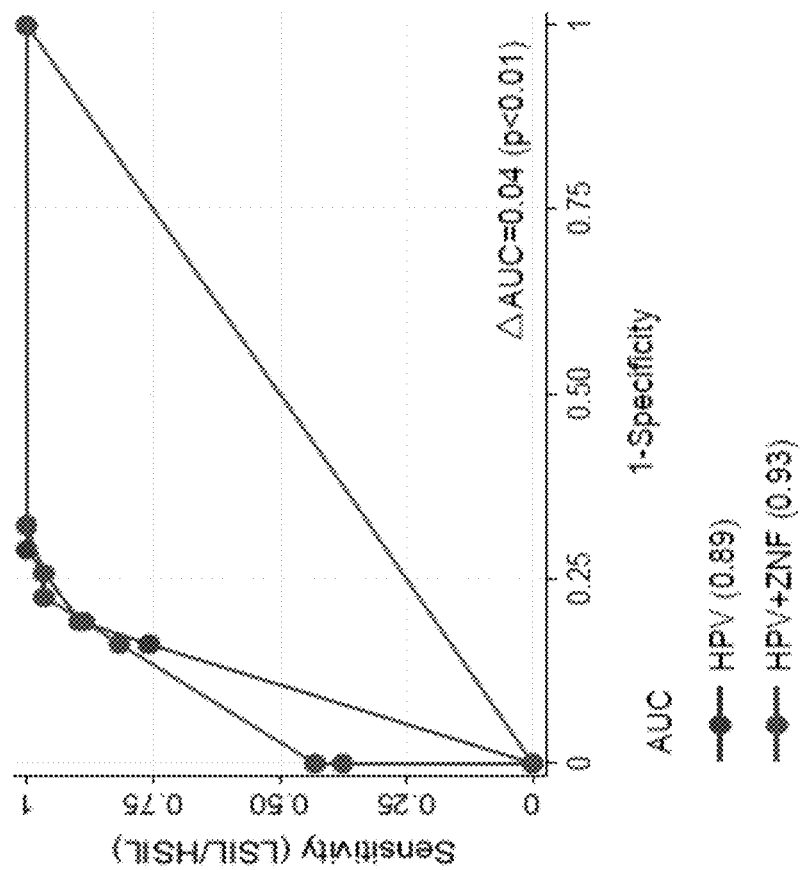
Figure 15

Predictive margins for abnormal (LSIL/HSIL) cytology based on HPV or HPV + *ZNF582*

| Outcome | MER at | Predictors HPV[a] | ZNF[b] | Predicted Probability Statistics Margin[c] | SE | z | P>z | 95% CI | | |
|---|---|---|---|---|---|---|---|---|---|---|
| | | | | Univariable logit model | | | | | | |
| NILM (0), LSIL/HSIL (1) | 1 | 0 | - | 0.16 | 0.06 | 2.52 | 0.01 | 0.04 | to | 0.28 |
| | 2 | 1 | - | 0.53[d] | 0.08 | 6.81 | 0.00 | 0.38 | to | 0.68 |
| | 3 | 2 | - | 0.87 | 0.04 | 21.93 | 0.00 | 0.79 | to | 0.94 |
| | 4 | 3 | - | 0.97 | 0.01 | 73.23 | 0.00 | 0.95 | to | 1.00 |
| | | | | Multivariable logit model | | | | | | |
| NILM (0), LSIL/HSIL (1) | 1 | 0 | 0 | 0.08 | 0.05 | 1.64 | 0.10 | -0.01 | to | 0.17 |
| | 2 | 0 | 1 | 0.55 | 0.21 | 2.57 | 0.01 | 0.13 | to | 0.96 |
| | 3 | 1 | 0 | 0.33[d] | 0.10 | 3.41 | 0.00 | 0.14 | to | 0.52 |
| | 4 | 1 | 1 | 0.88 | 0.08 | 10.55 | 0.00 | 0.72 | to | 1.04 |
| | 5 | 2 | 0 | 0.75 | 0.07 | 10.72 | 0.00 | 0.61 | to | 0.89 |
| | 6 | 2 | 1 | 0.98 | 0.02 | 54.45 | 0.00 | 0.94 | to | 1.01 |
| | 7 | 3 | 0 | 0.95 | 0.03 | 36.30 | 0.00 | 0.90 | to | 1.00 |
| | 8 | 3 | 1 | 1.00 | 0.00 | 275.01 | 0.00 | 0.99 | to | 1.00 | at, a number of possible combinations of representative values from each predictor variable; HPV, human papillomavirus; HSIL, high-grade squamous intraepithelial lesion; LSIL, low-grade squamous intraepithelial lesion; MER, marginal effect at representative values (a statistical method to calculate margins); NILM, negative for intraepithelial lesion/malignancy; ZNF, *ZNF582* gene; SE, standard error; z, z-score.

[a] The HPV genotype identified in each sample was coded accordingly: HPV undetected (0), not classifiable (1), possibly carcinogenic (2), and carcinogenic (3).

[b] The quantified promoter methylation level (%) of *ZNF582* gene at CpG-position 3 of each sample was binarized accordingly: <1.1 (0), ≥1.1 (1).

[c] The margin is the predicted probability for the outcome of interest based on representative values from each predictor variable.

[d] The margins (in bold) are the positive outcome or "classification threshold" probabilities used for classification of outcomes and the evaluation of diagnostic test performance. The classification threshold is estimated by using the maximum sum of sensitivity and specificity (Youden's index).

Figure 19

Predictive margins for HSIL cytology based on HPV or HPV + 3-gene methylation markers

| Outcome | MER at | Predictors | | | | Predicted Probability Statistics | | | | 95% CI | |
|---|---|---|---|---|---|---|---|---|---|---|---|
| | | HPV[a] | ADCY[b] | CDH[b] | ZNF[b] | Margin[c] | SE | z | P>z | | |
| Univariable logit model | | | | | | | | | | | |
| NILM/LSIL (0), HSIL (1) | 1 | 0 | - | - | - | 0.02 | 0.02 | 1.13 | 0.26 | -0.01 to | 0.05 |
| | 2 | 1 | - | - | - | 0.07 | 0.04 | 1.81 | 0.07 | -0.01 to | 0.15 |
| | 3 | 2 | - | - | - | 0.24 | 0.06 | 4.30 | 0.00 | 0.13 to | 0.36 |
| | 4 | 3 | - | - | - | 0.57 | 0.05 | 11.71 | 0.00 | 0.47 to | 0.67 |
| Multivariable logit model | | | | | | | | | | | |
| NILM/LSIL (0), HSIL (1) | 1 | 0 | 0 | 0 | 0 | 0.00 | 0.00 | 0.89 | 0.37 | 0.00 to | 0.01 |
| | 2 | 0 | 0 | 0 | 1 | 0.01 | 0.01 | 0.93 | 0.35 | -0.01 to | 0.04 |
| | 3 | 0 | 0 | 1 | 0 | 0.01 | 0.01 | 0.89 | 0.37 | -0.01 to | 0.03 |
| | 4 | 0 | 0 | 1 | 1 | 0.03 | 0.03 | 0.96 | 0.34 | -0.03 to | 0.10 |
| | 5 | 0 | 1 | 0 | 0 | 0.01 | 0.01 | 0.88 | 0.38 | -0.01 to | 0.03 |
| | 6 | 0 | 1 | 0 | 1 | 0.04 | 0.04 | 0.97 | 0.33 | -0.04 to | 0.11 |
| | 7 | 0 | 1 | 1 | 0 | 0.03 | 0.03 | 0.92 | 0.36 | -0.03 to | 0.08 |
| | 8 | 0 | 1 | 1 | 1 | 0.10 | 0.09 | 1.09 | 0.28 | -0.08 to | 0.27 |
| | 9 | 1 | 0 | 0 | 0 | 0.01 | 0.01 | 1.30 | 0.20 | -0.01 to | 0.04 |
| | 10 | 1 | 0 | 0 | 1 | 0.05 | 0.04 | 1.39 | 0.16 | -0.02 to | 0.13 |
| | 11 | 1 | 0 | 1 | 0 | 0.04 | 0.03 | 1.30 | 0.20 | -0.02 to | 0.10 |
| | 12 | 1 | 0 | 1 | 1 | 0.14 | 0.09 | 1.51 | 0.13 | -0.04 to | 0.32 |
| | 13 | 1 | 1 | 0 | 0 | 0.04 | 0.04 | 1.25 | 0.21 | -0.02 to | 0.11 |
| | 14 | 1 | 1 | 0 | 1 | 0.15 | 0.10 | 1.56 | 0.12 | -0.04 to | 0.35 |
| | 15 | 1 | 1 | 1 | 0 | 0.12 | 0.08 | 1.41 | 0.16 | -0.05 to | 0.28 |
| | 16 | 1 | 1 | 1 | 1 | 0.34 | 0.16 | 2.13 | 0.03 | 0.03 to | 0.65 |
| | 17 | 2 | 0 | 0 | 0 | 0.06 | 0.03 | 2.25 | 0.02 | 0.01 to | 0.12 |
| | 18 | 2 | 0 | 0 | 1 | 0.21 | 0.08 | 2.55 | 0.01 | 0.05 to | 0.38 |
| | 19 | 2 | 0 | 1 | 0 | 0.16 | 0.07 | 2.22 | 0.03 | 0.02 to | 0.31 |
| | 20 | 2 | 0 | 1 | 1 | 0.43 | 0.13 | 3.25 | 0.00 | 0.17 to | 0.69 |
| | 21 | 2 | 1 | 0 | 0 | 0.18 | 0.09 | 2.08 | 0.04 | 0.01 to | 0.35 |
| | 22 | 2 | 1 | 0 | 1 | 0.46 | 0.13 | 3.49 | 0.00 | 0.20 to | 0.72 |
| | 23 | 2 | 1 | 1 | 0 | 0.38 | 0.13 | 2.85 | 0.00 | 0.12 to | 0.64 |
| | 24 | 2 | 1 | 1 | 1 | 0.71 | 0.10 | 6.94 | 0.00 | 0.51 to | 0.91 |
| | 25 | 3 | 0 | 0 | 0 | 0.25 | 0.06 | 3.94 | 0.00 | 0.12 to | 0.37 |
| | 26 | 3 | 0 | 0 | 1 | 0.56 | 0.11 | 5.13 | 0.00 | 0.35 to | 0.77 |
| | 27 | 3 | 0 | 1 | 0 | 0.48 | 0.11 | 4.20 | 0.00 | 0.26 to | 0.70 |
| | 28 | 3 | 0 | 1 | 1 | 0.78 | 0.09 | 8.79 | 0.00 | 0.61 to | 0.96 |
| | 29 | 3 | 1 | 0 | 0 | 0.51 | 0.13 | 3.95 | 0.00 | 0.26 to | 0.76 |
| | 30 | 3 | 1 | 0 | 1 | 0.80 | 0.08 | 9.79 | 0.00 | 0.64 to | 0.96 |
| | 31 | 3 | 1 | 1 | 0 | 0.74 | 0.10 | 7.47 | 0.00 | 0.55 to | 0.94 |
| | 32 | 3 | 1 | 1 | 1 | 0.92 | 0.04 | 24.54 | 0.00 | 0.85 to | 0.99 |

3-gene methylation markers (*ADCY8, CDH8, ZNF582*); ADCY, *ADCY8* gene; at, a number of possible combinations of representative values from each predictor variable; CDH, *CDH8* gene; HPV, human papillomavirus; HSIL, high-grade squamous intraepithelial lesion; LSIL, low-grade squamous intraepithelial lesion; MER, marginal effect at representative values (a statistical method to calculate margins); NILM, negative for intraepithelial lesion/malignancy; ZNF, *ZNF582* gene; SE, standard error; z, z-score.

[a]The HPV genotype identified in each sample was coded accordingly: HPV undetected (0), not classifiable (1), possibly carcinogenic (2), and carcinogenic (3).

[b]The quantified promoter methylation level (%) of *ADCY8* at CpG-position 7, *CDH8* at CpG-position 3, and *ZNF582* at CpG-position 3 of each sample was binarized respectively: <5.8 (0), ≥5.8 (1); <3.0 (0), ≥3.0 (1); <1.1 (0), ≥1.1 (1).

[c]The margin is the predicted probability for the outcome of interest based on representative values from each predictor variable.

Figure 20

Diagnostic performance of HPV vs. HPV + *ZNF582* for abnormal (LSIL/HSIL) cytology

| Parameters | Biomarkers | |
|---|---|---|
| | HPV | HPV + *ZNF582* |
| Disease (cytological)[a] | | |
| Present (LSIL/HSIL) | 125 (80) | 125 (80) |
| Absent (NILM) | 31 (20) | 31 (20) |
| Total | 156 (100) | 156 (100) |
| Diagnostic performance[b,c] | | |
| Sensitivity | 112/125 (90) | 125/125 (100) |
| Specificity | 25/31 (81) | 21/31 (68) |
| PPV | 112/118 (95) | 125/135 (93) |
| NPV | 25/38 (66) | 21/21 (100) |
| False-positive | 6/118 (5) | 10/135 (7) |
| False-negative | 13/38 (34) | 0/21 (0) |
| LR + test (TP/FP) | 4.74 | 3.13 |
| LR - test (FN/TN) | 0.123 | 0 |
| Accuracy, % | 137/156 (88) | 146/156 (94) |

FN, false negative; FP, false positive; HPV, human papillomavirus; HSIL, high-grade squamous intraepithelial lesion; LR, likelihood ratio; LSIL, low-grade squamous intraepithelial lesion; NILM, negative for intraepithelial lesion/malignancy; TN, true negative; TP, true positive; ZNF, *ZNF582* gene.

[a]The disease state was defined by the cytological diagnosis of the specimen at study entry. It served as the reference standard for the clinical performance of the molecular tests, *i.e.*, HPV and HPV + *ZNF582*.

[b]The positive outcome or "classification threshold" probabilities used for classification of outcomes for HPV and HPV + *ZNF582* were 0.53 and 0.33 respectively.

[c]Values are n/N (%) unless denoted otherwise.

Figure 21

Diagnostic performance of HPV vs. HPV + 3-gene methylation markers for HSIL cytology

|  | Biomarkers | |
|---|---|---|
| Parameters | HPV | HPV + *ADCY8* + *CDH8* + *ZNF582* |
| Disease (cytological)[a] | | |
| Present (HSIL) | 63 (40) | 63 (40) |
| Absent (NILM/LSIL) | 93 (60) | 93 (60) |
| Total | 156 (100) | 156 (100) |
| Diagnostic performance[b,c] | | |
| Sensitivity | 58/63 (92) | 48/63 (76) |
| Specificity | 51/93 (55) | 82/93 (88) |
| PPV | 58/100 (58) | 48/59 (81) |
| NPV | 51/56 (91) | 82/97 (85) |
| False-positive | 42/100 (42) | 11/59 (19) |
| False-negative | 5/56 (9) | 15/97 (15) |
| LR + test (TP/FP) | 2.04 | 6.33 |
| LR - test (FN/TN) | 0.15 | 0.27 |
| Accuracy, % | 109/156 (70) | 130/156 (83) |

ADCY, *ADCY8* gene; CDH, *CDH8* gene; FN, false negative; FP, false positive; HPV, human papillomavirus; HSIL, high-grade squamous intraepithelial lesion; LR, likelihood ratio; LSIL, low-grade squamous intraepithelial lesion; NILM, negative for intraepithelial lesion/malignancy; TN, true negative; TP, true positive; ZNF, *ZNF582* gene.
[a]The disease state was defined by the cytological diagnosis of the specimen at study entry. It served as the reference standard for the clinical performance of the molecular tests, *i.e.*, HPV and HPV + 3-gene methylation markers.
[b]The positive outcome or "classification threshold" probabilities used for classification of outcomes for HPV and HPV + 3-gene methylation markers were 0.57 and 0.48, respectively.
[c]Values are n/N (%) unless denoted otherwise.

Figure 22

Logistic regression analysis of HPV and HPV + *ALK* methylation marker for predicting HSIL cytology

| Variable | Coefficient ($\beta$) | SE | z | P>z | OR | 95% CI | | |
|---|---|---|---|---|---|---|---|---|
| Univariable model | | | | | | | | |
| HPV[a] | 1.41 | 0.32 | 4.42 | 0.00 | 4.09 | 2.19 | to | 7.65 |
| constant | -3.95 | 0.90 | -4.37 | 0.00 | 0.02 | 0.00 | to | 0.11 |
| Multivariable model | | | | | | | | |
| HPV[a] | 1.67 | 0.38 | 4.39 | 0.00 | 5.31 | 2.52 | to | 11.20 |
| *ALK*[b] | 0.97 | 0.39 | 2.48 | 0.01 | 2.62 | 1.23 | to | 5.63 |
| constant | -5.13 | 1.10 | -4.64 | 0.00 | 0.01 | 0.00 | to | 0.05 |

HPV, human papillomavirus; HSIL, high-grade squamous intraepithelial lesion; LSIL, low-grade squamous intraepithelial lesion; *ALK*, *ALK* gene; SE, standard error; z, z-score.
[a]The HPV genotype identified in each sample was coded accordingly: HPV undetected (0), not classifiable (1), possibly carcinogenic (2), and carcinogenic (3).
[b]The quantified promoter methylation level (%) of *ALK* gene at CpG-position 5 of each sample was binarized accordingly: <1.0 (0), ≥1.0 (1).

Figure 23

Predictive margins for HSIL cytology based on HPV or HPV + ALK

| Outcome | MER at | Predictors HPV[a] | ALK[b] | Predicted Probability Statistics Margin[c] | SE | z | P>z | 95% CI | | |
|---|---|---|---|---|---|---|---|---|---|---|
| | | | | Univariable logit model | | | | | | |
| NILM/LSIL (0), HSIL (1) | 1 | 0 | - | 0.02 | 0.02 | 1.13 | 0.26 | -0.01 | to | 0.05 |
| | 2 | 1 | - | 0.07 | 0.04 | 1.81 | 0.07 | -0.01 | to | 0.15 |
| | 3 | 2 | - | 0.24 | 0.06 | 4.30 | 0.00 | 0.13 | to | 0.36 |
| | 4 | 3 | - | 0.57 | 0.05 | 11.71 | 0.00 | 0.47 | to | 0.67 |
| | | | | Multivariable logit model | | | | | | |
| NILM/LSIL (0), HSIL (1) | 1 | 0 | 0 | 0.01 | 0.01 | 0.91 | 0.36 | 0.01 | to | 0.02 |
| | 2 | 0 | 1 | 0.02 | 0.02 | 0.94 | 0.35 | 0.02 | to | 0.05 |
| | 3 | 1 | 0 | 0.03 | 0.02 | 1.39 | 0.17 | 0.01 | to | 0.07 |
| | 4 | 1 | 1 | 0.08 | 0.05 | 1.5 | 0.13 | 0.02 | to | 0.18 |
| | 5 | 2 | 0 | 0.14 | 0.05 | 2.81 | 0.01 | 0.04 | to | 0.24 |
| | 6 | 2 | 1 | 0.30 | 0.08 | 3.63 | 0.00 | 0.14 | to | 0.47 |
| | 7 | 3 | 0 | 0.47 | 0.07 | 6.59 | 0.00 | 0.33 | to | 0.61 |
| | 8 | 3 | 1 | 0.70 | 0.06 | 11.62 | 0.00 | 0.58 | to | 0.82 | at, number of possible combinations of representative values from each predictor variable; HPV, human papillomavirus; HSIL, high-grade squamous intraepithelial lesion; LSIL, low-grade squamous intraepithelial lesion; MER, marginal effect at representative values (a statistical method to calculate margins); NILM, negative for intraepithelial lesion/malignancy; ALK, ALK gene; SE, standard error; z, z-score.

[a] The HPV genotype identified in each sample was coded accordingly: HPV undetected (0), not classifiable (1), possibly carcinogenic (2), and carcinogenic (3).

[b] The quantified promoter methylation level (%) of ALK gene at CpG-position 5 of each sample was binarized accordingly: <1.0 (0), ≥1.0 (1).

[c] The margin is the predicted probability for the outcome of interest based on representative values from each predictor variable.

Figure 26

List of pyrosequencing assays

| Assay | Primer | Sequence 5' to 3' |
|---|---|---|
| ADCY8_a1 | Forward | AGTGGAGGTTAGGGTAAAGTTT (SEQ ID NO: 12) |
|  | Reverse | Biotin-TAACCCCTCCATAACTATAACCCCCATTAA (SEQ ID NO: 13) |
|  | Sequencing | GGGAGGAGGTTTTAATTATT (SEQ ID NO: 14) |
| ALK_a7 | Forward | GGTAGAGGTGGTAGTAGTTGGTATT (SEQ ID NO: 15) |
|  | Reverse | Biotin-CCCTCCTCACCCATCATCA (SEQ ID NO: 16) |
|  | Sequencing | GTGGTAGTAGTTGGTATTT (SEQ ID NO: 17) |
| CDH8_01 | HS_CDH8_01_PM PyroMark CpG Assay, Product No. 978746, Cat. No. PM00062944 (Qiagen) | |
| MGMT_01 | Hs_MGMT_01_PM PyroMark CpG Assay, Product No. 978746, Cat. No. PM00149702 (Qiagen) | |
| ZNF582_01 | Hs_ZNF582_01_PM PyroMark CpG Assay, Product No. 978746, Cat. No. PM00071925 (Qiagen) | |

Figure 29

Table 1: Location for all assayed ADCY8 CpG sites.

| Assay ID | CpG site # | Genomic coordinate (NCBI36/hg18, chr8) | Downstream from TSS (bp) |
|---|---|---|---|
| ADCY8 | 1 | 132121525 | 492 |
|  | 2 | 132121523 | 494 |
|  | 3 | 132121520 | 497 |
|  | 4 | 132121507 | 510 |
|  | 5 | 132121502 | 515 |
|  | 6 | 132121499 | 518 |
|  | 7 | 132121484 | 533 |
|  | 8 | 132121475 | 542 |

Note: Transcription start site (TSS, chr8: 132122017) is based on RefSeq NM_001115.

Table 2: Location for all assayed CDH8 CpG sites.

| Assay ID | CpG site # | Genomic coordinate (NCBI36/hg18, chr16) | Downstream from TSS (bp) |
|---|---|---|---|
| CDH8 | 1 | 60626720 | 1520 |
|  | 2 | 60626726 | 1514 |
|  | 3 | 60626735 | 1505 |
|  | 4 | 60626752 | 1488 |
|  | 5 | 60626758 | 1482 |

Note: Transcription start site (TSS, chr16:60628240) is based on RefSeq NM_001796.

Table 3: Location for all assayed MGMT sites.

| Assay ID | CpG site # | Genomic coordinate (NCBI36/hg18, chr10) | Upstream from TSS (bp) |
|---|---|---|---|
| MGMT | 1 | 131155870 | 426 |
|  | 2 | 131155872 | 428 |
|  | 3 | 131155874 | 430 |
|  | 4 | 131155881 | 437 |
|  | 5 | 131155888 | 444 |
|  | 6 | 131155891 | 447 |
|  | 7 | 131155895 | 451 |

Note: Transcription start site (TSS, chr10: 131155444) is based on RefSeq NM_002412.

Table 4: Location for all assayed ZNF582 CpG sites.

| Assay ID | CpG site # | Genomic coordinate (NCBI36/hg18, chr19) | Downstream from TSS (bp) |
|---|---|---|---|
| ZNF582 | 1 | 61596535 | 166 |
|  | 2 | 61596528 | 173 |
|  | 3 | 61596523 | 178 |
|  | 4 | 61596515 | 186 |
|  | 5 | 61596512 | 189 |

Note: Transcription start site (TSS, chr19: 61596701) is based on RefSeq NM_144690.

Figure 30

| Temp X | Meth_100_Std Mean Fluor | interval e.g. 71.0 to 71.2 | f(x) at midpoints | interval x midpoint |
|---|---|---|---|---|
| 71 | -0.341759649 | | 0 | 0 |
| 71.1 | -0.064882339 | 0.2 | -0.064882339 | -0.012976468 |
| 71.2 | 0.211994972 | | 0 | 0 |
| 71.3 | 0.3964997 | 0.2 | 0.3964997 | 0.07929994 |
| 71.4 | 0.384672966 | | 0 | 0 |
| 71.5 | 0.301286538 | 0.2 | 0.301286538 | 0.060257308 |
| 71.6 | 0.179192108 | | 0 | 0 |
| 71.7 | -0.013478301 | 0.2 | -0.013478301 | -0.00269566 |
| 71.8 | -0.219392068 | | 0 | 0 |
| 71.9 | -0.384221637 | 0.2 | -0.384221637 | -0.076844327 |
| 72 | -0.578588046 | | 0 | 0 |
| 72.1 | -0.83735194 | 0.2 | -0.83735194 | -0.167470388 |
| 72.2 | -1.125489066 | | 0 | 0 |
| 72.3 | -1.308509651 | 0.2 | -1.308509651 | -0.26170193 |
| 72.4 | -1.362403471 | | 0 | 0 |
| 72.5 | -1.328972099 | 0.2 | -1.328972099 | -0.26579442 |
| 72.6 | -1.238967681 | | 0 | 0 |
| 72.7 | -1.032323862 | 0.2 | -1.032323862 | -0.206464772 |
| 72.8 | -0.796222004 | | 0 | 0 |
| 72.9 | -0.553760253 | 0.2 | -0.553760253 | -0.110752051 |
| 73 | -0.355984652 | | 0 | 0 |
| 73.1 | -0.147314029 | 0.2 | -0.147314029 | -0.029462806 |
| 73.2 | 0.012963922 | | 0 | 0 |
| 73.3 | 0.144153362 | 0.2 | 0.144153362 | 0.028830672 |
| 73.4 | 0.221981973 | | 0 | 0 |
| 73.5 | 0.284107021 | 0.2 | 0.284107021 | 0.056821404 |
| 73.6 | 0.375968624 | | 0 | 0 |
| 73.7 | 0.47044285 | 0.2 | 0.47044285 | 0.09408857 |
| 73.8 | 0.604680322 | | 0 | 0 |
| 73.9 | 0.713107787 | 0.2 | 0.713107787 | 0.142621557 |
| 74 | 0.871689515 | | 0 | 0 |
| 74.1 | 1.098435523 | 0.2 | 1.098435523 | 0.219687105 |
| 74.2 | 1.367785428 | | 0 | 0 |
| 74.3 | 1.665817869 | 0.2 | 1.665817869 | 0.333163574 |
| 74.4 | 1.899301159 | | 0 | 0 |
| 74.5 | 2.141447675 | 0.2 | 2.141447675 | 0.428289535 |
| 74.6 | 2.383083008 | | 0 | 0 |
| 74.7 | 2.686268902 | 0.2 | 2.686268902 | 0.53725378 |
| 74.8 | 3.074803071 | | 0 | 0 |
| 74.9 | 3.552176613 | 0.2 | 3.552176613 | 0.710435323 |
| 75 | 4.196480555 | | 0 | 0 |
| 75.1 | 5.034814741 | 0.2 | 5.034814741 | 1.006962948 |
| 75.2 | 6.042690372 | | 0 | 0 |
| 75.3 | 7.24113053 | 0.2 | 7.24113053 | 1.448226106 |
| 75.4 | 8.593366692 | | 0 | 0 |
| 75.5 | 10.12652293 | 0.2 | 10.12652293 | 2.025304586 |
| 75.6 | 11.87492594 | | 0 | 0 |

Figure 31

| | | | | |
|---|---|---|---|---|
| 75.7 | 13.80933126 | 0.2 | 13.80933126 | 2.761866252 |
| 75.8 | 16.07307073 | | 0 | 0 |
| 75.9 | 18.63962813 | 0.2 | 18.63962813 | 3.727925625 |
| 76 | 21.59594074 | | 0 | 0 |
| 76.1 | 25.05676145 | 0.2 | 25.05676145 | 5.01135229 |
| 76.2 | 28.97438692 | | 0 | 0 |
| 76.3 | 33.44181929 | 0.2 | 33.44181929 | 6.688363858 |
| 76.4 | 38.23241902 | | 0 | 0 |
| 76.5 | 43.09961431 | 0.2 | 43.09961431 | 8.619922861 |
| 76.6 | 47.78254221 | | 0 | 0 |
| 76.7 | 51.89997569 | 0.2 | 51.89997569 | 10.37999514 |
| 76.8 | 55.45763621 | | 0 | 0 |
| 76.9 | 58.25821372 | 0.2 | 58.25821372 | 11.65164274 |
| 77 | 60.51453236 | | 0 | 0 |
| 77.1 | 62.17478762 | 0.2 | 62.17478762 | 12.43495752 |
| 77.2 | 63.34343153 | | 0 | 0 |
| 77.3 | 64.05235023 | 0.2 | 64.05235023 | 12.81047005 |
| 77.4 | 64.4134976 | | 0 | 0 |
| 77.5 | 64.48588674 | 0.2 | 64.48588674 | 12.89717735 |
| 77.6 | 64.25073369 | | 0 | 0 |
| 77.7 | 63.71199814 | 0.2 | 63.71199814 | 12.74239963 |
| 77.8 | 62.90109574 | | 0 | 0 |
| 77.9 | 61.87099924 | 0.2 | 61.87099924 | 12.37419985 |
| 78 | 60.672542 | | 0 | 0 |
| 78.1 | 59.3146866 | 0.2 | 59.3146866 | 11.86293732 |
| 78.2 | 57.83364287 | | 0 | 0 |
| 78.3 | 56.21447758 | 0.2 | 56.21447758 | 11.24289552 |
| 78.4 | 54.47295324 | | 0 | 0 |
| 78.5 | 52.55214971 | 0.2 | 52.55214971 | 10.51042994 |
| 78.6 | 50.43257729 | | 0 | 0 |
| 78.7 | 47.99231661 | 0.2 | 47.99231661 | 9.598463322 |
| 78.8 | 45.07803906 | | 0 | 0 |
| 78.9 | 41.75423501 | 0.2 | 41.75423501 | 8.350847003 |
| 79 | 37.93598888 | | 0 | 0 |
| 79.1 | 33.72605715 | 0.2 | 33.72605715 | 6.745211431 |
| 79.2 | 29.10505181 | | 0 | 0 |
| 79.3 | 24.41117807 | 0.2 | 24.41117807 | 4.882235614 |
| 79.4 | 19.9080628 | | 0 | 0 |
| 79.5 | 15.7502875 | 0.2 | 15.7502875 | 3.150057501 |
| 79.6 | 12.05914865 | | 0 | 0 |
| 79.7 | 8.900892722 | 0.2 | 8.900892722 | 1.780178544 |
| 79.8 | 6.376360937 | | 0 | 0 |
| 79.9 | 4.449535636 | 0.2 | 4.449535636 | 0.889907127 |
| 80 | 3.058138865 | | 0 | 0 |
| 80.1 | 2.062045358 | 0.2 | 2.062045358 | 0.412409072 |
| 80.2 | 1.35411666 | | 0 | 0 |
| 80.3 | 0.863027703 | 0.2 | 0.863027703 | 0.172605541 |
| 80.4 | 0.531051296 | | 0 | 0 |
| 80.5 | 0.316805827 | 0.2 | 0.316805827 | 0.063361165 |
| 80.6 | 0.173765577 | | 0 | 0 |

Figure 31 continued

| | | | | |
|---|---|---|---|---|
| 80.7 | 0.08794406 | 0.2 | 0.08794406 | 0.017588812 |
| 80.8 | 0.034708737 | | 0 | 0 |
| 80.9 | -0.004509008 | 0.2 | -0.004509008 | -0.000901802 |
| 81 | -0.037939015 | | 0 | 0 |
| 81.1 | -0.062069426 | 0.2 | -0.062069426 | -0.012413885 |
| 81.2 | -0.074046791 | | 0 | 0 |
| 81.3 | -0.07850802 | 0.2 | -0.07850802 | -0.015701604 |
| 81.4 | -0.08252329 | | 0 | 0 |
| 81.5 | -0.089334948 | 0.2 | -0.089334948 | -0.01786699 |
| 81.6 | -0.094453676 | | 0 | 0 |
| 81.7 | -0.097882055 | 0.2 | -0.097882055 | -0.019576411 |
| 81.8 | -0.095970581 | | 0 | 0 |
| 81.9 | -0.094964577 | 0.2 | -0.094964577 | -0.018992915 |
| 82 | -0.096849601 | | 0 | 0 |
| 82.1 | -0.098704701 | 0.2 | -0.098704701 | -0.01974094 |
| 82.2 | -0.095381238 | | 0 | 0 |
| 82.3 | -0.092295606 | 0.2 | -0.092295606 | -0.018459121 |
| 82.4 | -0.088300915 | | 0 | 0 |
| 82.5 | -0.089347665 | 0.2 | -0.089347665 | -0.017869533 |
| 82.6 | -0.087331332 | | 0 | 0 |
| 82.7 | -0.088332977 | 0.2 | -0.088332977 | -0.017666595 |
| 82.8 | -0.084705956 | | 0 | 0 |
| 82.9 | -0.082965496 | 0.2 | -0.082965496 | -0.016593099 |
| 83 | -0.08099924 | | 0 | 0 |
| 83.1 | -0.079720479 | 0.2 | -0.079720479 | -0.015944096 |
| 83.2 | -0.07718121 | | 0 | 0 |
| 83.3 | -0.075096232 | 0.2 | -0.075096232 | -0.015019246 |
| 83.4 | -0.076612391 | | 0 | 0 |
| 83.5 | -0.076922698 | 0.2 | -0.076922698 | -0.01538454 |
| 83.6 | -0.074180829 | | 0 | 0 |
| 83.7 | -0.068612199 | 0.2 | -0.068612199 | -0.01372244 |
| 83.8 | -0.066726338 | | 0 | 0 |
| 83.9 | -0.064377553 | 0.2 | -0.064377553 | -0.012875511 |
| 84 | -0.063897764 | | 0 | 0 |
| 84.1 | -0.05724271 | 0.2 | -0.05724271 | -0.011448542 |
| 84.2 | -0.054996169 | | 0 | 0 |
| 84.3 | -0.050497778 | 0.2 | -0.050497778 | -0.010099556 |
| 84.4 | -0.053016494 | | 0 | 0 |
| 84.5 | -0.050630714 | 0.2 | -0.050630714 | -0.010126143 |
| 84.6 | -0.047100898 | | 0 | 0 |
| 84.7 | -0.044208207 | 0.2 | -0.044208207 | -0.008841641 |
| 84.8 | -0.041591851 | | 0 | 0 |
| 84.9 | -0.03942342 | 0.2 | -0.03942342 | -0.007884684 |
| 85 | -0.034633706 | | 0 | 0 |
| 85.1 | -0.03438053 | 0.2 | -0.03438053 | -0.006876106 |
| 85.2 | -0.040385093 | | 0 | 0 |
| 85.3 | -0.039134497 | 0.2 | -0.039134497 | -0.007826899 |
| 85.4 | -0.039034932 | | 0 | 0 |
| 85.5 | -0.035764111 | 0.2 | -0.035764111 | -0.007152822 |
| 85.6 | -0.036538532 | | 0 | 0 |

Figure 31 continued

| | | | | |
|---|---|---|---|---|
| 85.7 | -0.032606954 | 0.2 | -0.032606954 | -0.006521391 |
| 85.8 | -0.035180357 | | 0 | 0 |
| 85.9 | -0.03230282 | 0.2 | -0.03230282 | -0.006460564 |
| 86 | -0.029824248 | | 0 | 0 |
| 86.1 | -0.025357127 | 0.2 | -0.025357127 | -0.005071425 |
| 86.2 | -0.02509683 | | 0 | 0 |
| 86.3 | -0.022431608 | 0.2 | -0.022431608 | -0.004486322 |
| 86.4 | -0.019027963 | | 0 | 0 |
| 86.5 | -0.015428402 | 0.2 | -0.015428402 | -0.00308568 |
| 86.6 | -0.015780963 | | 0 | 0 |
| 86.7 | -0.015489869 | 0.2 | -0.015489869 | -0.003097974 |
| 86.8 | -0.01670578 | | 0 | 0 |
| 86.9 | -0.019976797 | 0.2 | -0.019976797 | -0.003995359 |
| 87 | -0.019441184 | | 0 | 0 |
| 87.1 | -0.015074018 | 0.2 | -0.015074018 | 19.94555756 |
| 87.2 | -0.014029472 | | 0 | 0 |
| 87.3 | -0.011735197 | 0.2 | -0.011735197 | 19.68499629 |
| 87.4 | -0.016884147 | | 0 | 0 |
| 87.5 | -0.016782268 | 0.2 | -0.016782268 | 19.44108485 |
| 87.6 | -0.018820007 | | 0 | 0 |
| 87.7 | -0.01708046 | 0.2 | -0.01708046 | 19.20296713 |
| 87.8 | -0.013073874 | | 0 | 0 |
| 87.9 | -0.010939956 | 0.2 | -0.010939956 | 18.97261571 |
| 88 | -0.006895695 | | 0 | 0 |
| 88.1 | -0.003441937 | 0.2 | -0.003441937 | 18.71601366 |
| 88.2 | -0.000650118 | | 0 | 0 |
| 88.3 | 0.002364956 | 0.2 | 0.002364956 | 18.47889667 |
| 88.4 | 0.001041691 | | 0 | 0 |
| 88.5 | -0.000694267 | 0.2 | -0.000694267 | 18.25842113 |
| 88.6 | -0.002929403 | | 0 | 0 |
| 88.7 | 0.003314093 | 0.2 | 0.003314093 | 18.02628081 |
| 88.8 | 0.005745978 | | 0 | 0 |
| 88.9 | 0.007635306 | 0.2 | 0.007635306 | 17.78698564 |
| 89 | 0.003652418 | | 0 | 0 |
| | | | | |
| | | | | 375.9785963 |
| | | | | Sum above = AUC |

Figure 31 continued

METHODS FOR MOLECULARLY CHARACTERIZING CERVICAL CELL SAMPLES

ACKNOWLEDGEMENT OF GOVERNMENT SUPPORT

This invention was made by employees of the United States Army Medical Research and Materiel Command, which is an agency of the United States Government. The Government has certain rights in the invention.

REFERENCE TO A SEQUENCE LISTING SUBMITTED VIA EFS-WEB

The content of the ASCII text file of the sequence listing named "20160830_034047_062WO1_seq_ST25" which is 4.38 kb in size was created on Aug. 30, 2016 and electronically submitted via EFS-Web herewith the application is incorporated herein by reference in its entirety.

BACKGROUND OF THE INVENTION

1. Field of the Invention

The present invention relates to methods for characterizing a cervical tissue sample as being: negative for intraepithelial lesion or malignancy (NILM), low-grade squamous intraepithelial lesion (LSIL), or high-grade squamous intraepithelial lesion (HSIL).

2. Description of the Related Art

In 1941, George Papanicolaou published his landmark paper on the use of vaginal smears for the diagnosis of cervical cancer (Reference 1). The road to his discovery and popularization of the Papanicolaou (Pap) smear was a four decade long, arduous journey starting with experimentation on guinea pigs then women attending the clinic of Cornell Medical College (Reference 2). Since the development and systemization of cytomorphology for cancer detection by Papanicolaou in 1948, the Pap smear has remained the foundation for cervical cancer screening worldwide. Today, however, low-resource countries continue to lack the infrastructure to sustain a cytology-based screening program, i.e., rapid transport of smears, quality laboratory services, and trained cytopathologists. With about 528,000 new cases worldwide each year, the highest incidence rates of cervical cancer remain in the unscreened, resource-limited regions of Africa, Latin America, Southeast Asia, and the Western Pacific (Reference 3).

Since the isolation and cloning of HPV-16 from cervical carcinoma by zur Hausen et al. in 1983, the human papillomavirus (HPV) is now recognized as a necessary cause of invasive cervical cancer with a prevalence of 99% in global samples (References 4, 5). With advancements in molecular diagnostics and automation, primary high-risk HPV (hrHPV) cervical screening and alternative strategies, such as Visual Inspection with Acetic acid (VIA) that supplant the resource-demanding cytology-based model, have risen to the forefront. Both screening strategies are now incorporated into the 2014 World Health Organization (WHO) published guidance on cervical cancer (Reference 3). The Cobas® hrHPV test, recently approved by the U.S. Food and Drug Administration (FDA) for primary screening, is a qualitative PCR assay that amplifies a 200 bp segment of the HPV L1 capsid gene which detects HPV types 16 and 18 and/or the other 12 high risk types (Reference 6). However, this test is limited by the nonspecific detection of non-16/18 hrHPV types and non-detection of possibly carcinogenic and not classifiable types defined by the International Agency for Research on Cancer (IARC) (References 7, 8). The true value in full spectrum HPV genotype identification is the revelation of its virulence, pathogenicity, and carcinogenicity which guides clinicians in selecting the appropriate therapy, i.e., observation or ablative therapy.

Over the last two decades, our understanding of cancer epigenetics has deepened immensely (Reference 9). The body of literature investigating aberrant DNA methylation in cervical carcinoma and its contribution to carcinogenesis via silencing of tumor suppressor genes continues to grow (References 10-15). However, DNA methylation studies of abnormal cervical cytology are sparse and none has incorporated HPV genotype beyond high-risk types as a predictive marker (References 16, 17).

SUMMARY OF THE INVENTION

In some embodiments, the present invention provides a method of determining the methylation level of one or more CpG sites of a nucleic acid molecule obtained from a cervical cell sample, which comprises converting unmethylated cytosine residues of the nucleic acid molecule to uracil by contacting the nucleic acid molecule with bisulfite to obtain a bisulfite converted nucleic acid molecule; subjecting the bisulfite converted nucleic acid molecule to polymerase chain reaction amplification using a set of primers to obtain amplified nucleic acid molecules; and determining the methylation level of the one or more CpG sites, wherein said nucleic acid molecule has a sequence identity of at least 95% to SEQ ID NO: 1, SEQ ID NO: 2, SEQ ID NO: 3, or SEQ ID NO: 4. In some embodiments, the polymerase chain reaction amplification is real-time polymerase chain reaction amplification. In some embodiments, the nucleic acid molecule has a sequence identity of at least 95% to SEQ ID NO: 1, and the set of primers are SEQ ID NO: 12 and SEQ ID NO: 13. In some embodiments, the nucleic acid molecule has a sequence identity of at least 95% to SEQ ID NO: 4, and the set of primers are SEQ ID NO: 15 and SEQ ID NO: 16. In some embodiments, the step of determining the methylation level is performed by high resolution melt analysis. In some embodiments, the step of determining the methylation level is performed by pyrosequencing. In some embodiments, the overall methylation level of all the CpG sites of SEQ ID NO: 1, SEQ ID NO: 2, SEQ ID NO: 3, and/or SEQ ID NO: 4 are determined by high resolution melt analysis. In some embodiments, the methylation level of one or more individual CpG sites of SEQ ID NO: 1, SEQ ID NO: 2, SEQ ID NO: 3, and/or SEQ ID NO: 4 are determined by pyrosequencing.

In some embodiments, the present invention provides a method of characterizing a cervical cell sample as being normal or abnormal, which comprises a) determining the HPV genotype of cell sample; and/or b) quantifying the methylation level of the CpG 3 of ZNF582 (SEQ ID NO: 3); c) characterizing the cervical cell sample as being abnormal where the HPV genotype is selected from the group consisting of: 114, 91, 90, 84, 83, 81, 72, 71, 61, 54, 43, 42, 11, 6, 97, 85, 82, 73, 70, 69, 67, 66, 53, 34, 30, 26, a9, 68, 59, 58, 56, 52, 51, 45, 39, 35, 33, 31, 18, and 16 and/or the quantified methylation level is equal to or greater than 1.1; and d) characterizing the cervical cell sample as being normal where the criteria set forth in step c) are not met. In some embodiments, both steps a) and b) are performed and the cervical cell sample is characterized as being abnormal where the HPV genotype is selected from the group consisting of: 114, 91, 90, 84, 83, 81, 72, 71, 61, 54, 43, 42, 11, 6, 97, 85, 82, 73, 70, 69, 67, 66, 53, 34, 30, 26, a9, 68, 59, 58, 56, 52, 51, 45, 39, 35, 33, 31, 18, and 16 and the quantified methylation level is equal to or greater than 1.1. In some embodiments, the HPV genotype is 97, 85, 82, 73, 70, 69, 67, 66, 53, 34, 30, 26, a9, 68, 59, 58, 56, 52, 51, 45, 39, 35, 33, 31, 18, or 16. In some embodiments, the HPV genotype is a9, 68, 59, 58, 56, 52, 51, 45, 39, 35, 33, 31, 18, or 16. In some embodiments, a finding that the cervical cell sample is abnormal means the cervical cell sample is a low-grade squamous intraepithelial lesion (LSIL) or a high-grade squamous intraepithelial lesion (HSIL).

In some embodiments, the present invention provides a method of characterizing a cervical cell sample as being a high-grade squamous intraepithelial lesion (HSIL), which comprises a) determining the HPV genotype of cell sample; b) quantifying the methylation level of at least two of the following CpG sites: CpG 7 of ADCY8 (SEQ ID NO: 1), CpG 3 of CDH8 (SEQ ID NO: 2), and CpG 3 of ZNF582 (SEQ ID NO: 3); c) characterizing the cervical cell sample as being abnormal where: i) the HPV genotype is selected from the group consisting of: 97, 85, 82, 73, 70, 69, 67, 66, 53, 34, 30, 26, a9, 68, 59, 58, 56, 52, 51, 45, 39, 35, 33, 31, 18, and 16; and the quantified methylation level of CpG 7 of ADCY8 is equal to or greater than 5.8; the quantified methylation level of CpG 3 of CDH8 is equal to or greater than 3.0; and the quantified methylation level of CpG 3 of ZNF582 is equal to or greater than 1.1; or ii) the HPV genotype is selected from the group consisting of: a9, 68, 59, 58, 56, 52, 51, 45, 39, 35, 33, 31, 18, and 16; and the quantified methylation level of CpG 7 of ADCY8 is equal to or greater than 5.8, the quantified methylation level of CpG 3 of CDH8 is equal to or greater than 3.0, the quantified methylation level of CpG 3 of ZNF582 is equal to or greater than 1.1, or a combination or two or more; and d) characterizing the cervical cell sample as being normal or low-grade squamous intraepithelial lesion (LSIL) where the criteria set forth in step c) are not met.

In some embodiments, the present invention provides a method of characterizing a cervical cell sample as being high-grade squamous intraepithelial lesion (HSIL), which comprises a) subjecting the sample to PCR amplification using the following primer set: FAP59 (SEQ ID NO: 7) and FAP64 (SEQ ID NO: 8); b) determining the presence or absence of about a 260 bp amplicon that maps to nucleotides 6047 to about 6250-6254 of HPV 58; and c) characterizing the cervical sample as being HSIL where the 260 bp amplicon is detected.

In some embodiments, the present invention provides a method of characterizing a cervical cell sample as being normal or abnormal, which comprises a) determining the HPV genotype of cell sample; b) using multivariable logistic regression to determine the association between the methylation levels of two or more CpG sites determined to be hypermethylated by at least 2× that of normal cytology samples a binarized cytological outcome of interest; and c) using the following logistic regression model:

$$\text{Probability of outcome} = P(Y=1) = \frac{1}{1+e^{-(b_0+b_1X_1+\ldots+b_iX_i)}},$$

where $X_1, \ldots, X_i$ (where $X_i$=Gene X and CpG position i methylation level (%)), and (Y) coding=normal (0), abnormal (1); c) characterizing the cervical cell sample as being abnormal where the calculated probability exceeds a statistically determined cut-off value and characterizing the cervical cell sample as being normal where the calculated probability does not exceed the statistically determined cut-off value.

In some embodiments, the present invention provides a method of characterizing a cervical cell sample as being negative for intraepithelial lesion or malignancy (NILM) or low-grade squamous intraepithelial lesion (LSIL) versus high-grade squamous intraepithelial lesion (HSIL), which comprises a) determining the HPV genotype of cell sample; b) using multivariable logistic regression to determine the association between the methylation levels of two or more CpG sites determined to be hypermethylated by at least 2× that of normal cytology samples a binarized cytological outcome of interest; and c) using the following logistic regression model:

$$\text{Probability of outcome} = P(Y=1) = \frac{1}{1+e^{-(b_0+b_1X_1+\ldots+b_iX_i)}},$$

where $X_1, \ldots, X_i$ (where $X_i$=Gene X and CpG-position i methylation level (%)), and (Y) coding=NILM or LSIL (0), HSIL (1); d) characterizing the cervical cell sample as being HSIL where the calculated probability exceeds a statistically determined cut-off value and characterizing the cervical cell sample as being NILM or LSIL where the calculated probability does not exceed the statistically determined cut-off value.

In any one of the embodiments of the present invention, the CpG sites that are analyzed for methylation are selected from one or more of the following groups consisting of CpG 1, CpG 2, CpG 3, CpG 4, CpG 5, CpG 6, CpG 7, and CpG 8 of SEQ ID NO: 1; CpG 1, CpG 2, CpG 3, CpG 4, and CpG 5 of SEQ ID NO: 2; CpG 1, CpG 2, CpG 3, CpG 4, and CpG 5 of SEQ ID NO: 3; and CpG 1, CpG 2, CpG 3, CpG 4, CpG 5, CpG 6, CpG 7, CpG 8, CpG 9, CpG 10, CpG 11, and CpG 12 of SEQ ID NO: 4. In any one of the embodiments of the present invention, the CpG sites that are analyzed for methylation comprise or consist of one or more of the following CpG sites: CpG 7 of SEQ ID NO: 1, CpG 3 of SEQ ID NO: 2, CpG 3 of SEQ ID NO: 3, and CpG 5 of SEQ ID NO: 4.

In any one of the embodiments of the present invention, CpG site methylation is determined by methylation-sensitive high resolution melting analysis. In some embodiments, the methylation level of one or more CpG sites is determined by extrapolating from a best-fit regression line or curve (polynomial) constructed from a fluorescence difference plot versus temperature using a standardized plot. Suitable known standardized plots include best-fit regression lines or curves (polynomial) obtained from a set of bisulfite-converted, methylated standards with known fractions of methylation, e.g., 0%, 20%, 40%, 60%, and 100%, and the Midpoint Riemann Sum formula for approximating the area-under-the-curve (AUC) of the fluorescence difference plot versus temperature. The Midpoint Riemann Sum may be calculated by 1) dividing the interval along the x-axis into segments, 2) finding the midpoint of the segments, 3) multiplying the function of x or f(x) at the midpoints by the interval length, and 4) adding the areas of each segment to calculate the area-under-the-curve (AUC). The best-fit regression line or curve (polynomial) is generated from the regression plot of the methylation (%) of each standard (x-axis) and the AUC (y-axis).

In some embodiments, the present invention provides a kit comprising at least one set of pyrosequencing primers for SEQ ID NO: 1, SEQ ID NO: 2, SEQ ID NO: 3, and/or SEQ ID NO: 4; and a primer set for obtaining PCR amplicons that map to nucleotides 6041 to 6253 of HPV 58 complete genome (D90400.1; GI: 222386) packaged together. In some embodiments, the kits include reagents for performing PCR. In some embodiments, the kits include instructions for assaying the methylation of one or more CpG sites of SEQ ID NO: 1, SEQ ID NO: 2, SEQ ID NO: 3, and/or SEQ ID NO: 4. In some embodiments, the kits include one or more standardized plots for analyzing the methylation of one or more CpG sites of SEQ ID NO: 1, SEQ ID NO: 2, SEQ ID NO: 3, and/or SEQ ID NO: 4.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1 shows the clinical and cytological characteristics of the study population. IQR=interquartile range; LBC=Liquid-based Cytology; LSIL=low-grade squamous intraepithelial lesion; HSIL=high-grade squamous intraepithelial lesion; NILM=negative for intraepithelial lesion and malignancy.

FIG. 3 are Venn diagrams showing intersecting and complementary sets of cytological samples (N) detected of HPV DNA by MY-, FAP-, and E6/E7 primer sets according to cytological diagnoses, i.e., NILM, LSIL, and HSIL. The net positivity of simultaneous testing for HPV (union of the circles) in NILM, LSIL, and HSIL are 31/100 (31%), 95/100 (95%), and 71/77 (92%), respectively. AM=Alignment marker, B=buffer, bp=base pair, M=molecular weight ladder.

FIG. 12 are bar graphs presenting the median DNA methylation ($\beta$ value) of 257 tumors, and 3 matched tumor/ normal samples across the ordered CpG probes. For each set of bars, the order from left to right is Normal matched, Tumor matched, and Tumor. The promoter methylation levels were notably higher (about 10×) for tumor (median β about 0.6) than the normal samples (median β about 0.06) for ADCY8, CDH8, and ZNF582. The enhancer/promoter and gene body regions are indicated by the first arrow and second arrow, respectively. The CpG region selected for bisulfite pyrosequencing of cytology samples are denoted by the underscored CpG probes. The chromosome coordinates for the CpG probes along the X-axis are: ADCY8 (chr8: 132,053,823-131,896,788), CDH8 (chr16: 62,070,072-61,871,849), ZNF582 (chr19: 56,905,383-56,901,457) and MGMT (chr10: 131,264,840-131,304,833). The GRCh37 coordinates are provided by the HM450K assay (Illumina). Chromosome ideograms adapted from NCBI Map Viewer (WorldWideWeb.ncbi.nlm.nihDOTgov/genome/guide/human, wherein "WorldWideWeb" is "www" and "DOT" is ".").

FIG. 13 is a table providing the variables for logistic regression analysis of HPV and HPV+ZNF582 for predicting abnormal (LSIL/HSIL) cytology.

FIG. 14 is a table providing the variables for logistic regression analysis of HPV and HPV+3-gene methylation markers for predicting for HSIL cytology.

FIG. 15 are graphs generated by receiver operating characteristic curve analysis using cutpoints derived from univariate ROC analysis of gene-specific methylation levels. Multivariable modeling revealed the best predictor to differentiate between NILM and LSIL/HSIL was HPV carcinogenicity and ZNF582 7th CpG position binarized as follows: <1.1 (0), ≥1.1 (1) (ROC AUC=0.93). For differentiating between NILM/LSIL and HSIL cytology, the best multivariate predictor was the combination of HPV carcinogenicity, CpG 7 of ADCY8, CpG3 of CDH8, and CpG 3 of ZNF582 (ROC AUC=0.89); the binarized methylation levels (%) used for the respective 3 genes were: <5.8 (0), ≥5.8; <3.0 (0), ≥3.0 (1); <1.1 (0), ≥1.1 (1). In the graphs, the middle line is HPV. *, P<0.05 by the chi-square test and Delta method for pairwise comparison of margins. ROC, Receiver operating characteristic; AUC, area under the curve.

Figure 16:
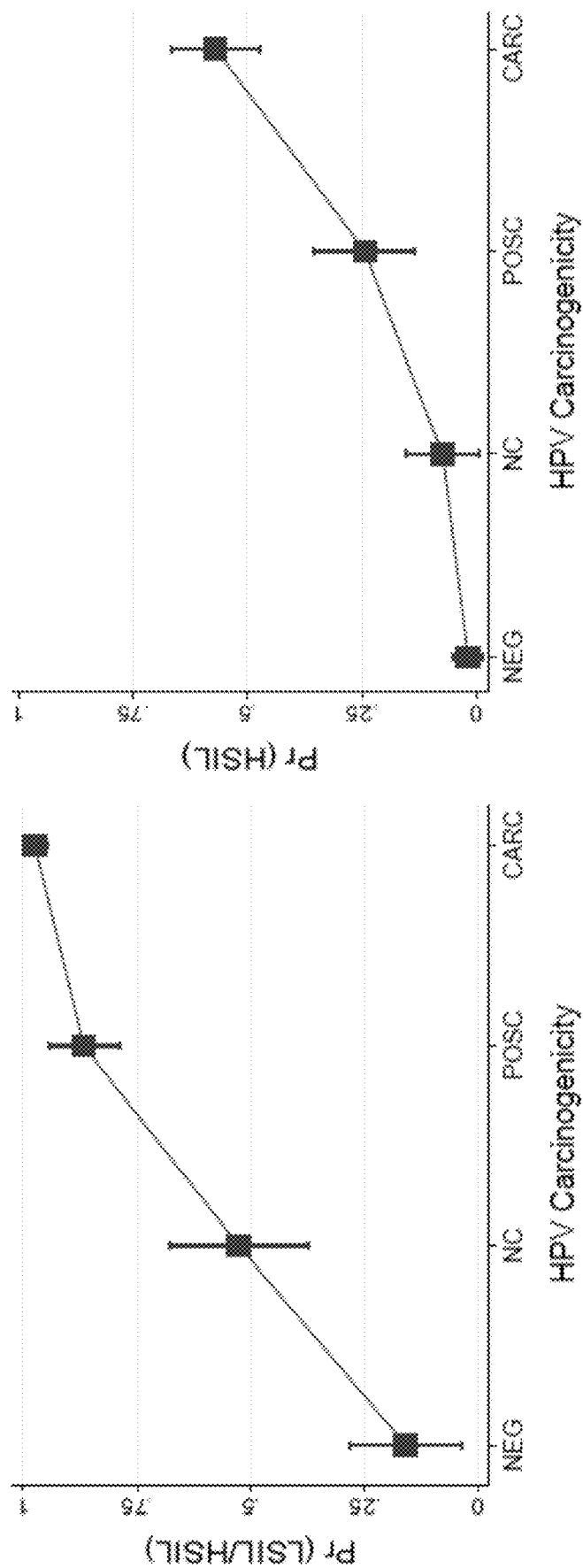

FIG. 16 are graphs showing the predicted probabilities plots of binarized cytology grades (NILM vs. LSIL/HSIL and NILM/LSIL vs. HSIL) using HPV carcinogenicity as the single predictor variable.

Figure 17:
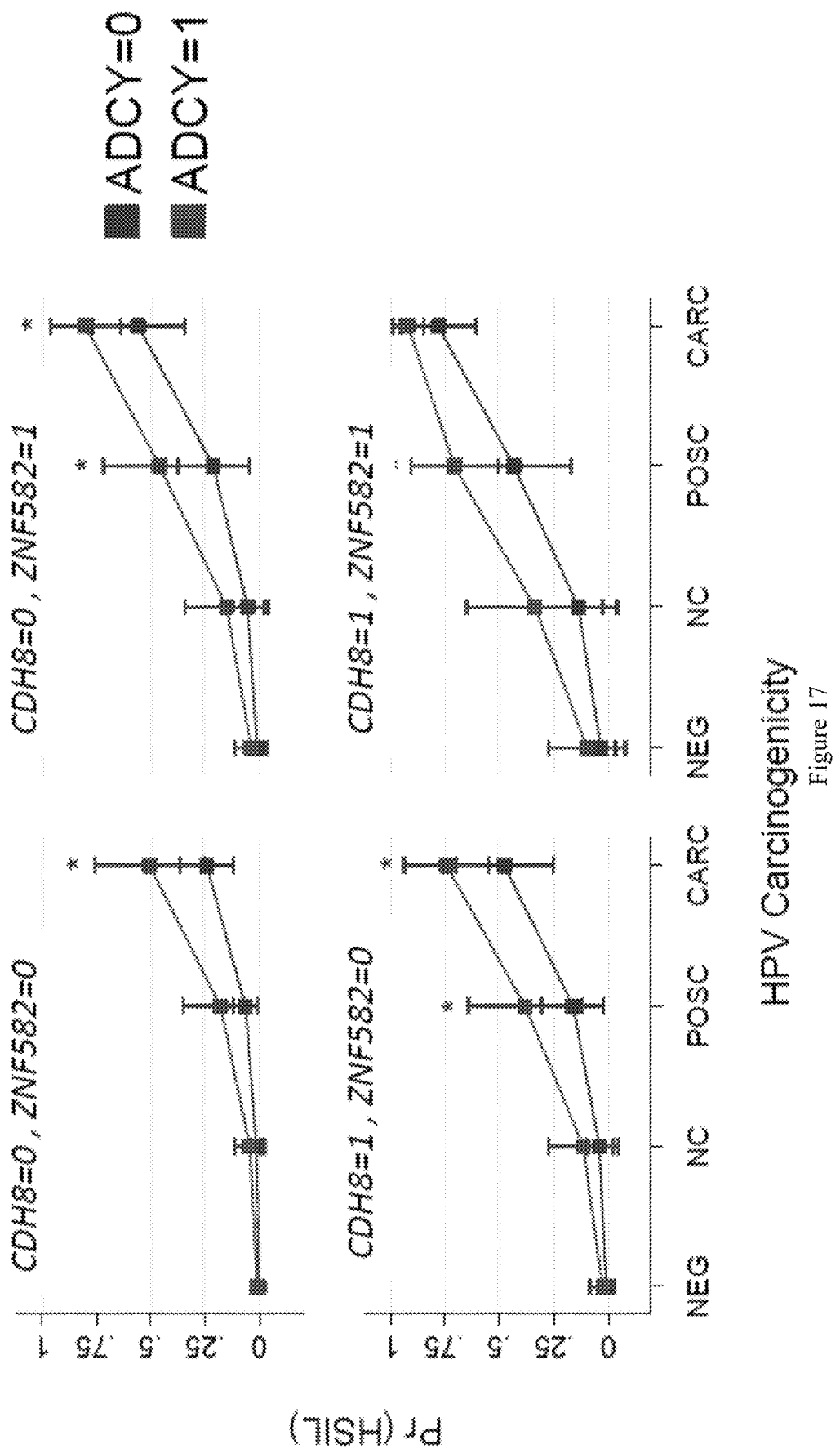

FIG. 17 are graphs comparing the predicted probabilities for HSIL (NILM/LSIL vs. HSIL) permuted by binarized methylation levels of CpG 7 of ADCY8, CpG 3 of CDH8, and CpG 3 of ZNF582. The 4 graphs illustrate the escalating probability for HSIL coincident with the increasing number of methylated genes. In the graphs, the bottom line is ADCY=0. *, P<0.05 by the chi-square test and Delta method for pairwise comparison of margins.

Figure 18:
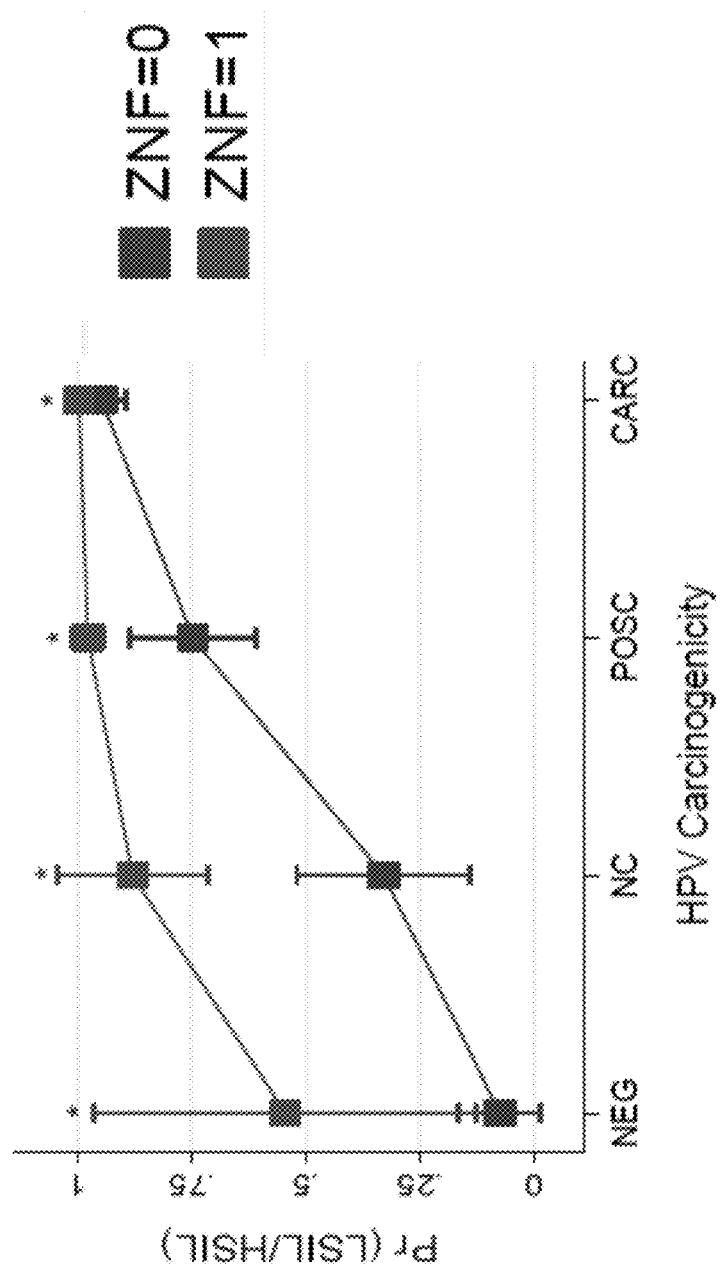

FIG. 18 is a graph comparing the predicted probabilities for abnormal cytology (NILM vs. LSIL/HSIL) by HPV carcinogenicity and binarized ZNF582 methylation level coded as <1.1 (0) or ≥1.1 (1). In the graph, the bottom line is ZNF=0.

FIG. 19 is a table providing the predictive margins for abnormal (LSIL/HSIL) cytology based on HPV or HPV+ZNF582.

FIG. 20 is a table providing the predictive margins for HSIL cytology based on HPV or HPV+3-gene methylation markers. The margins (in bold) are the positive outcome or "classification threshold" probabilities used for classification of outcomes and the evaluation of diagnostic test performance. The classification threshold was estimated by using the maximum sum of sensitivity and specificity (Youden's index).

FIG. 21 is a table providing the diagnostic performance of HPV vs. HPV+ZNF582 for abnormal (LSIL/HSIL) cytology.

FIG. 22 is a table providing the diagnostic performance of HPV vs. HPV+3-gene methylation markers for HSIL cytology.

FIG. 23 is a table providing the variables for logistic regression analysis of HPV and HPV+ALK for predicting abnormal (HSIL) cytology.

Figure 24:
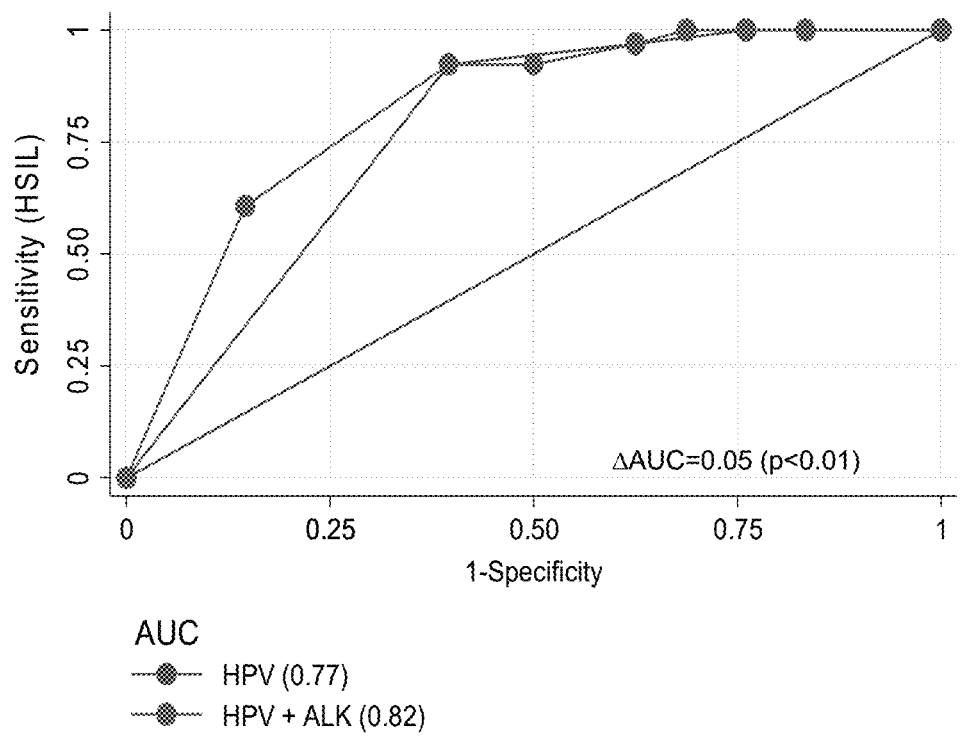

FIG. 24 is a graph generated by receiver operating characteristic curve analysis using cut points derived from univariate ROC analysis of gene-specific methylation levels. Multivariable modeling revealed the better predictor to differentiate between NILM/LSIL and HSIL was HPV carcinogenicity and ALK. 5th CpG position binarized as follows: <1.0 (0), ≥1.0 (1) (ROC AUC=0.82). ROC, Receiver operating characteristic; AUC, area under the curve.

Figure 25:
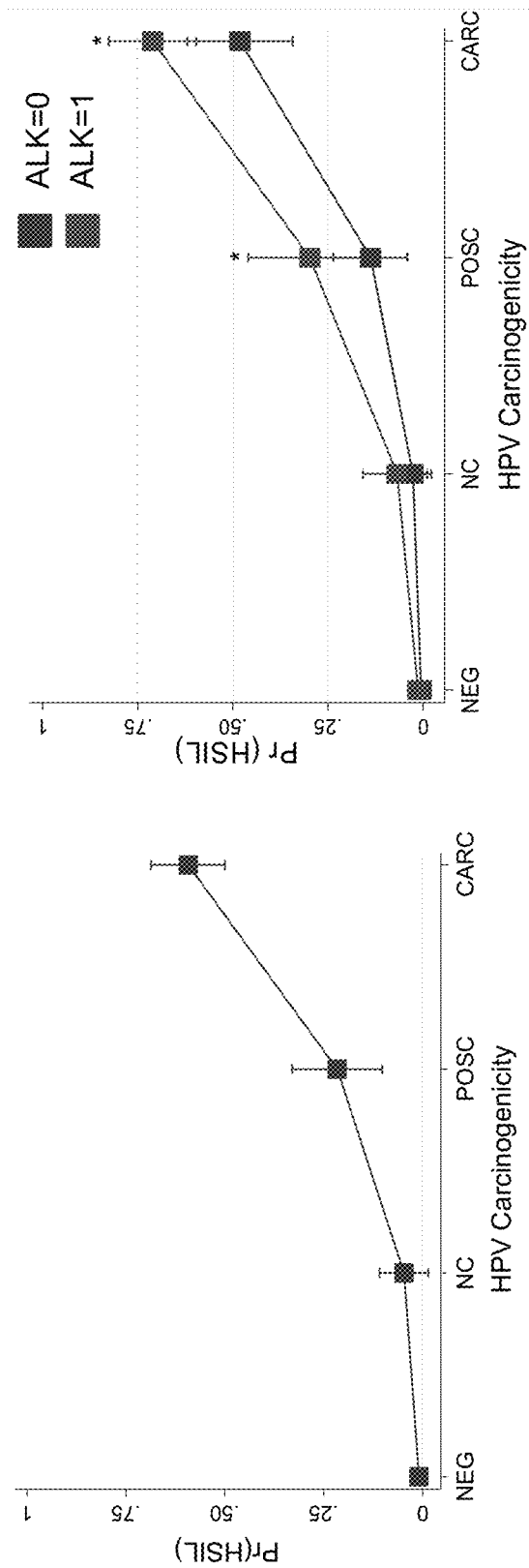

FIG. 25 are predicted probabilities plots based on HPV or HPV and ALK as predictors. Predicted probabilities plot of binarized cytology grades (NILM/LSIL vs. HSIL) illustrates the segregating effect of ALK over HPV carcinogenicity alone as a predictor of HSIL.

FIG. 26 is a table summarizing the predicted probabilities for HSIL (NILM/LSIL vs. HSIL) permuted by binarized methylation levels of ALK. This panel illustrate the escalating probability for HSIL coincident with the methylation of ALK. *, P<0.05 by the chi-square test and Delta method for pairwise comparison of margins.

Figure 27:
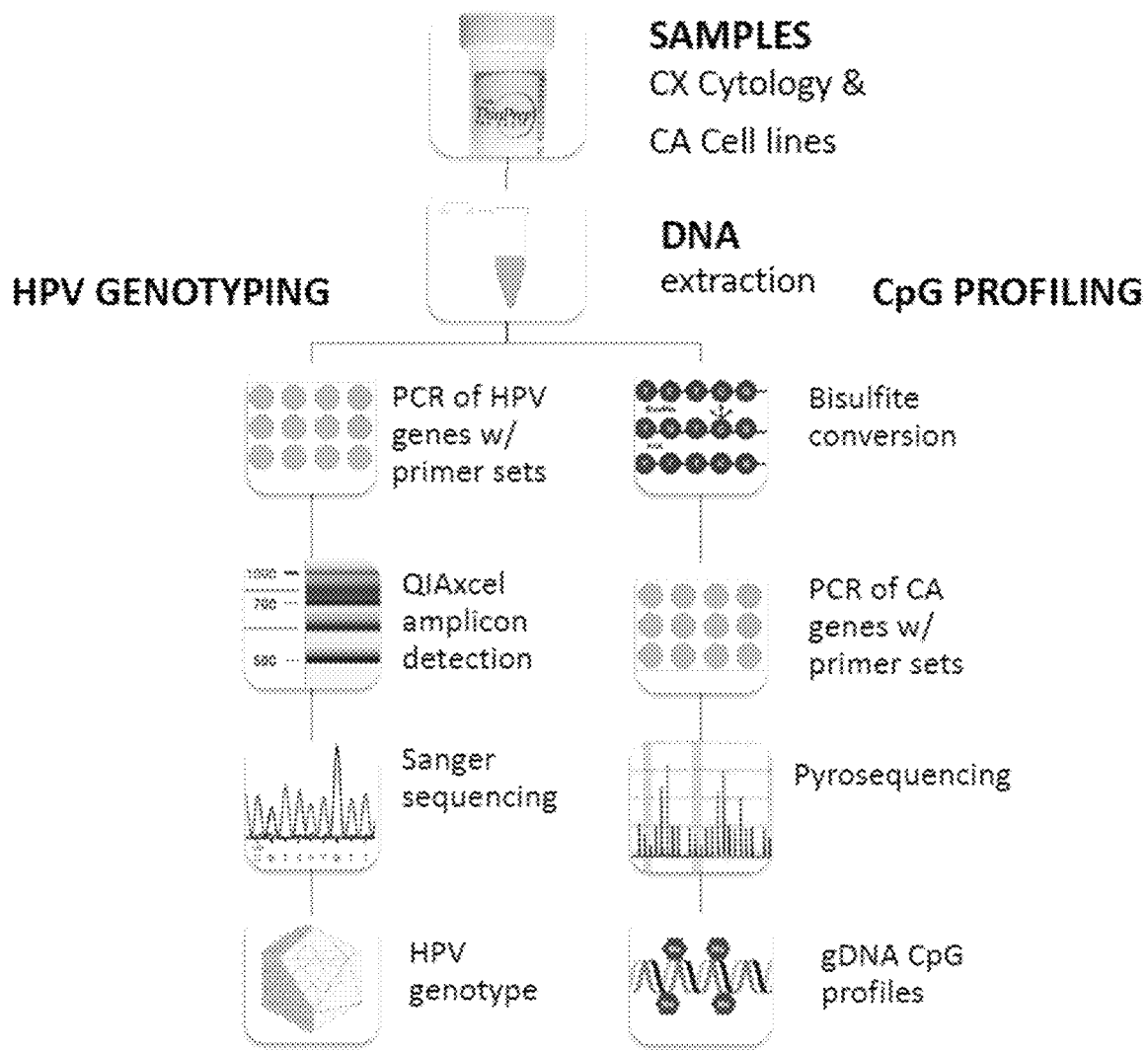

FIG. 27 schematically shows the protocol schema: Sample collection, DNA extraction, HPV genotyping by Sanger sequencing, and CpG profiling of gene-specific promoters by pyrosequencing.

Figure 28:
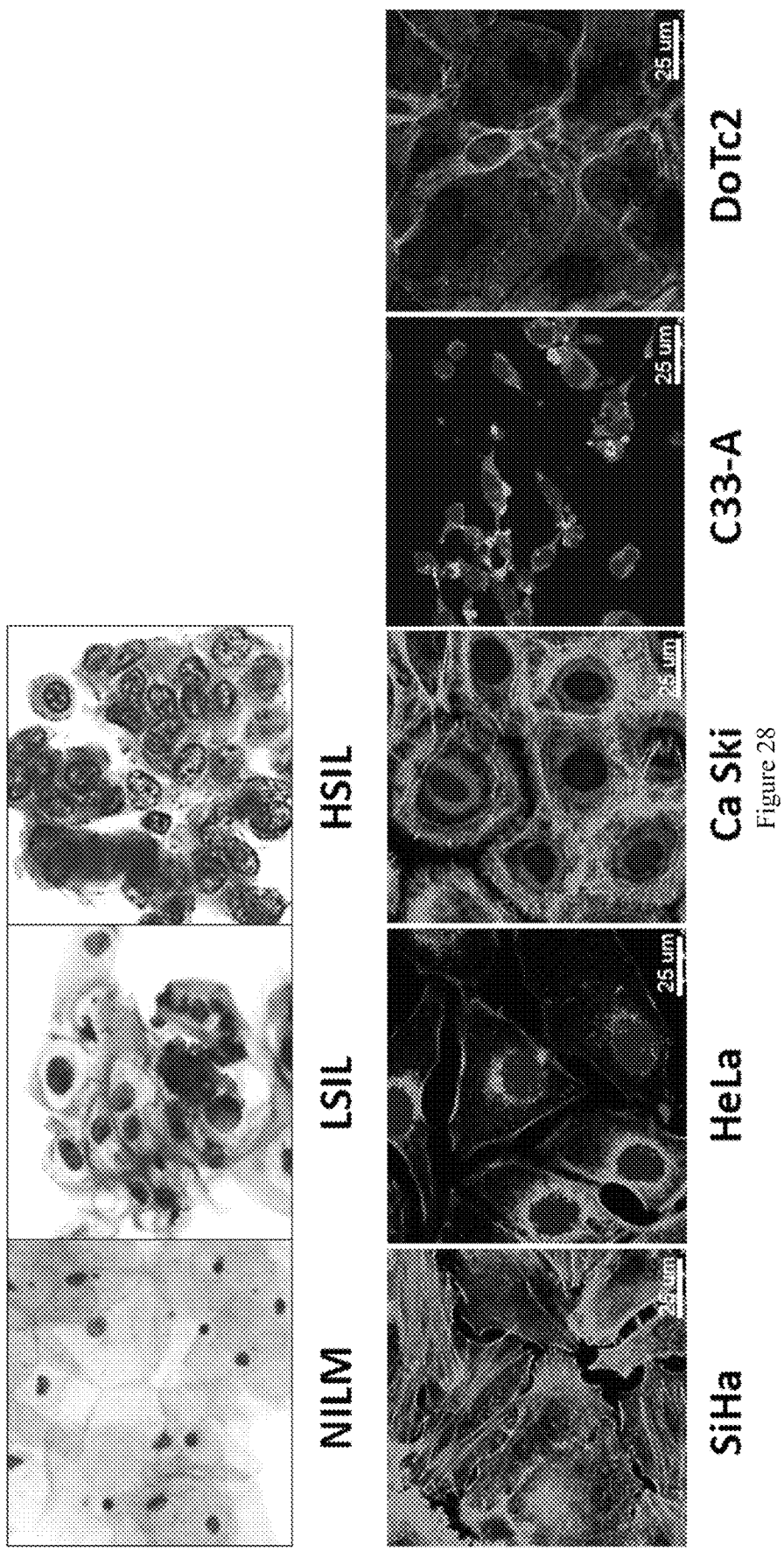

FIG. 28 are representative images of cervical cytology and cervical carcinoma cell lines used in the experiments herein. Three categories of liquid-based cervical cytology: negative for intraepithelial lesion or malignancy (NILM), low-grade squamous intraepithelial lesion (LSIL), and high-grade squamous intraepithelial lesion (HSIL) reveal progressive nuclear enlargement, nuclear membrane irregularity, and chromatin coarseness associated with worsening grade. Five cervical carcinoma cell lines: SiHa, HeLa, Ca Ski, C33-A, and DoTc2 with distinct cytomorphologic features, e.g., cell size and shape, nucleus, nuclear/cytoplasmic ratio, chromatin patterns, actin cytoskeleton, and mitochondria. Each cell line was immunofluorescence labeled and imaged by confocal microscopy (63× objective).

FIG. 29 is a table setting forth the primers used for the gene promoters for ADCY8 (sequences from top to bottom are SEQ ID NO: 12, SEQ ID NO: 13, and SEQ ID NO: 14), CDH8, MGMT, ZNF582, and ALK (sequences from top to bottom are SEQ ID NO: 15, SEQ ID NO: 16, and SEQ ID NO: 17).

FIG. 30 are tables showing the locations of the CpG sites of ADCY8, CDH8, MGMT, and ZNF582 assayed based on the NCBI 36/hg 18 Assembly (Human Genome version 18, GCF_000001405.12).

FIG. 31 depicts the use of the Midpoint Riemann Sum formula for calculation of the area-under-the-curve (AUC) of the fluorescence difference plot versus temperature for standards and controls. The table lists the mean fluorescence value from 71° C. to 89° C. for a representative, bisulfate-converted, methylated standard (100%) after high-resolution melting analysis. The table also lists the following variables: 1) temperature interval, 2) fluorescence value at the midpoint of the intervals, and 3) temperature interval multiplied by the fluorescence value at the midpoint, to calculate the AUC. The AUC's of a known set of methylated standards are then used to construct normalized melting curves that may be used as standards to determine the methylation level of the CpGs of test samples.

Figure 32:
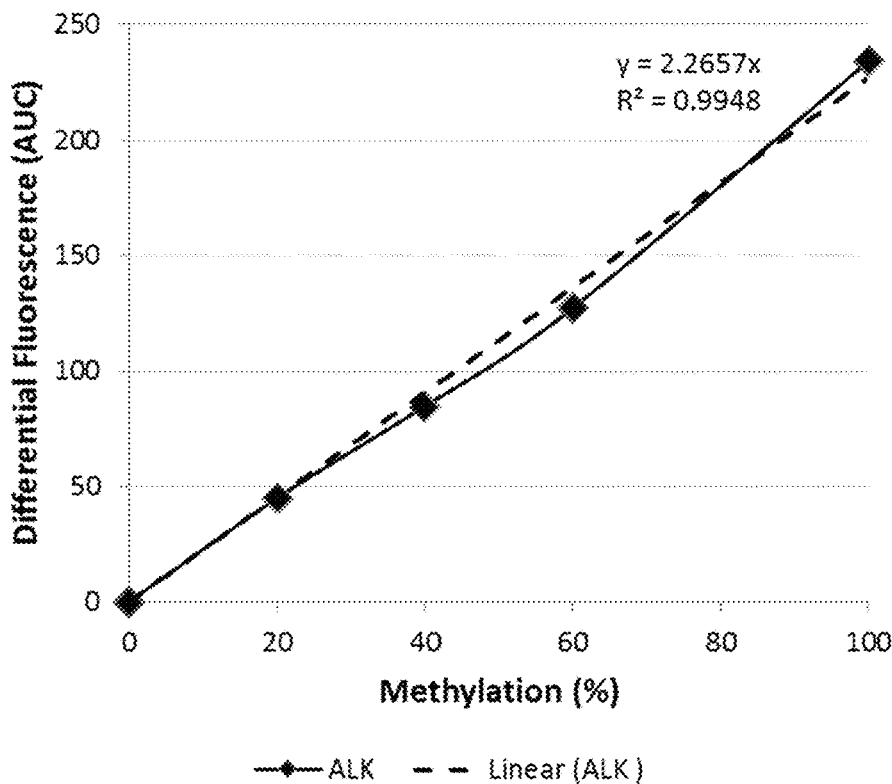
Figure 33:
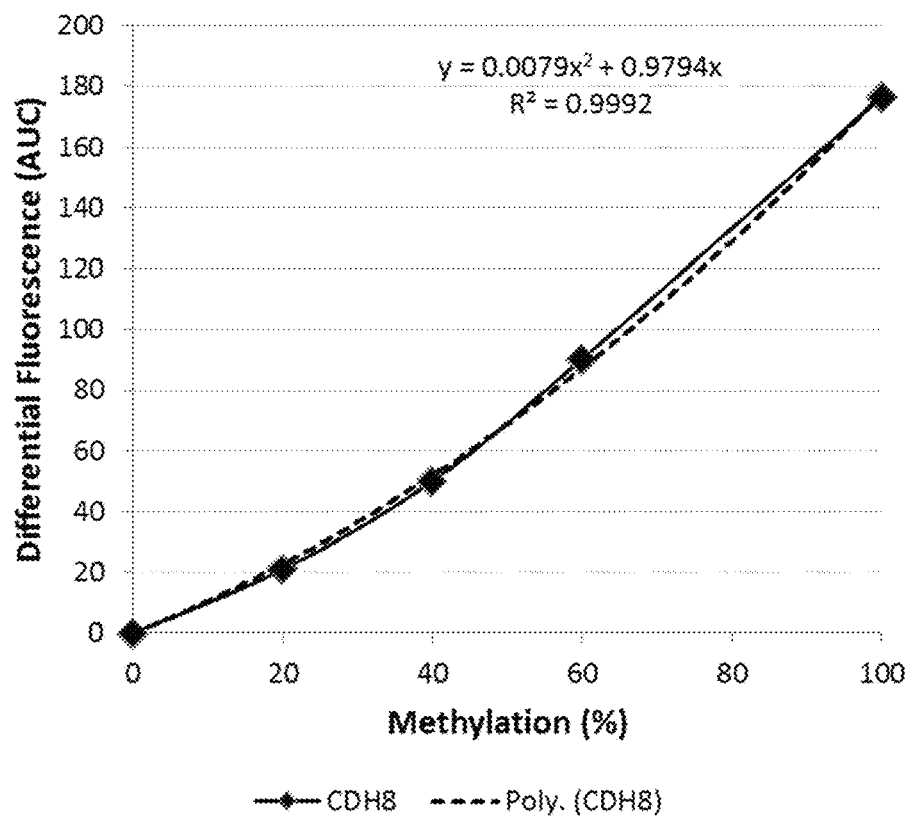
Figure 34:
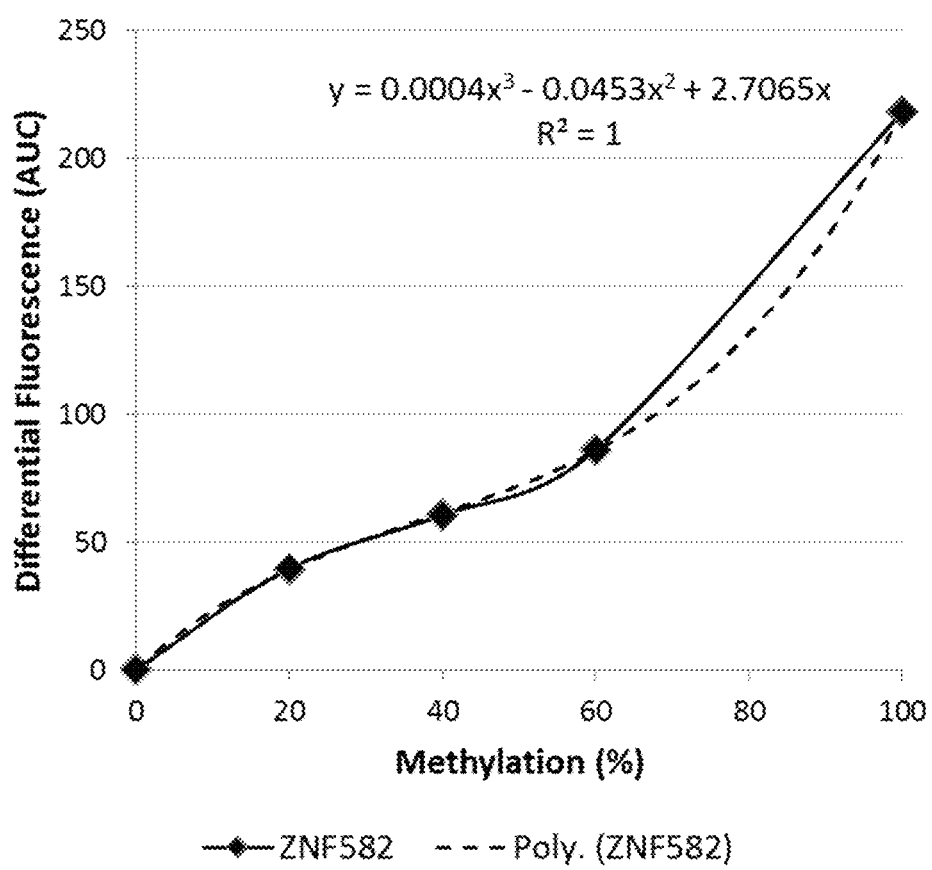

FIG. 32, FIG. 33, and FIG. 34 are graphs showing the best-fit regression line constructed from the area-under-the-curve (AUC) of the Fluorescence Difference plot using known methylated standards. The bisulfite-converted, methylated standards (0%, 20%, 40%, 60% and 100%) were amplified using the ALK (FIG. 32), CDH8 (FIG. 33), and ZNF582 (FIG. 34) primer sets and analyzed by high-resolution melting. The constructed regression line or curves as shown are used to quantitate the methylation level (%) of unknown, bisulfite-converted DNA from cervical cytology by extrapolation of post-melt fluorescence difference (AUC) values. The regression equation shown in each plot may be used to back calculate the methylation level (%) of the test sample.

DETAILED DESCRIPTION OF THE INVENTION

As disclosed herein, a prospective, cross-sectional study using residual liquid-based cytology samples for HPV genotyping and epigenetic analysis was conducted. Extracted DNA was subjected to parallel polymerase chain reactions using 3 primer sets (MY09/11, FAP59/64, GP-E6/E7 FB) for HPV DNA amplification. HPV+ samples were genotyped by DNA sequencing. Promoter methylation of 4 candidate tumor suppressor genes (ADCY8, CDH8, MGMT, ZNF582) out of 48 genes screened was quantified by bisulfite-pyrosequencing of genomic DNA. Independent validation of methylation levels was performed by analyzing data from cervical cancer cell lines and clinical samples from The Cancer Genome Atlas (TCGA). 277 quality cytology samples were analyzed. HPV was detected in 31/100 (31%) NILM, 95/100 (95%) LSIL, and 71/77 (92%) HSIL samples. The proportion of IARC-defined carcinogenic HPV types in sequenced samples correlated with worsening grade: NILM 7/29 (24%); LSIL 53/92 (58%); HSIL 65/70 (93%). Promoter methylation of ADCY8, CDH8, and ZNF582 measured in 170 samples: NILM (N=33), LSIL (N=70), and HSIL (N=67) also correlated with worsening grade. Similar hypermethylation patterns were found in cancer cell lines and TCGA samples. The combination of 4 biomarkers, i.e., HPV genotype and 3-gene promoter methylation predicted HSIL (AUC 0.89) better than HPV alone (AUC 0.74) by logistic regression and probabilistic modeling. Thus, the experiments herein show that HPV genotype and DNA methylation of ADCY8, CDH8, and ZNF582 are correlated with cytological grade. Therefore, HPV genotype and promoter methylation can be used to molecularly classify cervical cells as being normal or abnormal, e.g., NILM, LSIL, or HSIL. The HPV genotype and promoter methylation can be used in place of or in conjunction with cytological pap smears.

As disclosed herein, HPV carcinogenicity and promoter methylation of 3 tumor suppressor genes (ADCY8, CDH8, and ZNF582) were found to be positively correlated with worsening cytological grade. Additionally, the HPV/epimutation panel improved the prediction of HSIL and NILM over HPV alone.

This study aimed to determine the association between HPV genotypes and cellular epigenetic modifications in 3 grades of cervical cytology. As disclosed herein, there were positive correlations between HPV carcinogenicity, aberrant DNA methylation in the promoters of ADCY8, CDH8, and ZNF582, and cytological grade. The HPV positivity rate detected in normal cytology was 31% which increased precipitously to >90% in LSIL and HSIL samples. In comparison to a meta-analysis of worldwide HPV prevalence in normal cytology, the statistic based on the experiments herein was about 10% higher. This extended breadth of detection may be accounted for by the triple-primer PCR approach versus the single-primer PCR and Hybrid Capture 2 used in the majority of the studies cited. Furthermore, HPV-58 accounted for a significant proportion (13%) of carcinogenic HPV in the HSIL category. The high prevalence of HPV-58 may be explained by the study population. According to the 2010 Bureau of the Census, 63% of the population of San Antonio, Tex. is of Hispanic/Latino origin. Ethnogeographical predilection of HPV-58 has been observed in certain Latin American countries, to include Southeastern Mexico, Brazil, and Costa Rica. The race/ethnicity of our population derived from electronic medical records indicated 38% was categorized as "Other" or "Unknown". Based on the clinic population, "Other" may indicate a person of Hispanic/Latino origin.

The proportion of carcinogenic HPV genotypes found in the samples after genotyping was highest among the HSIL group. Cellular genomic analyses revealed a significant increase in promoter methylation of ADCY8, CDH8, and ZNF582 concomitant with worsening cytological grade. Conjointly, HPV carcinogenicity and the binarized methylation levels of the 3 genes were significant predictors of cytological outcome in a multivariable model. Specifically, HPV and ZNF582 demonstrated a high discriminatory performance as a screening test to differentiate normal (NILM) from abnormal cytology (LSIL/HSIL) with a negative predictive value (NPV) of 100%. In contrast, HPV and ADCY8, CDH8, and ZNF582 differentiated the <HSIL from HSIL samples with a positive predictive value (PPV) of 81%. In terms of clinical utility, the addition of quantitative methylation markers to the probabilistic model significantly improved the diagnostic accuracy of HPV carcinogenicity as a single predictor of cytological outcome.

Promoter hypermethylation of ADCY8, CDH8, and ZNF582 were corroborated in vitro in 5 cervical cancer cell lines with two exceptions. C33A cells exhibited low CDH8 methylation levels and DoTc2 failed the ADCY8 assay presumably due to low levels as well. Both C33A and DoTc2 cells are HPV-negative which may explain the hypomethylation as previously demonstrated in HPV+/HPV− head and neck squamous cell carcinoma (HNSCC) cell lines and tumors. The TCGA dataset confirmed in vivo hypermethylation in cervical tumors. Promoter methylation of ADCY8, CDH8, and ZNF582 were markedly elevated across all four stages of cervical carcinoma. The lack of variability between stages suggested these epimutations occurred early in the neoplastic process. Whether these alterations are tumor "driver" or "passenger" alterations are unknown. Nonetheless, they serve as informative host biomarkers for epithelial dysplasia/neoplasia. Moreover, within subject analysis of matched tumor and normal tissues verified differential promoter methylation for ADCY8, CDH8, and ZNF582. It is noteworthy to mention that the targeted CpG loci between pyrosequencing and HM450 methylation assays may not be identical hence rendering significantly different results. Different CpG positions, even in close proximity, within the same CpG-island may exhibit dissimilar methylation levels.

The strength of this study lies in the methodologies used for HPV detection and methylation quantification. HPV detection by parallel PCR and sequencing offers the greatest sensitivity and breadth of HPV detection. This method unleashes the constrained spectrum of HPV genotypes detected by commercial tests to obviate measurement bias. Furthermore, allocating the HPV genotypes by IARC-defined carcinogenicity numericizes oncogenic potential to allow for predictive modeling. In contradistinction, commercially available HPV tests only detect carcinogenic and not possibly or not classifiable HPV genotypes. Such dichotomized classification, i.e., high-risk positive or negative HPV has a significant level of false-negative rate due to non-detection of "low risk" HPV which may pose a clinical risk. As for quantitative DNA methylation, CpG analysis by pyrosequencing was chosen for its accuracy and high quantitative resolution. This method may also be easily translated into a clinically applicable test, i.e., real-time PCR with High Resolution Melt analysis. Essentially, the combination of biomarkers has emerged as a refinement of our current one dimensional clinical diagnostics, i.e., Pap or hrHPV, that serve as markers for detecting and quantifying oncogenic potential. Since this study was conducted as a biomarker discovery project, the about 300 samples used were considered the "training set" for predictive modeling.

In conclusion, the results of this study showed that different grades of cervical cytology possess different molecular signatures which may be translated into a multi-targeted "molecular pap" for clinical use. With the rapid evolution of molecular technologies, it is foreseeable that cervical cancer screening may become a fully automated, computerized, molecular diagnostic test that may circumvent economic hardships and nonexistent infrastructures for cytology-based screening programs in developing countries.

Results

HPV Carcinogenic Genotypes are Correlated with HSIL

Clinical and cytological characteristics are summarized in FIG. 1. Residual cytology samples (N=400) were collected between January 2013 and 2014. Of all samples, 31% (N=123) were excluded due to low quantity, low quality or sample excess as described in FIG. 1. For samples that met inclusion criteria (N=277), the corresponding subjects were composed predominantly of Caucasians (45%) with a median age of 28 yrs. (IQR, 24-35). The cytological specimens were stratified proportionately among the 3 grades: NILM 100/277 (36%); LSIL 100/277 (36%), and HSIL 77/277 (28%). The median concentration of extracted DNA among the 3 cytological categories (range, 46.3-51.8 ng/μL) was statistically equivalent (Kruskal-Wallis test, P=0.519) (FIG. 1).

Figure 2:
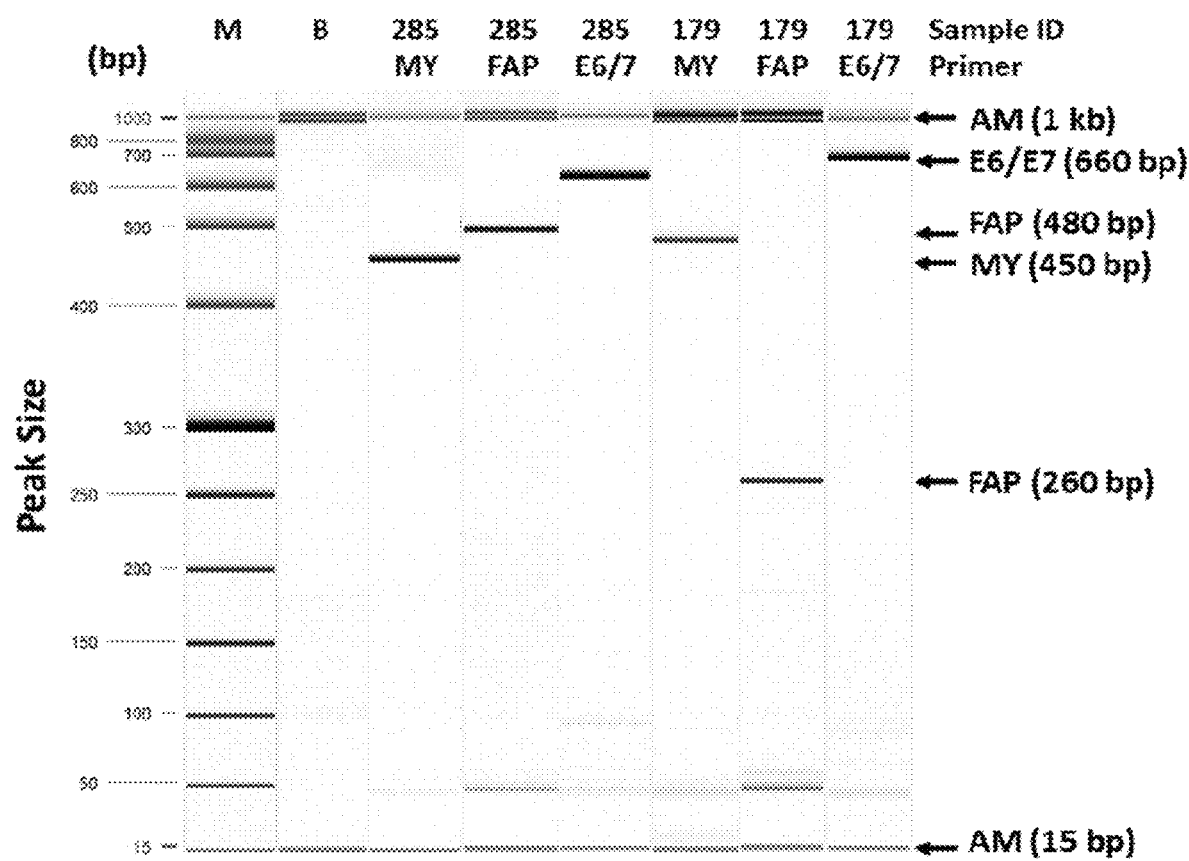
FIG. 2 is a representative gel image of PCR amplicon detection by high-resolution capillary gel electrophoresis. Representative samples #285 (LSIL) and #179 (HSIL) reveal MY09/11, FAP59/64, and GP-E6/E7 FB amplicons with expected yield of about 450, about 480 (or 260 bp fragment), and about 660 bp fragments, respectively.

To optimize HPV DNA detection, 3 primer sets targeting 3 distinct regions of the HPV genome were used. PCR amplification using primers MY09/11, FAP59/64, and GP-E6/E7 FB yielded expected 450-, 480-, and 660-bp fragments on capillary gel electrophoresis (FIG. 2). An unexpected short amplicon (260 bp) derived from amplification with the FAP primers was observed at higher frequency in HSIL samples. DNA sequencing and nucleotide BLAST mapped the 260 bp sequence nearest to the HPV-58 L1 segment (nucleotide range 6041 to 6253) belonging to the alpha-9 species but nonspecific for genotype identification. In particular, the amplicons were about 260 bp based on gel electrophoresis and mapped (using BLAST) to nucleotides 6047 to about 6254 (+/−a few nucleotide differences). For HSIL samples (N=77), 63/67 (94%) exhibited the 260 bp amplicons; LSIL samples (N=100), 9/73 (12.3%) exhibited the 260 bp amplicons, and NILM (N=100), 0/12 (0%) exhibited the 260 bp amplicons. Therefore, generation of 260 bp amplicons resulting from PCR amplification using the FAP59/64 primer set as described herein can be used to characterize a sample as being an HSIL sample. Partial loss of the HPV L1 gene, notably in HSIL, was presumed due to virus-to-host genome integration.

The gel electrophoresis positivity for HPV DNA after PCR of each sample by the 3 primer sets are summarized by intersecting and complementary sets within Venn diagrams in FIG. 3. The combined net positive rate of HPV DNA detection for NILM 31/100 (31%), LSIL 95/100 (95%), and HSIL 71/77 (92%) are represented by the union of 3 sets within each Venn diagram (FIG. 3). Of the PCR-positive samples that were sequenced, 191 samples were genotyped by BLAST.

Figure 4:
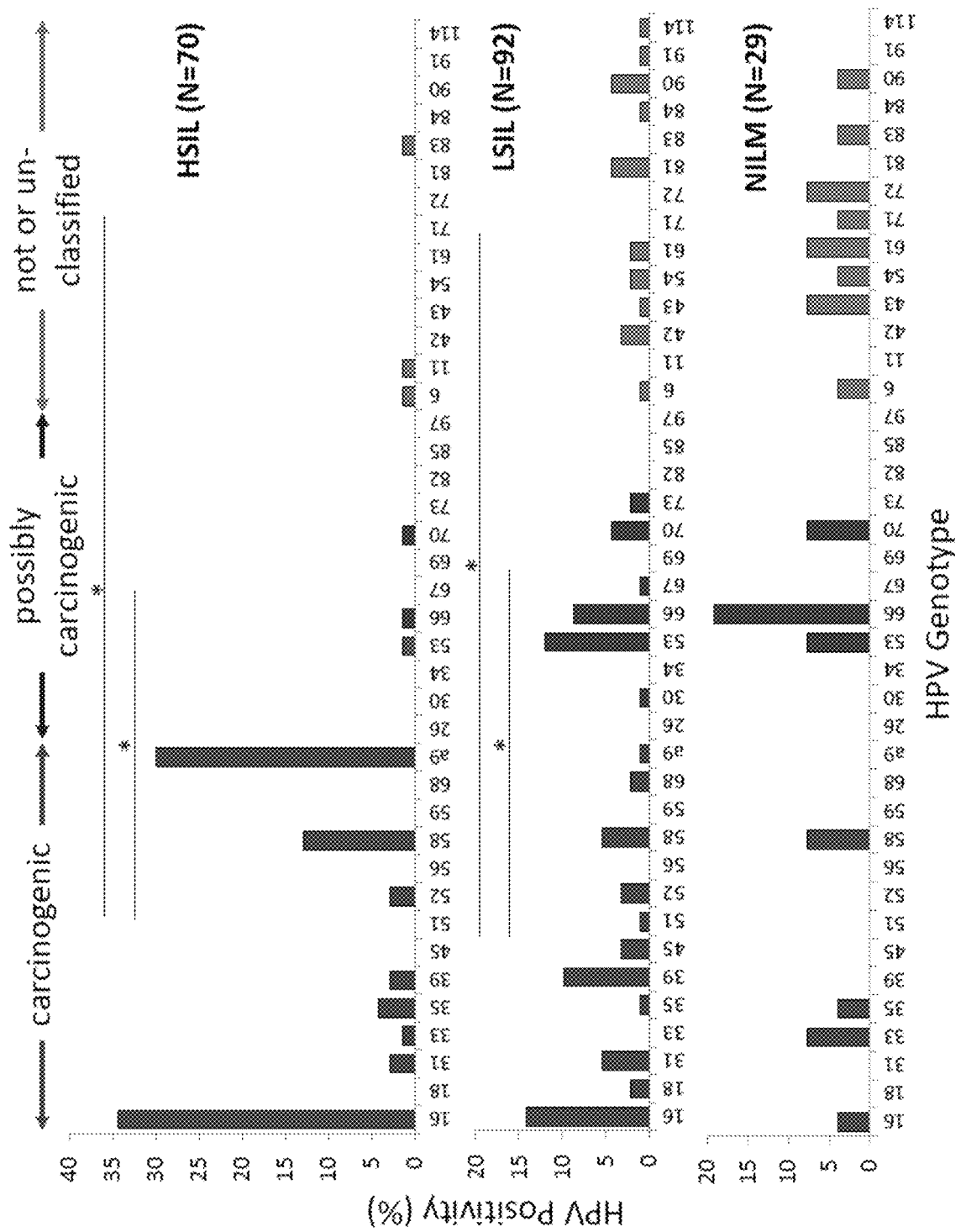
FIG. 4 are graphs showing the HPV genotype distribution of 191 cytology samples with PCR-detected HPV DNA according to cytological diagnoses: NILM, LSIL, and HSIL. The increase in carcinogenic HPV genotypes was coincident with cytological grade (Spearman's $\rho=0.658$, $P<0.001$). Samples positive for the 260-bp fragment which aligned closest to HPV-58 were assigned as "alpha-9" species due to the nonspecific short sequence length. *, $P<0.05$ by the chi-square test.

The prevalence of HPV genotypes found in 3 grades of cytology is shown in FIG. 4. The genotype spectrum spanned the continuum of IARC-defined carcinogenic potentials. As expected, there was a higher frequency of HPV 16 genotypes detected in low- and high-grade cytology. Notably, the proportion of carcinogenic HPV types positively correlated with cytological grade: NILM (23%), LSIL (49%), and HSIL (91%). Furthermore, LSIL and HSIL samples had a significantly greater proportion of carcinogenic than possibly carcinogenic and not or unclassifiable HPV genotypes (chi-squared, P<0.05); whereas, the distribution was indifferent among NILM. A high frequency of HPV-58 was noted particularly in HSIL samples.

DNA Methylation of ADCY8, CDH8, ZNF582 are Correlated with Cytological Grade

Figure 5:
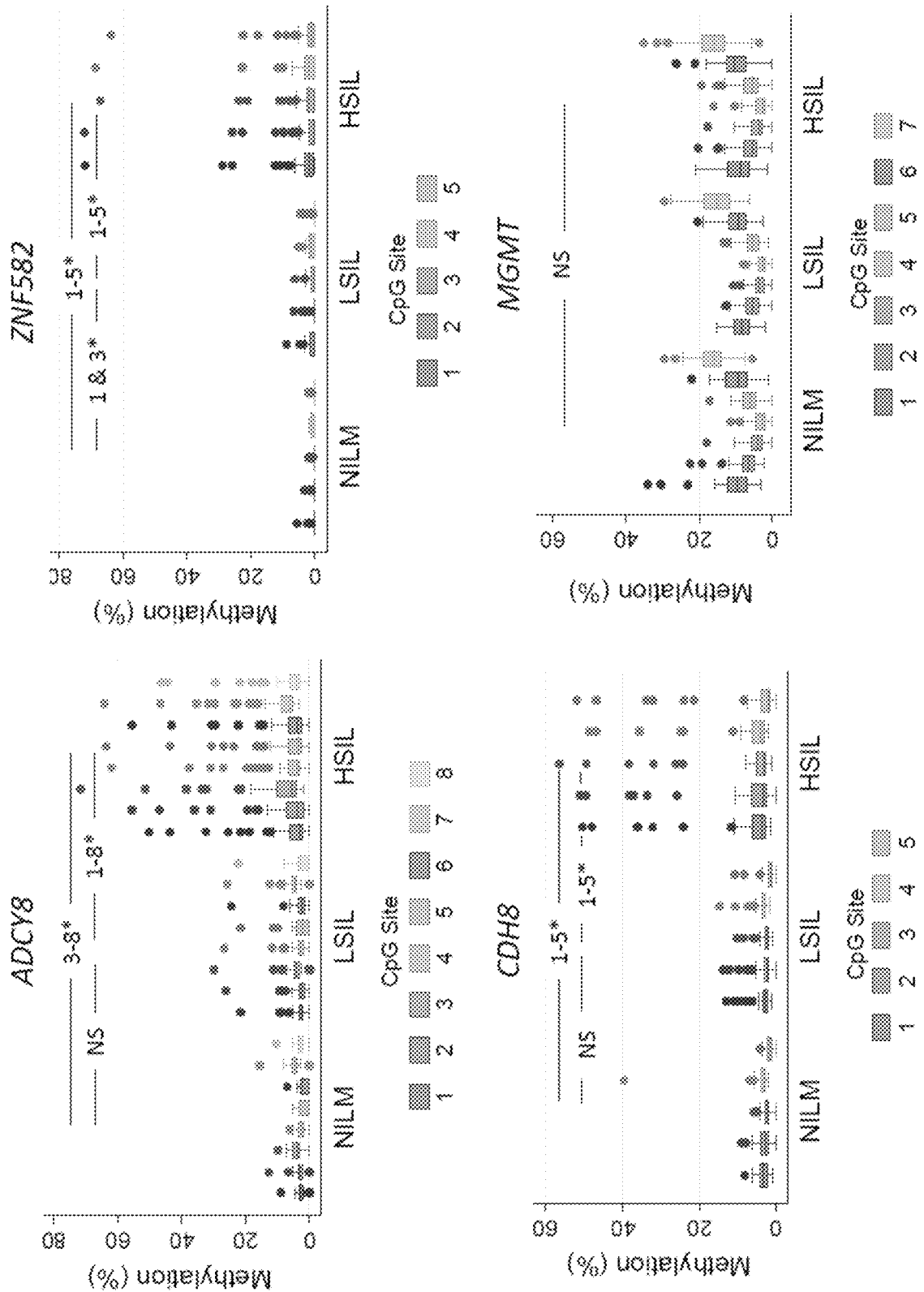
FIG. 5 are graphs showing the methylation (%) of total genomic DNA in 3 grades of cervical cytology, i.e., NILM, LSIL, and HSIL. Methylation was compared by CpG positions among 4 genes (ADCY8, CDH8, ZNF582, and MGMT). For each set of data points, the CpG sites are indicated in the order set forth at the bottom of each graph. Pairwise comparisons of methylation for each CpG position between cytological grades (NILM vs. LSIL, LSIL vs. HSIL, and NILM vs. HSIL) revealed significantly higher levels for HSIL vs. LSIL and LSIL vs. NILM at multiple positions for ADCY8, CDH8, and ZNF582. For MGMT, methylation levels were not statistically different among cytological grades. Methylation levels for each CpG position increased concurrently with cytological grade for ADCY8, CDH8, and ZNF582 by Spearman's $\rho$ ($P<0.001$). *, $P<0.05$ by the Wilcoxon rank-sum test.

The panel of genes selected for promoter methylation screening included genes previously reported to be hypermethylated in cervical carcinoma and other malignancies, e.g., brain, oral, breast, lung, hepatocellular, colorectal, and endometrial. The quantitative methylation results of 4 candidate genes selected for pyrosequencing stratified by Pap grade and CpG position is presented in FIG. 5. The results indicate a positive correlation between Pap grade and promoter methylation of ADCY8, CDH8, and ZNF582 (Spearman rank, P<0.05) but not MGMT. Pairwise comparison of methylation at each CpG locus between Pap grades revealed higher levels in HSIL than LSIL and NILM with a few exceptions (FIG. 5). The differences between LSIL and NILM were only significant for ZNF582 CpG 1 and CpG 3 (*) (FIG. 5). Interestingly, for MGMT, methylation levels were indifferent across Pap grades and CpG positions.

DNA Methylation of ALK is Positively Correlated with Cytological Grade

Figure 6:
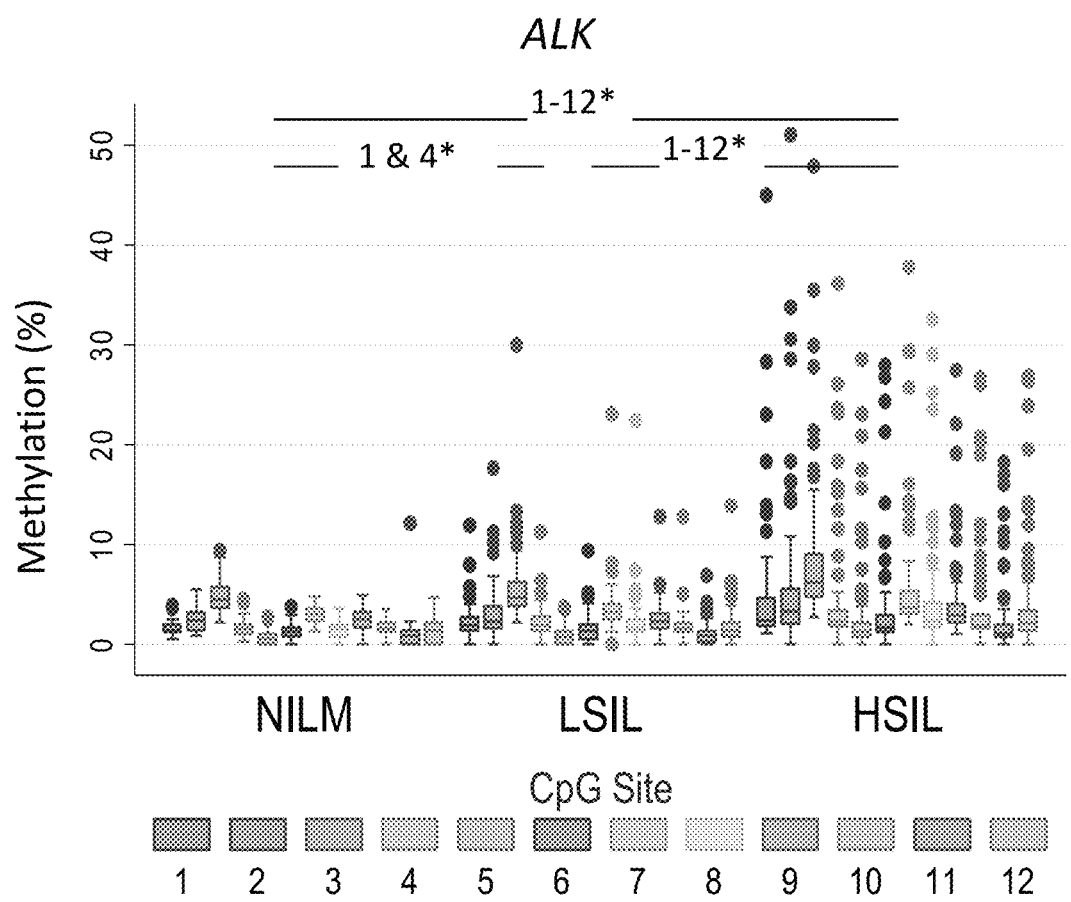
FIG. 6 is a graph showing the ALK promoter methylation differences in cervical cytology. Methylation (%) of total genomic DNA in 3 grades of cervical cytology, i.e., NILM, LSIL, and HSIL, was compared by CpG positions for gene ALK. Pairwise comparisons of methylation for each CpG position between cytological grades (NILM vs. LSIL, LSIL vs. HSIL, and NILM vs. HSIL) revealed significantly higher levels for HSIL vs. LSIL and HSIL vs. NILM at all positions. The differences between LSIL and NILM were only significant for ALK CpG loci 1 and 4 (*). Methylation levels for each CpG position increased concurrently with cytological grade for ALK by Spearman's $\rho$ ($P<0.05$). *, $P<0.05$ by the Wilcoxon rank-sum test.

The quantitative methylation results of the ALK promoter selected for pyrosequencing stratified by Pap grade and CpG position is presented in FIG. 6. The results indicate a positive correlation between Pap grade and promoter methylation of ALK (Spearman rank, p<0.05). Pairwise comparison of methylation at each CpG locus between Pap grades revealed higher levels in HSIL than LSIL and NILM with a few exceptions (FIG. 6). The differences between LSIL and NILM were only significant for ALK CpG 1 and CpG 4 (*) (FIG. 6).

Figure 7:
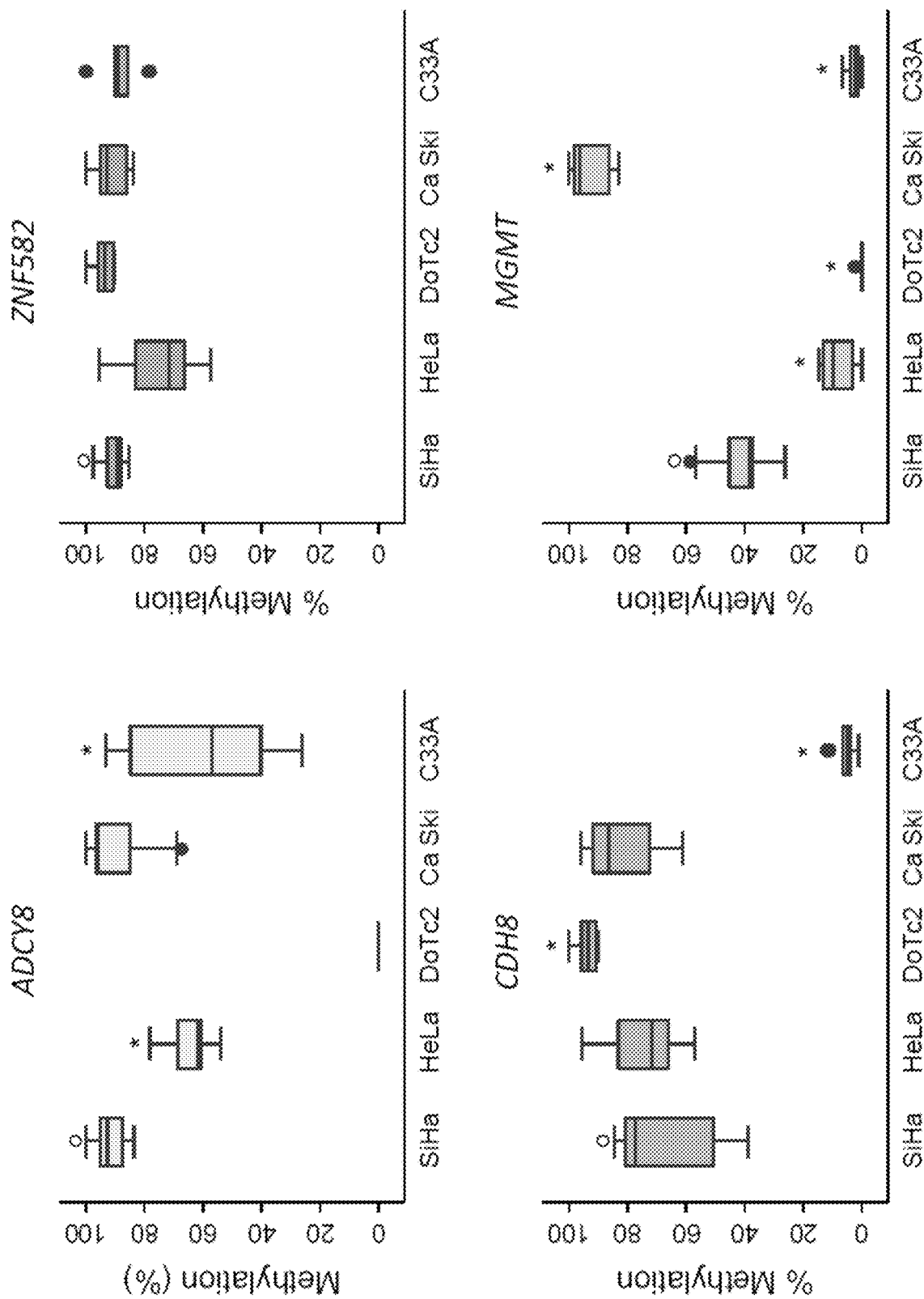
FIG. 7 are graphs showing that SiHa, HeLa, and Ca Ski cell lines with genome-integrated HPV demonstrated promoter hypermethylation of ADCY8, CDH8, and ZNF582 genes. For HPV negative cell lines, DoTc2 and C33-A revealed an inconsistent pattern of hypermethylation in the studied genes. Using SiHa methylation (%) as a reference (o), cell lines with significantly different levels are indicated by an asterisk. *, $P<0.05$ by the Wilcoxon rank-sum test. NS: not statistically significant. Cell lines were analyzed for CpG methylation in duplicate collections.

DNA Methylation of ADCY8, CDH8, ZNF582 are Validated in Cervical Cancer Cell Lines and TCGA Cohort Methylation of the 4 candidate genes were also quantified in 5 cervical cancer cell lines. The median methylation across all CpG sites for each gene stratified by cell line is presented in FIG. 7. In general, hypermethylation of ADCY8, CDH8, and ZNF582 was noted in all cell lines except C33A and DoTc2 (which failed the ADCY8 assay). For comparison between cell lines, the methylation levels of all 4 genes in SiHa (ranging from a low of about 38% in MGMT to a high of 93% in ADCY8) were used as the referent. Although some statistical differences in DNA methylation levels were detected, e.g., decreased methylation of ADCY8 in HeLa/C33A cells and CDH8 in C33A cells (FIG. 7), the HPV positive cell lines consistently exhibited high methylation levels (>50%). As for MGMT, the methylation levels among the cell lines were inhomogeneous and polarized (FIG. 7).

DNA Methylation of ALK is Validated in Cervical Cancer Cell Lines

Figure 8:
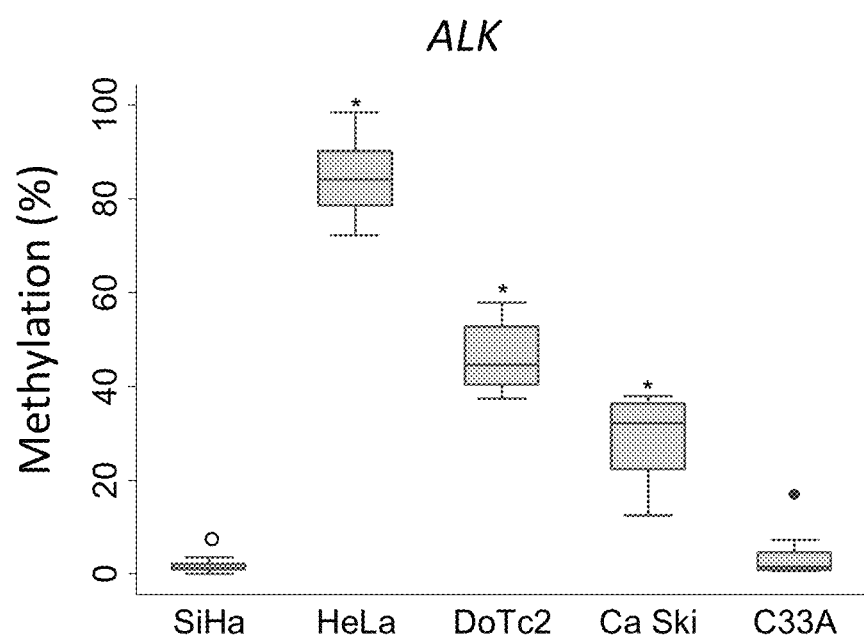
FIG. 8 is a graph showing ALK promoter methylation differences in cervical carcinoma cell lines. HeLa, DoTc2, and Ca Ski cell lines demonstrated promoter hypermethylation of ALK. Using SiHa methylation (%) as a reference (o), cell lines with significantly different levels are indicated by an asterisk. *, $P<0.05$ by the Wilcoxon rank-sum test. Cell lines were analyzed for CpG methylation in duplicate collections.

Methylation of the ALK promoter was also quantified in 5 cervical cancer cell lines. The median methylation across all CpG sites for each gene stratified by cell line is presented in FIG. 8. In general, hypermethylation of ALK was noted in all cell lines except SiHa and C33A. For comparison between cell lines, the methylation level of ALK in SiHa was used as the referent. ALK promoter methylation level was significantly higher (*) in HeLa, DoTc2, and Ca Ski cells in contrast to SiHa with a median level of 1.3% (IQR, 0.95 to 2.15) (FIG. 8).

DNA Methylation of ADCY8, CDH8, ZNF582 are Validated in TCGA Cohort

Figure 9:
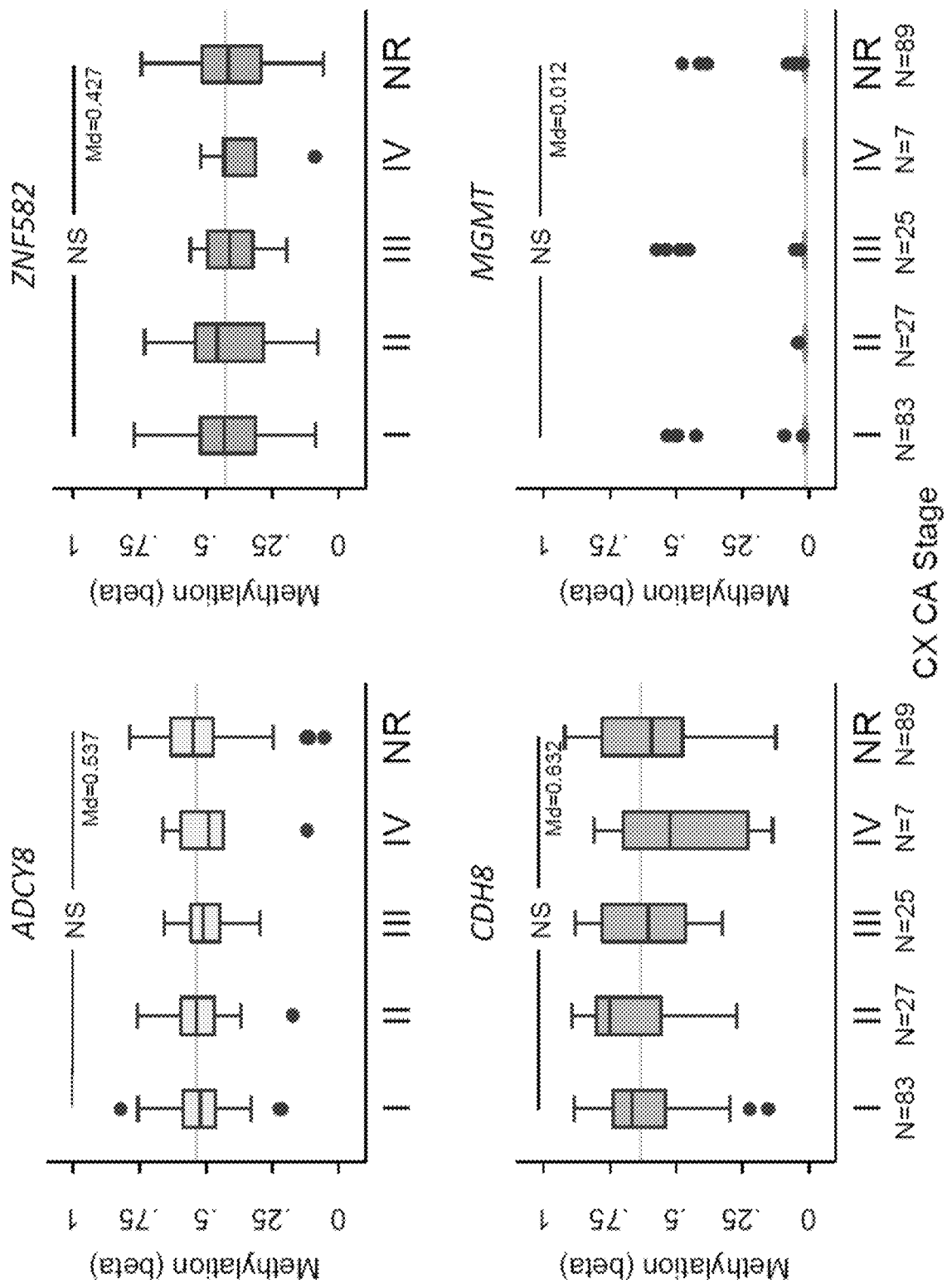
FIG. 9 are boxplots of CpG methylation ($\beta$ value) of ADCY8, CDH8, ZNF582, and MGMT in the TCGA cervical cancer cohort according to FIGO stage for 231 patient samples with squamous cell carcinoma. Gene-specific median methylation levels for all FIGO stages are specified (Md) and indicated by the blue reference lines. NS: not statistically significant, Kruskal-Wallis $P>0.05$. NR: stage not reported.
Figure 10:
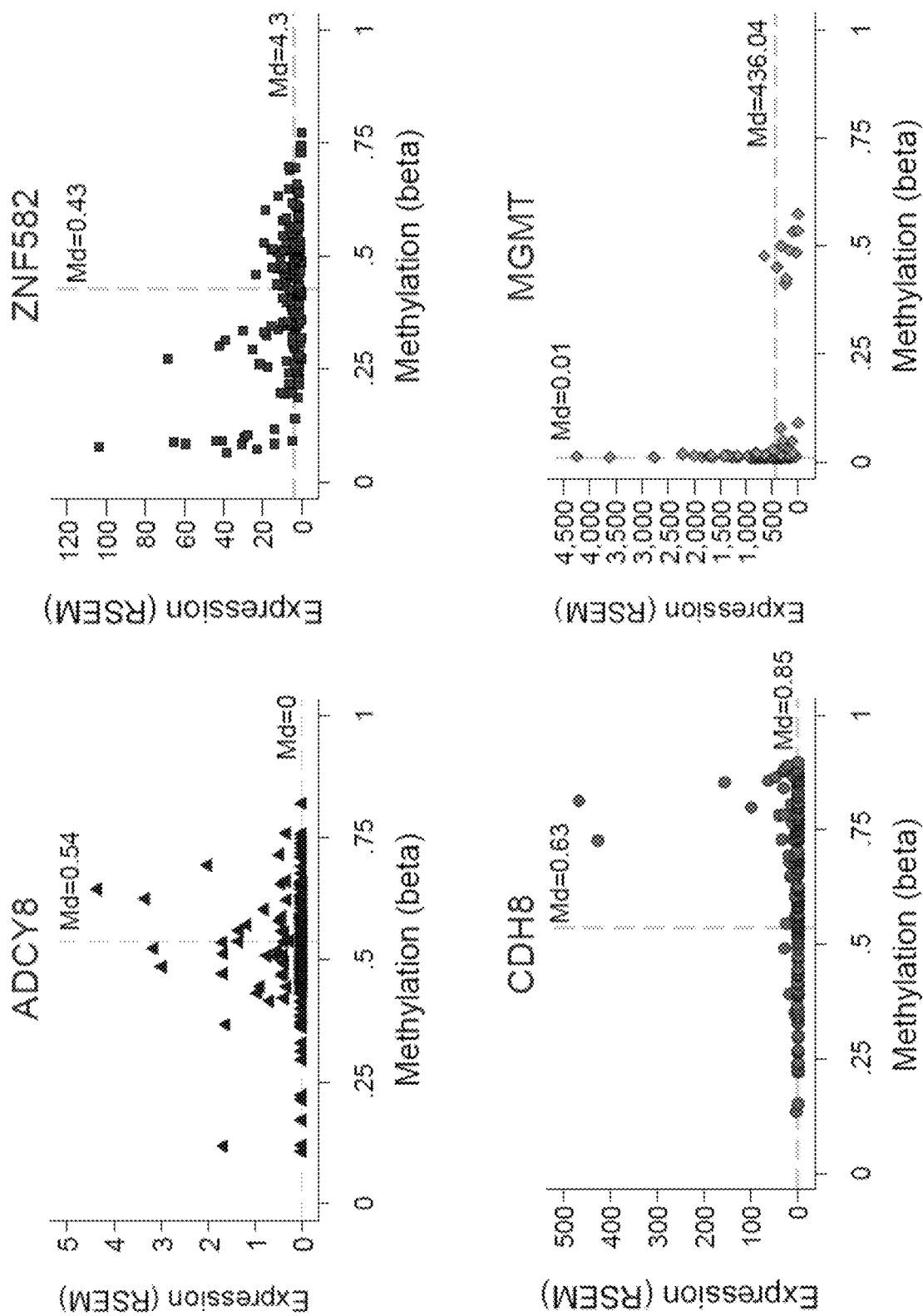
FIG. 10 are graphs showing the DNA methylation and gene expression of ADCY8, CDH8, ZNF582, and MGMT in the TCGA cervical cancer cohort. Correlation plot for 181 patient tumors using paired median CpG methylation (beta value) and expression value (RSEM-normalized) from each sample. Median values (Md) for each axis are marked with a dotted line. (ADCY8: rho=0.01, P=0.94; ZNF582: rho=−0.23, P=0.001; CDH8: rho=0.27, P<0.001; MGMT: rho=−0.17, P=0.03).
Figure 11:
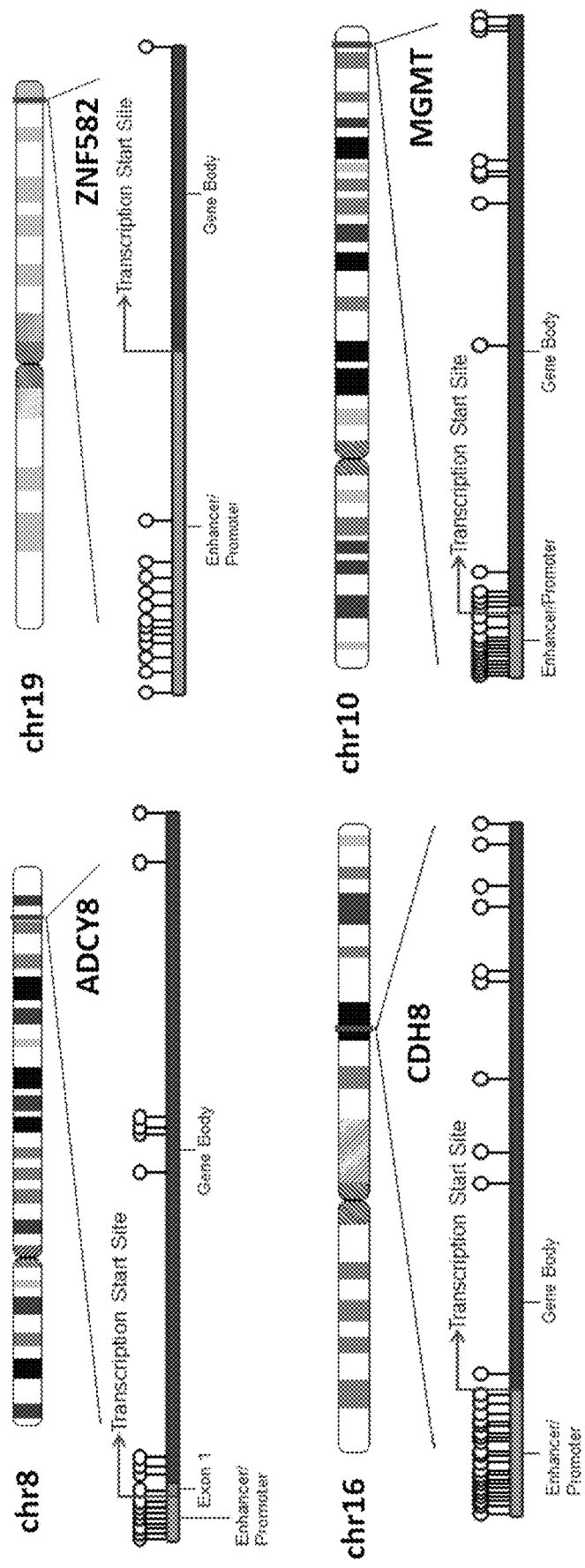
FIG. 11 schematically shows the differential CpG methylation ($\beta$ value) ante- and post-transcription start site for 257 cervical carcinomas (squamous, N=231; adenocarcinoma, N=26). The 4 panels display the chromosomal positions of ADCY8, CDH8, ZNF582, and MGMT (line) with an expanded area showing the CpG probes on the Illumina HumanMethylation 450K microarray (gene ball-and-stick diagrams).

TCGA data for the cervical cancer cohort (N=231) revealed distinct hypermethylation patterns among ADCY8, ZNF582, and CDH8 (FIG. 9) for reported and non-reported clinical stages (median β-value range, 0.427-0.632). For MGMT, the methylation was consistently low with a median β-value of 0.012 across all stages. Also, methylation levels were not distinguishable between stages for the 4 genes (Kruskal-Wallis, P>0.05). Association analysis between methylation and matched RNA-Seq expression data revealed modest anti-correlation for ZNF582 (Spearman's p=−0.2349, P<0.05) and MGMT (Spearman's p=−0.1660, P<0.05) but not for ADCY8 and CDH8 (FIG. 10).

Figure 12:
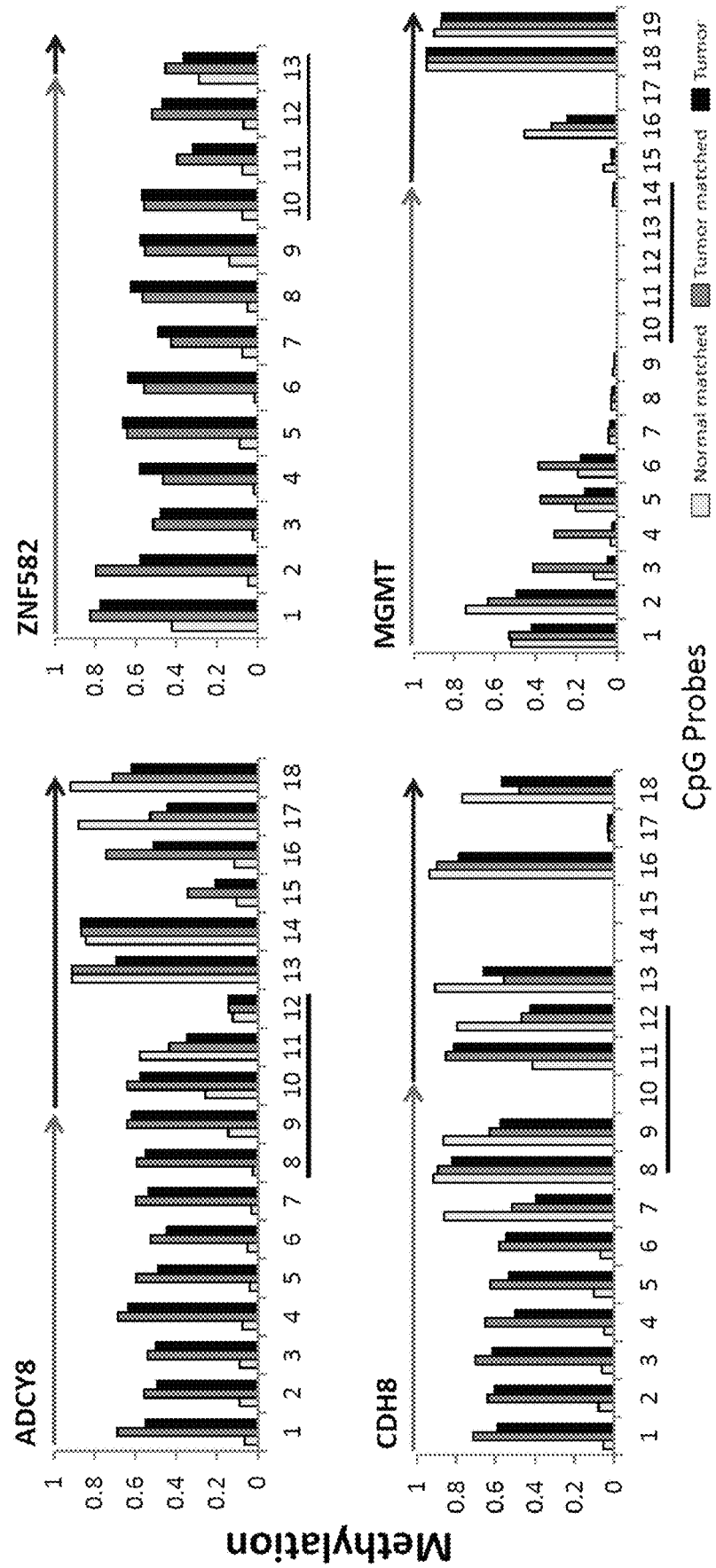

TCGA data for the 3 available tumor/normal matched pairs of cervical tissues were examined for within and between subject promoter methylation differences. Due to the small sample size, formal statistical analysis was not performed. However, increased median methylation (about 10×) of ADCY8, CDH8 and ZNF582, but not MGMT, was noted in the tumor cohort (N=257) compared to the 3 normal samples (FIG. 12). Of note, the methylation levels for the adenocarcinomas (N=26) were comparable to the squamous carcinomas, hence these samples were included in the tumor cohort.

HPV Genotype and DNA Methylation of ADCY8, CDH8, and ZNF582 as Predictors of Cytological Outcomes The logistic regression analysis and ROC curves for the univariable and multivariable logit models for cytological outcomes are presented in FIG. 13, FIG. 14, and FIG. 15, respectively. For Model 1, the best predictors were HPV carcinogenicity and CpG 3 of ZNF582 with an area under ROC of 0.93. For Model 2, the best predictors were HPV carcinogenicity and CpG 7 of ADCY8, CpG 3 of CDH8, and CpG 3 of ZNF582 with an area under ROC of 0.89. The discriminatory performance of both multivariable models inclusive of methylation markers was better than the univariate predictor (HPV carcinogenicity) model by comparing areas under ROC ($\chi^2$, P<0.05).

Predicted probabilities at representative values over the range of predictor variables are presented as marginsplots (FIG. 16 to FIG. 18). FIG. 18 illustrates the segregating effect of ZNF582 over HPV carcinogenicity alone as a predictor of abnormal Paps (LSIL/HSIL). More importantly, HPV negativity in conjunction with low ZNF582 methylation was highly indicative of a normal Pap with a negative predictive value (NPV) of 100%. The predicted probabilities or margins for all possible combinations (N=8) of predictor variables in Model 1 are provided in FIG. 19. For Model 2, the cumulative effects of ADCY8, CDH8, and ZNF582 promoter methylation over HPV carcinogenicity alone as a predictor of HSIL were significant. The probability of HSIL increased incrementally as the number of methylated genes increased from 0 to 3 (FIG. 17, 4-panel chart). The predicted probabilities for all possible combinations (N=32) of predictor variables in Model 2 are tabulated in FIG. 20.

The diagnostic performance characteristics of Models 1 and 2 are presented in FIG. 21 and FIG. 22.

For clinical performance, the sensitivity of HPV+ZNF582 was higher (100%) than HPV (90%) in detecting abnormal (LSIL/HSIL) cytology. The PPV were comparable at 93 to 95% suggesting that for patients with a positive assay result, almost all have abnormal cytology. In contrast, for patients with a negative assay, the chance of finding no disease (NPV) was 100% for HPV+ZNF582 vs. 66% for HPV. This indicates that HPV+ZNF582 a better screening test. As for Model 2, the PPV was greater for the HPV+3-methylation marker (81%) vs. HPV (58%) suggesting that in patients with a + multi-marker test, almost 80% will have HSIL. Furthermore, the false-positive rate is lower for the HPV+ 3-methylation marker (22%) than HPV (42%). Essentially, the results of the 2 models indicate that HPV+ZNF582 is a better predictor of NILM; whereas HPV+3-methylation markers is a better predictor of HSIL than HPV alone.

HPV Genotype and DNA Methylation of ALK as Predictors of HSIL

The logistic regression analysis and ROC curves for the univariable and multivariable logit models for cytological outcomes are presented in FIG. 23 and FIG. 24, respectively. In comparison to HPV carcinogenicity as the sole predictor of HSIL, the addition of the methylation level of CpG 5 of ALK improved the diagnostic performance as shown by the areas under ROC ($\chi^2$, p<0.01) (FIG. 24). On the contrary, the addition of ALK promoter methylation to Models 1 and 2, as detailed above, did not enhance the preexistent discriminatory performance (p>0.05).

Predicted probabilities at representative values over the range of predictor variables are presented as marginsplots (FIG. 25). FIG. 25 illustrates the segregating effect of ALK over HPV carcinogenicity alone as a predictor of HSIL. This was most notable in samples containing possibly carcinogenic or carcinogenic HPV (*, p<0.05). The probability of HSIL was highest (about 75%) when the HPV was carcinogenic and ALK was hypermethylated (FIG. 25). The predicted probabilities or margins for all possible combinations (N=8) of predictor variables are provided in FIG. 26.

The following examples are intended to illustrate but not to limit the invention.

Materials and Methods

Subjects and Samples

This study was conducted after approval by the Institutional Review Board of Brooke Army Medical Center (BAMC), Texas. Inclusion criteria were cervical specimens derived from adult women ≥18 years of age undergoing cervical cytology screening. Exclusion criteria were cervical specimens from patients with conditions that may alter genomic methylation, e.g., pregnancy and non-HPV sexually transmitted infections.

Liquid-based cytology collected for clinical testing at the Department of Pathology was consecutively procured after completion of analysis for cytological diagnosis. Samples were refrigerated at 4° C. until weekly batch DNA extraction. Demographic data were abstracted from the electronic health record (AHLTA) of the Department of Defense (DoD) and code-linked to each specimen. Three categories of samples, i.e., Negative for Intraepithelial Lesion or Malignancy (NILM), Low-grade squamous intraepithelial lesion (LSIL), and High-grade squamous intraepithelial lesion (HSIL) were collected until meeting target accrual numbers: NILM (N=100), LSIL (N=100), and HSIL (N=77).

Sequences and CpG Positions

The sequences and CpG positions of ADCY8, CDH8, ZNF582, and ALK are as follows:

ADCY8

Adenylate cyclase 8, *Homo sapiens* chromosome 8, GRCh38.p7 Primary Assembly, NC_000008.11; GI:568815590, bases 130780300 to Ser. No. 13/041,604, complement Anti-sense strand analyzed for CpG methylation (CpG sites underlined):

(SEQ ID NO: 1)
5'-CGCGCCGCAGCTGTCAGGCGACTCGGCGCTGCCCCTCTACTCGCTGG

GCCCG-3'

CpG Coordinates on chromosome 8 GRCh38 assembly (nucleotide position of SEQ ID NO: 1):

| CpG Site | GRCh38 Coordinate on Chromosome 8 | Nucleotide Position in SEQ ID NO: 1 |
|---|---|---|
| CpG 1 | 131040097 | 1 |
| CpG 2 | 131040095 | 3 |
| CpG 3 | 131040092 | 6 |
| CpG 4 | 131040079 | 19 |
| CpG 5 | 131040074 | 24 |
| CpG 6 | 131040071 | 27 |
| CpG 7 | 131040056 | 42 |
| CpG 8 | 131040047 | 51 |

Thus, for example, CpG 1 of ADCY8 refers to nucleotide position 1 of SEQ ID NO: 1.

CDH8

Cadherin 8, *Homo sapiens* chromosome 16, GRCh38.p7 Primary Assembly, NC_000016.10, GI:568815582, bases 61640435-62036835, complement Sense strand analyzed for CpG methylation (CpG sites underlined):

(SEQ ID NO: 2)
5'-CGGCTACGGAGTCCCCGGCTTAAGGGGCCTCCGTGCACGC-3'

CpG Coordinates on chromosome 16 GRCh38 assembly (nucleotide position of SEQ ID NO: 2) CpG #1: 62035318 (nucleotide 1):

| CpG Site | GRCh38 Coordinate on Chromosome 16 | Nucleotide Position in SEQ ID NO: 2 |
|---|---|---|
| CpG 1 | 62035318 | 1 |
| CpG 2 | 62035324 | 7 |
| CpG 3 | 62035333 | 16 |
| CpG 4 | 62035350 | 33 |
| CpG 5 | 62035356 | 39 |

Thus, for example, CpG 1 of CDH8 refers to nucleotide position 1 of SEQ ID NO: 2.

ZNF582

Zinc finger protein 582, *Homo sapiens* chromosome 19, GRCh38.p7 Primary Assembly, NC_000019.10, GI:568815579, bases 56382751 to 56393601, complement Anti-Sense strand analyzed for CpG methylation (CpG sites underlined):

(SEQ ID NO: 3)
5'-ACGCAGACGTCTCGCCTCATCGTCGC-3'

CpG Coordinates on chromosome 19 GRCh38 assembly (nucleotide position of SEQ ID NO: 3):

| CpG Site | GRCh38 Coordinate on Chromosome 19 | Nucleotide Position in SEQ ID NO: 3 |
|---|---|---|
| CpG 1 | 56393356 | 2 |
| CpG 2 | 56393350 | 8 |
| CpG 3 | 56393345 | 13 |
| CpG 4 | 62035337 | 21 |
| CpG 5 | 56393334 | 24 |

Thus, for example, CpG 1 of ZNF582 refers to nucleotide position 2 of SEQ ID NO: 3.

ALK

Anaplastic lymphoma receptor tyrosine kinase, *Homo sapiens* chromosome 2, GRCh38.p7 Primary Assembly, NC_000002.12, GI:568815596, bases 29192774 to Ser. No. 29/921,611, complement Anti-Sense strand analyzed for CpG methylation (CpG sites underlined):

(SEQ ID NO: 4)
5'-CGCCGCCTCTGTTCGGAGGGTCGCGGGGCACCGAGGTGCTTTCCGGC

CGCCCTCTGGTCGGCCACCCAAAGCCGCGGGCG-3'

CpG Coordinates on chromosome 2 GRCh38 assembly (nucleotide position of SEQ ID NO: 4):

| CpG Site | GRCh38 Coordinate on Chromosome 2 | Nucleotide Position in SEQ ID NO: 4 |
|---|---|---|
| CpG 1 | 29921532 | 1 |
| CpG 2 | 29921529 | 4 |
| CpG 3 | 29921519 | 14 |
| CpG 4 | 29921511 | 22 |
| CpG 5 | 29921509 | 24 |
| CpG 6 | 29921501 | 32 |
| CpG 7 | 29921489 | 44 |
| CpG 8 | 29921485 | 48 |
| CpG 9 | 29921474 | 59 |
| CpG 10 | 29921460 | 73 |
| CpG 11 | 29921458 | 75 |
| CpG 12 | 29921454 | 79 |

Thus, for example, CpG 1 of ALK refers to nucleotide position 1 of SEQ ID NO: 4.

Cell Lines and Culture

Five cervical cancer cell lines (SiHa, HeLa Ca Ski, C33-A, and DoTc2) were acquired from American Type Culture Collection (ATCC) to serve as (+) controls and comparators of methylation. The cell type, tumor-site derivation, and HPV status were: SiHa (squamous, primary, HPV16+); HeLa (adenocarcinoma, primary, HPV18+); Ca Ski (squamous, small intestine metastasis, HPV16+/18+);

C33-A (epithelial, primary, HPV−); and DoTc2 (epithelial, primary, HPV−). Cells were cultured in flasks for DNA extraction and μ-Slides (Ibidi) for microscopy with appropriate media supplemented with 10% FBS. EMEM medium (ATCC) was used to grow HeLa, C-33A, and SiHa cells. DMEM and RPMI-1640 media (ATCC) were used to culture DoTc2, and Ca Ski cells, respectively. Cells were grown at 37° C. in a $CO_2$ incubator until reaching 80-90% confluence. For methylation analysis, cellular DNA was extracted for bisulfite conversion and pyrosequencing as described below for cytology samples. For visualization of phenotypic differences, cellular organelles were stained as follows. Mitochondria were stained by incubating cells overnight with fresh media containing 300 nanomolar of MitoTracker® Orange CM-H2TMRos (Thermo Fisher Scientific, Waltham, Mass.) followed by washing with fresh media for 15-30 minutes at 37° C. Cells were fixed and permeabilized with the FIX & PERM® Cell Permeabilization Kit (Thermo Fisher Scientific) according to the manufacturer's instructions. Actin and nuclei were stained with respective reagents, ActinGreen™ 488 ReadyProbes® Reagent (Thermo Fisher Scientific) and NucBlue® Fixed Cell ReadyProbes® Reagent (Thermo Fisher Scientific), washed with PBS and mounted in ProLong® Gold Antifade Mountant (Thermo Fisher Scientific). Images were acquired by a Leica TCS SP5 II confocal microscope (Leica Microsystems).

TCGA Cohort

The cervical cancer cohort of The Cancer Genome Atlas (TCGA) was accessed on Oct. 3, 2014 to acquire DNA methylation data of squamous cell carcinomas (N=231) and adenocarcinomas (N=26). The methylation data (β-value) generated with the Illumina (San Diego, Calif.) HumanMethylation450 platform (HM450) in level-3 format was used to determine promoter methylation levels of ADCY8, CDH8, MGMT, and ZNF582. The matched RNA-SeqVersion 2 expression data (Reference 18) were accessed via the cBioPortal (Reference 19) to determine the correlation between methylation and expression of the 4 genes of interest. The few available samples (N=3) with matched (tumor/normal) DNA methylation (accessed on Jan. 15, 2015) were used to compare within and between subject differences.

Laboratory Schema

FIG. 27 illustrates the laboratory schema. After sample collection, cellular DNA is extracted from cervical cytology or cultured cancer cell lines. The DNA is subjected to HPV DNA amplification, sequencing, and genotyping. For DNA methylation analysis, the genomic DNA undergoes bisulfite conversion and pyrosequencing. Results derived from HPV genotyping and methylation quantification are analyzed for association or correlation with the cytological grade. FIG. 28 shows representative images of the 3 categories of cervical cytology and 5 immunostained cervical cancer cell lines used in this study. Morphological features and differences are highlighted by the relative size and distribution of organelles, i.e., mitochondria (orange), actin filaments (green), and nuclei (blue).

HPV DNA Amplification

Cervical cytology (10 mL) was centrifuged (13,000 rpm×2 minutes) and removed of supernatant. The cell pellet (200-250 μL) was transferred into sample tubes (2 mL) and placed in the QIAcube robotic workstation (Qiagen, Valencia, Calif.) for DNA extraction using the QIAamp DNA Mini kit (Qiagen). The purified DNA in 150 μL of eluent was quantified by spectrophotometry and stored at −20° C. prior to amplification. For HPV DNA amplification, three consensus primer sets:

```
1)
MY09:
                                  (SEQ ID NO: 5)
5'-CGTCCMARRGGAWACTGATC-3'

MY11:
                                  (SEQ ID NO: 6)
5'-GCMCAGGGWCATAAYAATGG-3'

2)
FAP59:
                                  (SEQ ID NO: 7)
5'-TAACWGTIGGICAYCCWTATT-3'

FAP64:
                                  (SEQ ID NO: 8)
5'-CCWATATCWVHCATITCICCATC-3';
and 3)
GP-E6-3F
                                  (SEQ ID NO: 9)
5'-GGGWGKKACTGAAATCGGT-3'

GP-E7-5B:
                                  (SEQ ID NO: 10))
5'-CTGAGCTGTCARNTAATTGCTCA-3',

GP-E7-6B:
                                  (SEQ ID NO: 11)
5'-TCCTCTGAGTYGYCTAATTGCTC-3'
``` were used to amplify two regions of HPV L1 and E6/E7 for genotype identification (References 20-22).

AmpliTaq Gold 360 Master Mix (Thermo Fisher Scientific) and Qiagen Multiplex PCR Plus kit (Qiagen) were used with the doublet and triplet primer sets, respectively. Briefly, PCRs were performed in a final volume (50 μL) containing template DNA (200 ng), PCR Master Mix (25 forward and reverse primers (1 μM each), and RNAase-free water. The cycling protocols for the 3 primer sets were: 1) MY09/11: activation (95° C.×5 minutes); 40 cycles of 3-step cycling (95° C.×30 seconds, 57° C.×90 seconds, 72° C.×90 seconds); final extension (72° C.×10 minutes), 2) FAP59/64: activation (95° C.×5 minutes); 40 cycles of 3-step cycling (94° C.×60 seconds, 50° C.×90 seconds, 72° C.×60 seconds); final extension (72° C.×10 minutes), 3) GP-E6/7: activation (95° C.×5 minutes); 45 cycles of 3-step cycling (94° C.×30 seconds, 55° C.×90 seconds, 72° C.×90 seconds); final extension (72° C.×10 minutes). After amplification, high-resolution capillary gel electrophoresis was used to detect amplicons by the QIAxcel (Qiagen) using the OM500 protocol. Samples with amplicon bands were selected for DNA sequencing.

HPV DNA Sequencing and Genotyping

PCR products were purified using the GeneRead Size Selection Kit (Qiagen) on the QIAcube robot. Sanger sequencing of the amplicons (about 200 ng DNA/sample) was performed by using sequencing primers MY11, FAP59, and GP-E6-3F as appropriate (Eurofins). Sequence quality was assessed using the Sequence Scanner 2.0 (appliedbiosystems.com) where a "high quality" Trace Score (TS) (average basecall quality value) was defined as ≥20 and a QV20+ value (total number of bases in the sequence with TS≥20) as ≥100. Quality sequences were filter selected for entry into the Basic Local Alignment Search Tool (BLAST®) and queried against HPV sequences in GenBank® under Virus Taxonomy ID #151340 (Reference 23).

The HPV genotype was based on the most homologous and significant result. The proportion of samples with detected HPV genotypes was quantitated and differences in HPV carcinogenic status among cytological groups was compared using Spearman's rho. The proportion of samples in distinct HPV carcinogenicity groups within each cytological category was compared using the chi-squared test.

Gene Selection and Methylation Analysis

To confirm and discover new hypermethylated genes in cervical carcinoma, 48 genes were selected for testing. For methylation profiling of cervical cytology, extracted genomic DNA ($\geq 20$ ng/µL) was bisulfite-converted using the EZ DNA Methylation™ Kit (Zymo Research Corp., Irvine, Calif.) to convert unmethylated cytosine residues to uracil. The converted DNA in the same cytological category was amassed to generate 3 pools by using equal amounts (2 µL) from individual samples. Specifically, the first 36, 42, and 18 samples collected from respective NILM, LSIL, and HSIL categories were used for pooled methylation screening (Reference 24). The PCR cycling protocol using the Applied Biosystem polymerase (N12338) was as follows: activation (95° C.×5 minutes); 50 cycles of 3-step cycling (95° C.×60 seconds, 60° C.×60 seconds, 72° C.×60 seconds); final extension (72° C.×7 minutes). Loci-specific PCR amplification of the pooled DNA (10-20 ng) in technical replicates using Qiagen or PyroMark SW 2.0 designed primers (FIG. 29) was followed by pyrosequencing on the PyroMark Q96 MD system (Qiagen). Methylation quantification of each CpG site was performed using the PyroMark CpG 1.0 software. The built-in internal quality control for bisulfite treatment and non-specific background was set at 6.5%.

The screening criteria used to define hypermethylation at each CpG site was $\geq 2.0\times$ the methylation level (%) of normal cytology samples. This method is comparable to the selection criteria used by Farkas et al. (Reference 25) for β-values derived from the Illumina HM450 platform. A CpG locus was considered hypermethylated if the Δβ-value was $\geq 0.2$ and the baseline (normal tissue) was <0.2. Six genes met our screening criteria: ADCY8, CDH8, ZNF582, MGMT, ALK, and NEFL. The best candidates (first 4 genes) were selected for further testing of individual samples based on their association with cervical, oral, and/or endometrial carcinoma.

Definitions, Variable Coding, and Logistic Modeling

For this study, the classification of HPV carcinogenicity was based on the WHO IARC Working Group Reports (References 7, 8). Specifically, HPV types 16, 18, 31, 33, 35, 39, 45, 51, 52, 56, 58, 59, and 68 were deemed carcinogenic (Group 1); HPV types 26, 30, 34, 53, 66, 67, 69, 70, 73, 82, 85, and 97 were possibly carcinogenic (Group 2B); and HPV types 6, 11, and others were not classifiable or not studied. To compare the prevalence of HPV genotypes grouped by carcinogenicity among the 3 cytological categories, the HPV genotype found in each sample was coded on an ordinal scale: HPV undetected (0), not classifiable (1), possibly carcinogenic (2), and carcinogenic (3). Cytology was coded as ordinal numbers: NILM (0), LSIL (1), and HSIL (2) to determine the correlation between HPV carcinogenicity and cytological grade.

Multivariable logistic regression (Reference 28) was performed to investigate the association between the methylation level of each CpG locus of a particular gene (ADCY8, CDH8, and ZNF582) and a binarized cytological outcome of interest. Outcome Model 1 aimed to distinguish normal from abnormal cytology (NILM vs. LSIL/HSIL); whereas, Model 2 distinguishes non-high- and high-grade cytology (NILM/LSIL vs. HSIL). The model equation is as follows:

Logistic model: Probability of outcome =

$$P(Y=1) = \frac{1}{1 + e^{-(b_0 + b_1 X_1 + \ldots + b_i X_i)}}$$

Multiple explanatory variables: $X_1, \ldots, X_i$ (where $X_i$=Gene X and CpG-position methylation level (%))
Model 1 Outcome (Y) coding: NILM (0), LSIL/HSIL (1)
Model 2 Outcome (Y) coding: NILM/LSIL (0), HSIL (1)

The covariates (CpG position selected from each gene) that had the highest association with the response variable (lowest P-value) were selected for cut-point (binarization) determination. The cut-points were chosen at the point of maximum accuracy (Σ sensitivity+specificity). The new binarized methylation variables of these CpG sites, along with HPV carcinogenic status, were entered in a $2^{nd}$ multi-variable logistic regression analysis to select the explanatory variables most predictive of the cytological outcome. The $2^{nd}$ model equation is as follows.

Logistic model: Probability of outcome =

$$P(Y=1) = \frac{1}{1 + e^{-(b_0 + b_1 X_1 + \ldots + b_4 X_4)}}$$

Multiple explanatory variables: $X_1, \ldots, X_4$
$X_1$=HPV carcinogenicity (coded as ordinal data as described in text)
$X_2$=ADCY8 CpG-position i methylation (0, 1)
$X_3$=CDH8 CpG-position i methylation (0, 1)
$X_4$=ZNF582 CpG-position i methylation (0, 1)
Model 1 Outcome (Y) coding: NILM (0), LSIL/HSIL (1)
Model 2 Outcome (Y) coding: NILM/LSIL (0), HSIL (1)

For the final regression models, post estimation receiver operating characteristic (ROC) curves were constructed and predictions at specified values were computed. After estimating the classification threshold or "cut-point" for each model by using the maximum sum of sensitivity and specificity, diagnostic performance characteristics were determined. The discriminatory performance between multivariable and univariable (HPV carcinogenicity only) models was compared using respective areas under the ROC curve. Pairwise comparisons of predicted probabilities between models were performed with the chi-squared test.

Statistical Analysis

Data were summarized using means (95% CI), medians (IQR), and proportions. For hypothesis testing, Wilcoxon rank sum and Kruskal-Wallis tests were used for non-parametric, numerical, or ordinal data. Categorical data were compared using the chi-squared test. Correlation between ordinal variables was determined by Spearman's rho. A P-values <0.05 was considered statistically significant.

For TCGA methylation analysis, the pyrosequencing CpG assay for each gene was translated into the Illumina assay by selecting the nearest CpG loci on the HM450K array. Methylation data (β-value, defined as the ratio of methylated signal over total signal (methylated+unmethylated)) (Reference 25) were used to determine promoter methylation levels of ADCY8, CDH8, MGMT, and ZNF582. The median methylation levels per locus were stratified by observation group, i.e., tumor stages, histologic category (normal/tumor) and tested for differences by non-parametric methods. All subsequent analyses compared median methylation levels across all CpGs per gene as the single sample summary measure. The relationship between methylation (β-value) and RNA-SeqV2 expression data (upper quartile of normalized RSEM count estimates) (Reference 18) was determined by Spearman's rho. Statistical analyses were performed using STATA/IC 13.0 (StataCorp LP, College Station, Tex.).

High-Resolution Melting Assay

High-resolution melting (HRM) analysis has been used to determine hypermethylation of CpG islands (e.g., Reference 48).

To determine whether the extent of DNA methylation in the promoter regions of CDH8, ZNF582, and ALK is suitable to distinguish HPV cytological grades by methylation-sensitive high-resolution melting (MS-HRM) analysis of bisulfate-treated DNA sequences, the following was conducted.

HRM analysis characterizes DNA samples according to their dissociation behavior as a function of increasing temperature. PCR amplification of a region of interest in the presence of a double-strand DNA-binding saturating dye, e.g., EvaGreen® generates high fluorescence upon formation of double-stranded (dsDNA) and low fluorescence in unbound, single-stranded DNA (ssDNA). After PCR amplification, during heating and melting of DNA (dsDNA dissociates into ssDNA), the saturating dye is released and detected as a steep decline in fluorescence. The resulting melting curve and melting point (Tm) at which 50% of DNA is dissociated are highly characteristic of the amplicon. Several sequence characteristics affect the Tm. The temperature or energy required to break the base-base hydrogen bonds between two DNA strands is dependent on sequence length, GC content, and number of methylated CpGs. Therefore, sequences which are longer or have higher numbers of GC base-pairs (triple hydrogen bonds) versus AT base-pairs (double hydrogen bonds) will possess higher melting points. Finally, DNA melting is considered a multi-state process which may result in multiple melting phases. In other words, the melting temperatures of a mixture of compounds or one compound with differences in regional CG content, e.g., CpG-island with high GC content, may result in multi-phase melting. Taken together, the unique characteristics of melting curves and temperatures may be utilized for mutation screening, genotyping, and methylation quantification.

Samples and Controls

Liquid-based cytology collected for clinical testing at the Department of Pathology of BAMC was consecutively procured after completion of analysis for cytological diagnosis. Samples were refrigerated at 4° C. until weekly batch DNA extraction. The Pap smear samples include negative for intraepithelial lesion or malignancy, low-grade squamous intraepithelial, and high-grade squamous intraepithelial lesion.

Genomic DNA Extraction and Sodium Bisulfite Conversion

Genomic DNA was extracted from clinical samples as previously reported using the QiaCube robotic work station according to manufacturer's instruction for QIAamp DNA Mini Kit (Qiagen). The DNA concentration was measured using the QIAxpert (Qiagen). The EpiTect Fast DNA Bisulfite kit (Qiagen) was used for bisulfite conversion of genomic DNA to convert unmethylated cytosine residues to uracil. Briefly, 20 µL of extracted genomic DNA (≥20 ng/µL) was mixed with EpiTect Bisulfite Solution and DNA Protect Buffer followed by bisulfite conversion using the Eppendorf Mastercycler Pro according to recommended cycling conditions: denaturation (95° C.×5 minutes) and incubation (60° C.×5 minutes) for two cycles and indefinite hold at 20° C. Bisulfate converted DNA was purified using the EpiTect Fast Bisulfite standard protocol on the QIAcube station and eluted in 15 µl elution buffer (Qiagen).

High Resolution Melting Analysis (HRM)

Real-time PCR amplification and high resolution melting analysis was performed on the Rotor-Gene Q 5Plex HRM (Qiagen). PCRs were performed in a final volume (25 µL) containing bisulfite-converted template DNA (100 ng), 2× EpiTect HRM PCR Master Mix (12.5 forward and reverse primers (10 µM each), and RNAase-free water. The cycling protocols for the 3 primer sets for CDH8, ZNF582, and ALK were as follows: activation (95° C.×5 minutes); 40-45 cycles of 3-step cycling (95° C.×10 seconds, 56° C.×30 seconds, 72° C.×14 seconds). High-resolution melting analysis was performed at temperature ramping (quick heating of amplicons) from 70° C. to 90° C. at 0.1° C. increments/2 seconds according to manufacturer's recommendations (Qiagen). Acquisition of fluorescence data during this phase generated the unique melt curves of the amplicons. All reactions were performed in duplicate.

EpiTect bisulfite-converted, methylated and unmethylated human control DNA (Qiagen) were used as positive (100%) and negative (0%) controls, respectively. A range of methylated DNA standards (20%, 40%, 60%) were generated using a mixture of the two control DNA standards (methylated and unmethylated). Methylated bisulfite-converted DNA standards (0%, 20%, 40%, 60%, and 100%) with a 10 ng/µL concentration were amplified and melted as above in duplicate control reactions.

HRM data analysis was conducted using the Rotor-Gene Q software. The five steps involved in quantification of methylated DNA were as follows: 1) determine the threshold cycle (CT) values and amplification efficiency for each sample. Treat samples as an outlier if the CT>30 or amplification efficiency score is ≤1.4 2) normalize fluorescence values for the pre- and post-melt regions to ensure all melt curves are compared with the same starting and ending fluorescence levels 3) generate negative first derivative melt plot (−dF/dT) as a function of temperature for the detection Tm of the products (peaks) 4) generate HRM Difference Plot by subtracting reference curves (using the 0% methylated standard) from sample and other standard curves, and 5) calculate the area-under-the-curve (AUC) of the Difference Plot using the Midpoint Riemann Sum formula for each standard to generate a linear regression plot against percent methylation for use as standard curve for determination of methylation levels in test samples.

HRM analysis allows for detection and quantification of the methylated fraction of DNA or amplicons in a clinical sample, as well as, the cumulative number of methylated CpGs flanked between the forward and reverse primers. The differential methylation between normal, precancerous, and cancerous tissues may thus be detected by HRM assays.

REFERENCES

The following references are herein incorporated by reference in their entirety:

1. Papanicolaou G N, Traut H F. The diagnostic value of vaginal smears in carcinoma of the uterus. American Journal of Obstetrics and Gynecology 1941; 42:193-206.
2. Carmichael D E, Cameron C. The Pap smear. In: The Pap smear: Life of George N. Papanicolaou. Springfield: Charles C. Thomas; 1973. p. 68-83.
3. Organization, World Health. Comprehensive cervical cancer control: a guide to essential practice. 2nd ed. Geneva: WHO; 2014. p. 23-72.

4. Durst M, Gissmann L, Ikenberg H, zur Hausen H. A papillomavirus DNA from a cervical carcinoma and its prevalence in cancer biopsy samples from different geographic regions. Proc Natl Acad Sci USA 1983; 80:3812-5.
5. Walboomers J M, Jacobs M V, Manos M M, Bosch F X, Kummer J A, Shah K V, et al. Human papillomavirus is a necessary cause of invasive cervical cancer worldwide. J Pathology 1999; 189:12-19.
6. Roche Molecular Systems. cobas HPV Test-package insert. www.fda.gov. (Online) 2011. (Cited: Apr. 4, 2015) www.accessdata.fda.gov/cdrh_docs/pdf10/p100020c.pdf.
7. Schiffman M, Clifford G, Buonaguro F M. Classification of weakly carcinogenic human papillomavirus types: addressing the limits of epidemiology at the borderline. Infectious Agents and Cancer 2009; 4:8.
8. International Agency for Research on Cancer. IARC Monographs on the evaluation of carcinogenic risks to humans-Human Papillomaviruses, Volume 100B. Geneva: World Health Organization; 2012. p. 255-313.
9. Laird P W. The power and the promise of DNA methylation markers. Nature Reviews Cancer 2003; 3:253-266.
10. Brebi P, Maldonado L, Noordhuis M G, Ili C, Leal P, Garcia P, Brait M, et al. Genome-wide methylation profiling reveals Zinc finger protein 516 (ZNF516) and FK-506-binding protein 6 (FKBP6) promoters frequently methylated in cervical neoplasia, associated with HPV status and ethnicity in a Chilean population. Epigenetics 2014; 9:308-317.
11. Huang R L, Chang C C, Su P H, Chen Y C, Liao Y P, Wang H C, et al. Methylomic analysis identifies frequent DNA methylation of zinc finger protein 582 (ZNF582) in cervical neoplasms. Plos One 2012; 7:e41060.
12. Saavedra K P, Brebi P M, Roa J C. Epigenetic alterations in preneoplastic and neoplastic lesions of the cervix. Clin Epigenetics. 2012; 4(1):13.
13. Wentzensen N, Sherman M E, Schiffman M, Wang S S. Utility of methylation markers in cervical cancer early detection: appraisal of the state-of-the-science. Gynecol Oncol. 2009; 112(2):293-9.
14. Hansel A, Steinbach D, Greinke C, Schmitz M, Eiselt J, Scheungraber C, et al. A promising DNA methylation signature for the triage of high-risk human papillomavirus DNA-positive women. PLoS One. 2014; 9(3):e91905.
15. Siegel E M, Riggs B M, Delmas A L, Koch A, Hakam A, Brown K D. Quantitative DNA methylation analysis of candidate genes in cervical cancer. PLoS One. 2015; 10(3):e0122495.
16. Lin H, Chen T C, Chang T C, Cheng Y M, Chen C H, Chu T Y, et al. Methylated ZNF582 gene as a marker for triage of women with Pap smear reporting low-grade squamous intraepithelial lesions—a Taiwanese Gynecologic Oncology Group (TGOG) study. Gynecol Oncol 2014; 135:64-68.
17. Lendvai A, Johannes F, Grimm C, Eijsink J J, Wardenaar R, Volders H H, et al. Genome-wide methylation profiling identifies hypermethylated biomarkers in high-grade cervical intraepithelial neoplasia. Epigenetics 2012; 7:1268-78.
18. Li B, Dewey C N. RSEM: accurate transcript quantification from RNA-Seq data with or without a reference genome. BMC Bioinformatics 2011; 4:323.
19. Gao J, Aksoy B A, Dogrusoz U, Dresdner G, Gross B, Sumer S O, et al. Integrative analysis of complex cancer genomics and clinical profiles using the cBioPortal. Science Signal 2013; 6:p11.
20. Resnick R M, Cornelissen M T, Wright D K, Eichinger G H, Fox H S, ter Schegget J, et al. Detection and typing of human papillomavirus in archival cervical cancer specimens by DNA amplification with consensus primers. J Natl Cancer Inst 1990; 82:1477-84.
21. Forslund O, Antonsson A, Nordin P, Stenquist B, Hansson B G. A broad range of human papillomavirus types detected with a general PCR method suitable for analysis of cutaneous tumours and normal skin. J Gen Virol 1999; 80:2437-43.
22. Sotlar K, Diemer D, Dethleffs A, Hack Y, Stubner A, Vollmer N, et al. Detection and typing of human papillomavirus by e6 nested multiplex PCR. J Clin Micro 2004; 42:3176-84.
23. Shen-Gunther J, Yu X. HPV molecular assays: defining analytical and clinical performance characteristics for cervical cytology specimens. Gynecol Oncol 2011; 123: 263-71.
24. Docherty S J, Davis O S, Haworth C M, Plomin R, Mill J. DNA methylation profiling using bisulfite-based epityping of pooled genomic DNA. Methods 2010; 52:255-8.
25. Farkas S A, Milutin-Gašperov N, Grce M, Nilsson T K. Genome-wide DNA methylation assay reveals novel candidate biomarker genes in cervical cancer. Epigenetics 2013; 8:1213-25.
26. Lechner M, Fenton T, West J, Wilson G, Feber A, Henderson S, et al. Identification and functional validation of HPV-mediated hypermethylation in head and neck squamous cell carcinoma. Genome Med 2013; 5:15.
27. Division, Computational Biology and Bioinformatics. Methylation Intensity for ADCY8 gene set. The Cancer Methylome System. (Online) 2012. (Cited: Aug. 1, 2013) http://cbbiweb.uthscsa.edu/KMethylomes/.
28. Long J S, Freese J. Models for binary outcomes: Interpretation. In: Regression models for categorical dependent variables using Stata. 3rd ed. College Station: Stata Press; 2014. p. 227-308.
29. Matlashewski G, Banks L. Papillomaviruses. In: Acheson N H. Fundamental of molecular virology. 2nd ed. Hoboken: John Wiley & Sons; 2011. p. 263-71.
30. Hanahan D, Weinberg R A. Hallmarks of cancer: the next generation. Cell 2011; 144:646-74.
31. de Sanjosé S, Diaz M, Castellsagué X, Clifford G, Bruni L, Munoz N, Bosch F X. Worldwide prevalence and genotype distribution of cervical human papillomavirus DNA in women with normal cytology: a meta-analysis. Lancet Infect Dis 2007; 7:453-9.
32. Chan P K, Zhang C, Park J S, Smith-McCune K K, Palefsky J M, Giovannelli L. Geographical distribution and oncogenic risk association of human papillomavirus type 58 E6 and E7 sequence variations. Int J Cancer 2013; 132:2528-36.
33. Vasiljević N, Scibior-Bentkowska D, Brentnall A R, Cuzick J, Lorincz A T. Credentialing of DNA methylation assays for human genes as diagnostic biomarkers of cervical intraepithelial neoplasia in high-risk HPV positive women. Gynecol Oncol 2014; 132:709-14.
34. ZNF582 zinc finger protein 582 (*Homo sapiens*). NCBI Gene. (Online) (Cited: Apr. 4, 2015) www.ncbi.nlm.nih.gov/gene/147948.
35. Lupo A, Cesaro E, Montano G, Zurlo D, Izzo P, Costanzo P. KRAB-Zinc Finger Proteins: A Repressor Family Displaying Multiple Biological Functions. Curr Genomics 2013; 14:268-78.
36. Chang C C, Huang R L, Wang H C, Liao Y P, Yu M H, Lai H C. High methylation rate of LMX1A, NKX6-1, PAX1, PTPRR, SOX1, and ZNF582 genes in cervical adenocarcinoma. Int J Gynecol Cancer 2014; 24:201-9.
37. CDH8 cadherin 8, type 2 (*Homo sapiens*). NCBI Gene. (Online) (Cited: Apr. 4, 2015) www.ncbi.nlm.nih.gov/gene/1006.
38. van Roy F. Beyond E-cadherin: roles of other cadherin superfamily members in cancer. Nat Rev Cancer 2014; 14:121-34.
39. ADCY8 adenylate cyclase 8 (brain) (*Homo sapiens*). NCBI Gene. (Online) (Cited: Apr. 4, 2015) www.ncbi.nlm.nih.gov/gene/114.
40. Warrington N M, Gianino S M, Jackson E, Goldhoff P, Garbow J R, Piwnica-Worms D, et al. Cyclic AMP suppression is sufficient to induce gliomagenesis in a mouse model of neurofibromatosis-1. Cancer Res 2010; 70:5717-27.
41. Orchel J, Witek L, Kimsa M, StrzALKa-Mrozik B, Kimsa M, Olejek A, et al. Expression patterns of kinin-dependent genes in endometrial cancer. Int J Gynecol Cancer 2012; 22:937-44.
42. Wojdacz T K, Dobrovic A. Methylation-sensitive high resolution melting (MS-HRM): a new approach for sensitive and high-throughput assessment of methylation. Nucleic Acids Res 2007; 35:e41.
43. Huang T T, Gonzales C B, Gu F, Hsu Y T, Jadhav R R, Wang C M, et al. Epigenetic deregulation of the Anaplastic Lymphoma Kinase gene modulates mesenchymal characteristics of oral squamous cell carcinomas. Carcinogenesis 34; 8:1717-27.
44. Jadhav R R, Ye Z, Huang R-L, Liu J, Hsu P-Y, Huang Y-W, et al. Genome-wide DNA methylation analysis reveals estrogen-mediated epigenetic repression of metallothionein-1 gene cluster in breast cancer. Clinical Epigenetics 2015; 7:13.
45. Hsu Y T, Gu F, Huang Y W, Liu J, Ruan J, Huang R L, Wang C M, et al. Promoter hypomethylation of EpCAM-regulated bone morphogenetic protein gene family in recurrent endometrial cancer. Clin Cancer Res 2013; 19:6272-85.
46. Ghosh S, Gu F, Wang C M, Lin C L, Liu J, Wang H, et al. Genome-wide DNA methylation profiling reveals parity-associated hypermethylation of FOXA1. Breast Cancer Res Treat 2014; 147:653-659.
47. Wolff E M, Byun H M, Han H F, Sharma S, Nichols P W, Siegmund K D, et al. Hypomethylation of a LINE-1 promoter activates an alternate transcript of the MET oncogene in bladders with cancer. PLoS Genet 2010; 22:e1000917.
48. Malentacchi F, Forni G, Vinci S, Orlando C. Quantitative evaluation of DNA methylation by optimization of a differential-high resolution melt analysis protocol. Nucleic Acids Research 2009, 37(12): e86.

All scientific and technical terms used in this application have meanings commonly used in the art unless otherwise specified.

As used herein, the term "subject" includes humans and non-human animals. The term "non-human animal" includes all vertebrates, e.g., mammals and non-mammals, such as non-human primates, horses, sheep, dogs, cows, pigs, chickens, and other veterinary subjects and test animals.

The use of the singular can include the plural unless specifically stated otherwise. As used in the specification and the appended claims, the singular forms "a", "an", and "the" can include plural referents unless the context clearly dictates otherwise. The use of "or" can mean "and/or" unless stated otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of determining the methylation level of one or more CpG sites of a nucleic acid molecule obtained from a cervical cell sample that has been infected with a Human papillomavirus having genotype 114, 91, 90, 84, 83, 81, 72, 71, 61, 54, 43, 42, 11, 6, 97, 85, 82, 73, 70, 69, 67, 66, 53, 34, 30, 26, a9, 68, 59, 58, 56, 52, 51, 45, 39, 35, 33, 31, 18, or 16, which comprises
   a) converting unmethylated cytosine residues of the nucleic acid molecule to uracil by contacting the nucleic acid molecule with bisulfite to obtain a bisulfite converted nucleic acid molecule;
   b) subjecting the bisulfite converted nucleic acid molecule to polymerase chain reaction amplification using a set of primers to obtain amplified nucleic acid molecules; and
   c) determining the methylation level of the one or more CpG sites, wherein said nucleic acid molecule has a sequence identity of at least 95% to SEQ ID NO: 4 and the set of primers are SEQ ID NO: 15 and SEQ ID NO: 16.

2. The method according to claim 1, wherein the polymerase chain reaction amplification is real-time polymerase chain reaction amplification.

3. The method according to claim 1, wherein step c) is performed by high resolution melt analysis.

4. The method according to claim 1, wherein step c) is performed by pyrosequencing.

5. The method according to claim 1, wherein the HPV genotype is selected from the group consisting of: 114, 91, 90, 84, 83, 81, 72, 71, 61, 54, 43, 42, 11, 6, 97, 85, 82, 73, 70, 69, 67, 66, 53, 34, 30, 26, a9, 68, 59, 58, 56, 52, 51, 45, 39, 35, 33, 31, 18, and 16.

6. The method according to claim 5, wherein the HPV genotype is selected from the group consisting of: 114, 91, 90, 84, 83, 81, 72, 71, 61, 54, 43, 42, 11, 6, 97, 85, 82, 73, 70, 69, 67, 66, 53, 34, 30, 26, a9, 68, 59, 58, 56, 52, 51, 45, 39, 35, 33, 31, 18, and 16.

7. The method according to claim 5, wherein the HPV genotype is 97, 85, 82, 73, 70, 69, 67, 66, 53, 34, 30, 26, a9, 68, 59, 58, 56, 52, 51, 45, 39, 35, 33, 31, 18, or 16.

8. The method according to claim 5, wherein the HPV genotype is a9, 68, 59, 58, 56, 52, 51, 45, 39, 35, 33, 31, 18, or 16.

9. The method according to claim 1, wherein the one or more CpG sites are selected from the group consisting of CpG 1, CpG 2, CpG 3, CpG 4, CpG 5, CpG 6, CpG 7, CpG 8, CpG 9, CpG 10, CpG 11, and CpG 12 of SEQ ID NO: 4.

10. The method according to claim 9, wherein the one or more CpG sites includes CpG 5 of SEQ ID NO: 4.

11. The method according to claim 1, and further comprising measuring the methylation level of one or more additional CpG sites selected from the group consisting of CpG sites of a nucleic acid molecule having a sequence identity of at least 95% to SEQ ID NO:
1, CpG sites of a nucleic acid molecule having a sequence identity of at least 95% to SEQ ID NO: 2, and CpG sites of a nucleic acid molecule having a sequence identity of at least 95% to SEQ ID NO: 3.

12. The method according to claim 1, and further comprising measuring the methylation level of one or more additional CpG sites selected from the group consisting of
a) CpG 1, CpG 2, CpG 3, CpG 4, CpG 5, CpG 6, CpG 7, and CpG 8 of SEQ ID NO: 1;
b) CpG 1, CpG 2, CpG 3, CpG 4, and CpG 5 of SEQ ID NO: 2; and
c) CpG 1, CpG 2, CpG 3, CpG 4, and CpG 5 of SEQ ID NO: 3.

13. The method of claim 12, wherein the one or more additional CpG sites is CpG 7 of SEQ ID NO: 1, CpG 3 of SEQ ID NO: 2, or CpG 3 of SEQ ID NO: 3.

\* \* \* \* \*

SEQUENCE LISTING

```
<160> NUMBER OF SEQ ID NOS: 17

<210> SEQ ID NO 1
<211> LENGTH: 52
<212> TYPE: DNA
<213> ORGANISM: Homo sapiens

<400> SEQUENCE: 1
cgcgccgcag ctgtcaggcg actcggcgct gcccctctac tcgctgggcc cg          52

<210> SEQ ID NO 2
<211> LENGTH: 41
<212> TYPE: DNA
<213> ORGANISM: Homo sapiens

<400> SEQUENCE: 2
cggctacgga gtccccggct taaggggcc tccgtgcacg c                        41

<210> SEQ ID NO 3
```

-continued

```
<211> LENGTH: 26
<212> TYPE: DNA
<213> ORGANISM: Homo sapiens

<400> SEQUENCE: 3
acgcagacgt ctcgcctcat cgtcgc                                          26

<210> SEQ ID NO 4
<211> LENGTH: 80
<212> TYPE: DNA
<213> ORGANISM: Homo sapiens

<400> SEQUENCE: 4
cgccgcctct gttcggaggg tcgcggggca ccgaggtgct ttccggccgc cctctggtcg     60
gccacccaaa gccgcgggcg                                                 80

<210> SEQ ID NO 5
<211> LENGTH: 20
<212> TYPE: DNA
<213> ORGANISM: Artificial Sequence
<220> FEATURE:
<223> OTHER INFORMATION: Primer sequence based on Human papilloma virus.

<400> SEQUENCE: 5
cgtccmarrg gawactgatc                                                 20

<210> SEQ ID NO 6
<211> LENGTH: 20
<212> TYPE: DNA
<213> ORGANISM: Artificial Sequence
<220> FEATURE:
<223> OTHER INFORMATION: Primer sequence based on Human papilloma virus.

<400> SEQUENCE: 6
gcmcagggwc ataayaatgg                                                 20

<210> SEQ ID NO 7
<211> LENGTH: 21
<212> TYPE: DNA
<213> ORGANISM: Artificial Sequence
<220> FEATURE:
<223> OTHER INFORMATION: Primer sequence based on Human papilloma virus.
<220> FEATURE:
<221> NAME/KEY: misc_feature
<222> LOCATION: (8)..(8)
<223> OTHER INFORMATION: Wherein n is deoxyinosine.
<220> FEATURE:
<221> NAME/KEY: misc_feature
<222> LOCATION: (11)..(11)
<223> OTHER INFORMATION: Wherein n is deoxyinosine.

<400> SEQUENCE: 7
taacwgtngg ncayccwtat t                                               21

<210> SEQ ID NO 8
<211> LENGTH: 23
<212> TYPE: DNA
<213> ORGANISM: Artificial Sequence
<220> FEATURE:
<223> OTHER INFORMATION: Primer sequence based on Human papilloma virus.
<220> FEATURE:
<221> NAME/KEY: misc_feature
<222> LOCATION: (15)..(15)
<223> OTHER INFORMATION: Wherein n is deoxyinosine.
<220> FEATURE:
<221> NAME/KEY: misc_feature
<222> LOCATION: (18)..(18)
<223> OTHER INFORMATION: Wherein n is deoxyinosine.
```

<400> SEQUENCE: 8
ccwatatcwv hcatntcncc atc                                              23

<210> SEQ ID NO 9
<211> LENGTH: 19
<212> TYPE: DNA
<213> ORGANISM: Artificial Sequence
<220> FEATURE:
<223> OTHER INFORMATION: Primer sequence based on Human papilloma virus.

<400> SEQUENCE: 9
gggwgkkact gaaatcggt                                                   19

<210> SEQ ID NO 10
<211> LENGTH: 23
<212> TYPE: DNA
<213> ORGANISM: Artificial Sequence
<220> FEATURE:
<223> OTHER INFORMATION: Primer sequence based on Human papilloma virus.
<220> FEATURE:
<221> NAME/KEY: misc_feature
<222> LOCATION: (13)..(13)
<223> OTHER INFORMATION: n is a, c, g, or t

<400> SEQUENCE: 10
ctgagctgtc arntaattgc tca                                              23

<210> SEQ ID NO 11
<211> LENGTH: 23
<212> TYPE: DNA
<213> ORGANISM: Artificial Sequence
<220> FEATURE:
<223> OTHER INFORMATION: Primer sequence based on Human papilloma virus.

<400> SEQUENCE: 11
tcctctgagt ygyctaattg ctc                                              23

<210> SEQ ID NO 12
<211> LENGTH: 22
<212> TYPE: DNA
<213> ORGANISM: Artificial Sequence
<220> FEATURE:
<223> OTHER INFORMATION: Forward primer sequence based on Homo sapiens
      ADCY8 gene.

<400> SEQUENCE: 12
agtggaggtt agggtaaagt tt                                               22

<210> SEQ ID NO 13
<211> LENGTH: 30
<212> TYPE: DNA
<213> ORGANISM: Artificial Sequence
<220> FEATURE:
<223> OTHER INFORMATION: Reverse primer sequence based on Homo sapiens
      ADCY8 gene.
<220> FEATURE:
<221> NAME/KEY: misc_feature
<222> LOCATION: (1)..(1)
<223> OTHER INFORMATION: Biotin bound thereto.

<400> SEQUENCE: 13
taacccctcc ataactataa cccccattaa                                       30

<210> SEQ ID NO 14
<211> LENGTH: 20
<212> TYPE: DNA

```
<213> ORGANISM: Artificial Sequence
<220> FEATURE:
<223> OTHER INFORMATION: Based on Homo sapiens ADCY8 gene.
<220> FEATURE:
<221> NAME/KEY: misc_feature
<222> LOCATION: (1)..(1)
<223> OTHER INFORMATION: Biotin bound thereto.

<400> SEQUENCE: 14
gggaggaggt tttaattatt                                              20

<210> SEQ ID NO 15
<211> LENGTH: 25
<212> TYPE: DNA
<213> ORGANISM: Artificial Sequence
<220> FEATURE:
<223> OTHER INFORMATION: Forward primer sequence based on Homo sapiens
      ALK gene.

<400> SEQUENCE: 15
ggtagaggtg gtagtagttg gtatt                                        25

<210> SEQ ID NO 16
<211> LENGTH: 19
<212> TYPE: DNA
<213> ORGANISM: Artificial Sequence
<220> FEATURE:
<223> OTHER INFORMATION: Reverse primer sequence based on Homo sapiens
      ALK gene.
<220> FEATURE:
<221> NAME/KEY: misc_feature
<222> LOCATION: (1)..(1)
<223> OTHER INFORMATION: Biotin bound thereto.

<400> SEQUENCE: 16
ccctcctcac ccatcatca                                               19

<210> SEQ ID NO 17
<211> LENGTH: 19
<212> TYPE: DNA
<213> ORGANISM: Artificial Sequence
<220> FEATURE:
<223> OTHER INFORMATION: Based on Homo sapiens ALK gene.

<400> SEQUENCE: 17
gtggtagtag ttggtattt                                               19
```